(12) United States Patent
Thierry et al.

(10) Patent No.: US 9,580,755 B2
(45) Date of Patent: Feb. 28, 2017

(54) ANALYTICAL METHODS FOR CELL FREE NUCLEIC ACIDS AND APPLICATIONS

(75) Inventors: Alain Thierry, Saint Clement (FR); Franck Molina, Les Matelles (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 13/820,302

(22) PCT Filed: Sep. 5, 2011

(86) PCT No.: PCT/EP2011/065333
§ 371 (c)(1),
(2), (4) Date: May 14, 2013

(87) PCT Pub. No.: WO2012/028746
PCT Pub. Date: Mar. 8, 2012

(65) Prior Publication Data
US 2013/0224740 A1     Aug. 29, 2013

Related U.S. Application Data

(60) Provisional application No. 61/380,084, filed on Sep. 3, 2010.

(30) Foreign Application Priority Data

Sep. 3, 2010 (EP) .................................... 10305952

(51) Int. Cl.
*C12Q 1/68* (2006.01)
(52) U.S. Cl.
CPC .......... *C12Q 1/6886* (2013.01); *C12Q 1/6851* (2013.01); *C12Q 1/6883* (2013.01); *C12Q 2600/16* (2013.01); *C12Q 2600/178* (2013.01)
(58) Field of Classification Search
None
See application file for complete search history.

(56) References Cited

FOREIGN PATENT DOCUMENTS

WO   WO 2009/051842   4/2009

OTHER PUBLICATIONS

Gineikiene et al. J Molecular Diagnostics. Jan. 2009. 11(1): 66-74.*
Anker et al. "Detection of circulating tumour DNA in the blood (plasma/serum) of cancer patients," Cancer Metastasis Rev, 1999, pp. 65-73, vol. 18 (Abstract), abstract only.
Chan et al., "Size distributions of maternal and fetal DNA in maternal plasma," Clin Chem, 2004, pp. 88-92, vol. 50.
Deligezer et al., "Size distribution of circulating cell-free DNA in sera of breast cancer patients in the course of adjuvant chemotherapy," Clin Chem Lab Med, 2008, pp. 311-31 7, vol. 46 (Abstract), abstract only.

Diehl et al., "Detection and quantification of mutations in the plasma of patients with colorectal tumors," Proc Natl Acad Sci U S A, 2005, pp. 16368-16373, vol. 102.
Einspahr et al., "Associations of Ki-ras proto-oncogene mutation and p53 gene overexpression in sporadic colorectal adenomas with demographic and clinicopathologic characteristics," Cancer Epidemiol Biomarkers Prev, 2006, pp. 1443-1450, vol. 15.
Ferron et al., "The genetics of colorectal cancer," Ann Chir, 2005, pp. 602-607, vol. 130.
Frattini et al., "Quanitative Analysis of Plasma DNA in Colorectal Cancer Patients," Annals of the New York Academy of Sciences, vol. 1075, Circulating Nucleic Acids in Plasma and Serum IV, 2006, pales 185-190, abstract only.
Fuming Sang et al., "Comparisons between capillary zone electrophoresis and real-time PCR for quantification of circulating DNA levels in human sera," Journal of Chromatography B, Jul. 11, 2006, pp. 122-128, vol. 838, No. 2.
Gormally et al., "Amount of DNA in plasma and cancer risk: a prospective study," Int J Cancer, 2004, pp. 746-749, vol. 111.
Holdenrieder et al., "Cell-free DNA in serum and plasma: comparison of ELISA and quantitative PCR," Clin Chem, 2005, pp. 1544-1546, vol. 51.
Hua Hu et al., "Prenatal diagnosis of β-thalassemia by chip-based capillary electrophoresis," Prenatal Diagnosis, 2008, pp. 222-229, vol. 28, No. 3 (Abstract), abstract only.
Lievre et al., "KRAS mutations as an independent prognostic factor in patients with advanced colorectal cancer treated with cetuximab," J Clin Oncol, 2008, pp. 374-379, vol. 26.
Mamon et al., "Preferential amplification of apoptotic DNA from plasma: potential for enhancing detection of minor DNA alterations in circulating," DNA. Clin Chem, 2008, pp. 1582-1584, vol. 54.
Schmidt et al., "Integrity of cell-free plasma DNA in patients with lung cancer and nonmalignant lung disease," Ann N Y Acad Sci, 2008, pp. 207-213, vol. 1137 (Abstract), abstract only.
Smith et al., "Mutations in APC, Kirsten-ras, and p53—alternative genetic pathways to colorectal cancer," Proc Natl Acad Sci USA, 2002, pp. 9433-9438, vol. 99.
Stroun et al., "Isolation and characterization of DNA from the plasma of cancer patients," Eur J Cancer Clin Oncol, 1987, pp. 707-712, vol. 23 (Abstract), abstract. only.

(Continued)

*Primary Examiner* — Carla Myers
(74) *Attorney, Agent, or Firm* — Foley & Lardner LLP

(57) ABSTRACT

The present invention is directed to an in vitro method of detecting cell free nucleic acids, preferably cell free DNA (cfDNA) in a body fluid sample from an individual or a patient, wherein the method comprises the step of accurately and sensitively determining the concentration of cell free nucleic acid in the sample and/or determining the concentration or amount of said cell free nucleic acid of a size range and/or the index of integrity or size fraction ratio (SFR) of said cell free nucleic acid and/or the determination of the presence of genetic polymorphisms (such as known Single Nucleotide Polymorphisms (SNPs) or mutations). The invention encompasses also a method to discriminate body fluid individuals where cfDNA are highly released by comparing the size profile obtained for at least one of three size ranges of cfDNA. The invention also encompasses a method for analyzing cell nucleic acids in individuals for the diagnosis, prognosis or for assessing the evolution of a physiological state, such as the progression of a tumor or metastatic cancer, for monitoring the efficacy of a cancer treatment in a patient or for theragnostic purposes implementing the analysis of these biomarkers.

Figure 1:
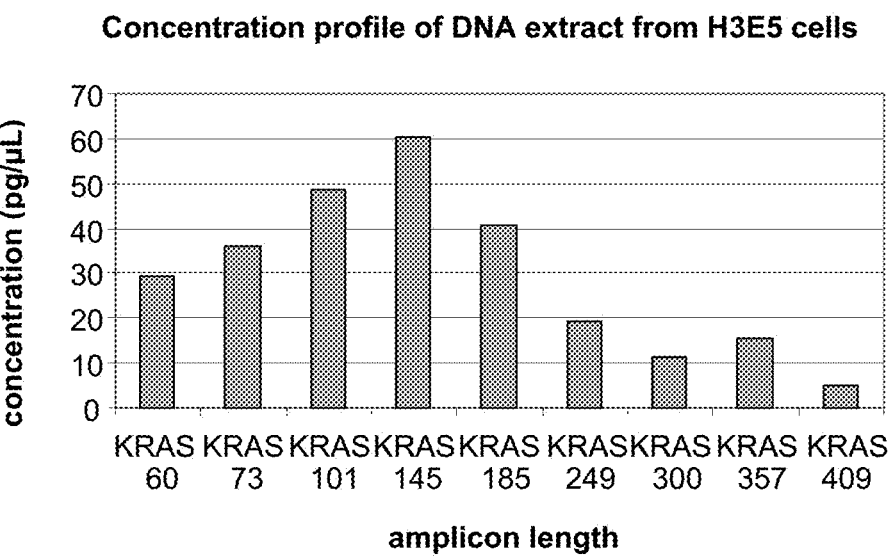

3 Claims, 26 Drawing Sheets
(21 of 26 Drawing Sheet(s) Filed in Color)

(56) References Cited

OTHER PUBLICATIONS

Struchkov et al., "DNA-bound lipids of normal and tumor cells: retrospective and outlooks for functional genomics," Bioelectrochemistry, 2002, pp. 23-30, vol. 58.
Thierry et al., "Origin and quantification of circulating DNA in mice with human colorectal cancer xenografts," Nucleic Acids Res., May 21, 2010.
Umetani et al., "Prediction of breast tumor progression by integrity of free circulating DNA in serum," J Clin Oncol, 2006, pp. 4270-4276, vol. 24.
Wang et al., "Increased plasma DNA integrity in cancer patients," Cancer Res, 2003, pp. 3966-3968, vol. 63.
Partial European Search Report issued in application No. EP 10 30 5952 on Nov. 16, 2010.
Sung et al., "Differential Expression of MicroRNAs in Plasma of Colorectal Cancer Patients: A Potential Marker for Colorectal Cancer Screening," Gastroenterology, vol. 136, No. 5, pp. A-165, May 1, 2009.
Liu et al., "Decoding Circulating Nucleic Acids in Human Serum Using Microfluidic Single Molecule Spectroscopy," Journal of the American Chemical Society, vol. 132, No. 16, pp. 5793-5798, Apr. 28, 2010.
Koide et al., "Fragmentation of cell-free fetal DNA in plasma and urine of pregnant women," Prenatal Diagnosis, vol. 25, No. 7, pp. 604-607, Jul. 2005.
Thierry et al, "Origin and quantification of circulating DNA in mice with human colorectal cancer xenografts," Nucleic Acids Research, vol. 38, No. 18, pp. 6159-6175, May 21, 2010.
Ellinger et al., "Cell-Free Circulating DNA: Diagnostic Value in Patients with Testicular Germ Cell Cancer," Journal of Urology, vol. 181, No. 1, pp. 363-371, Jan. 1, 2009.
Ellinger et al., "Circulating mitochondrial DNA in the serum of patients with testicular germ cell cancer as a novel noninvasive diagnostic biomarker," BJU International, vol. 104, No. 1, pp. 48-52, Jul. 2009.
Board et al., "Isolation and extraction of circulating tumor DNA from patients with small cell lung cancer," Annals of the New York Academy of Sciences, pp. 98-107, 2008.
Wu et al., "Cell-free DNA: measurement in various carcinomas and establishment of normal reference range," Clinica Chimica Acta, vol. 321, pp. 77-87, Jan. 1, 2002.
Tong et al., "Diagnostic developments involving cell-free (circulating) nucleic acids," Clinica Chimica Acta, vol. 363, No. 1-2, Jan. 1, 2006.
Fleischhacker et al., "Circulating nucleic acids (CNAs) and cancer—A survey," BBA—Reviews on Cancer, vol. 1775, No. 1, pp. 181-232, Dec. 13, 2006.
Van der Vaart et al., "Is the role of circulating DNA as a biomarker of cancer being prematurely overrated ?," Clinical Biochemistry, vol. 43, No. 1-2, pp. 26-36, Jan. 1, 2010.
International Search Report issued in application No. PCT/EP2011/065333 on Jan. 6, 20102.

* cited by examiner

| Samples | Amplicons sizes (bp) | | | | | | | | Integrity index | | | | | | | |
|---|---|---|---|---|---|---|---|---|---|---|---|---|---|---|---|---|
| | 80 | 73 | 101 | 145 | 185 | 249 | 300 | 357 | 409 | 80 | 73 | 101 | 145 | 185 | 249 | 300 | 357 | 409 |
| CRC 1 | 1809.91 | 1905.15 | 1537.95 | 1015.81 | 453.61 | 128.49 | 80.91 | 74.82 | 1.81 | 1.000 | 1.053 | 0.850 | 0.561 | 0.251 | 0.070 | 0.034 | 0.014 | 0.001 |
| CRC 2 | 477.96 | 737.87 | 652.62 | 396.64 | 227.79 | 122.51 | 59.49 | 48.22 | 29.34 | 1.000 | 1.544 | 1.365 | 0.830 | 0.477 | 0.258 | 0.124 | 0.101 | 0.061 |
| CRC 3 | 138.44 | 187.85 | 186.15 | 124.94 | 51.83 | 21.16 | 12.74 | 9.33 | 2.34 | 1.000 | 1.355 | 1.345 | 0.902 | 0.374 | 0.153 | 0.092 | 0.067 | 0.017 |
| mean CCR | 808.57 | 943.59 | 792.24 | 512.53 | 244.40 | 90.05 | 44.38 | 44.06 | 11.10 | | 1.317 | 1.187 | 0.765 | 0.367 | 0.160 | 0.083 | 0.070 | 0.028 |
| | | | | | | | | | | | | | | | | | | |
| DII 300/60 | | | | | | | | | | | | 0.840 | 0.543 | 0.259 | 0.095 | 0.047 | 0.047 | 0.012 |
| DII 300/73 | | | | | | | | | | 0.857 | | | | | | | | |

| HHP 1 | 5.55 | 5.22 | 6.28 | 3.94 | 3.91 | 2.77 | 1.24 | 1.11 | 0.72 | 1.000 | 0.941 | 1.128 | 0.710 | 0.705 | 0.499 | 0.223 | 0.200 | 0.130 |
|---|---|---|---|---|---|---|---|---|---|---|---|---|---|---|---|---|---|---|
| HHP 2 | 2.51 | 4.07 | 4.89 | 4.08 | 3.58 | 3.12 | 2.71 | 2.38 | 1.75 | 1.000 | 1.622 | 1.948 | 1.625 | 1.418 | 1.243 | 1.080 | 0.948 | 0.697 |
| HHP 3 | 4.12 | 5.49 | 7.42 | 4.26 | 2.89 | 4.48 | 3.06 | 2.00 | 2.12 | 1.000 | 1.333 | 1.801 | 1.034 | 0.701 | 1.087 | 0.743 | 0.485 | 0.272 |
| mean HHP | 4.06 | 4.93 | 6.19 | 4.09 | 3.45 | 3.46 | 2.34 | 1.83 | 1.20 | | 1.298 | 1.626 | 1.123 | 0.941 | 0.943 | 0.682 | 0.545 | 0.366 |
| | | | | | | | | | | | | | | | | | | |
| DII 300/60 | | | | | | | | | | | | 1.256 | 0.830 | 0.700 | 0.701 | 0.474 | 0.371 | .243 |
| DII 300/73 | | | | | | | | | | 0.8235294 | | | | | | | | |

| | 80 | 73 | 101 | 145 | 185 | 249 | 300 | 357 | 409 |
|---|---|---|---|---|---|---|---|---|---|
| HHP/CCRDII 300/60 | | 0.99 | 1.37 | 1.47 | 2.56 | 5.9 | 8.18 | 7.8 | 13.88 |
| HHP/CCRDII 300/73 | 0.96 | | 1.49 | 1.82 | 2.7 | 7.34 | 10.07 | 7.95 | 20.64 |

FIGURE 18A

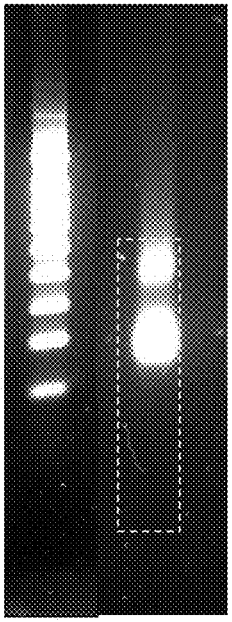
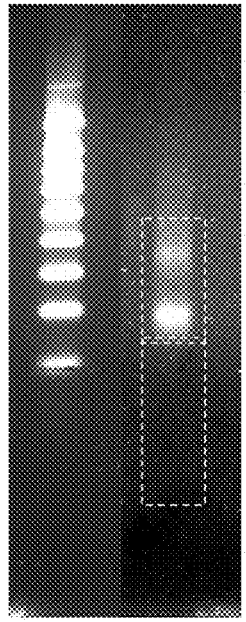
FIGURE 19A            FIGURE 19B
⌐ ¬: Limit of the section of the gel which was removed, solubilised, extracted and subjected to Q-PCR.
FIGURES 19A-19B

Figure 22A  Figure 22B  Figure 22C
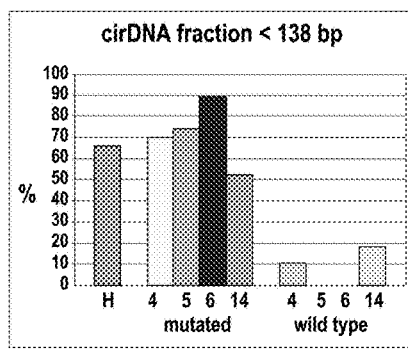
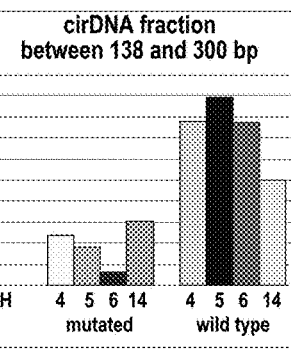
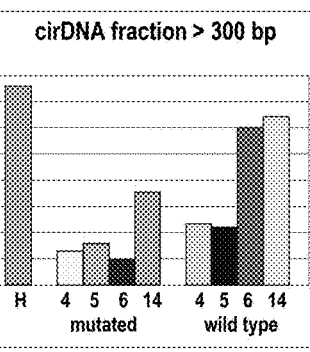
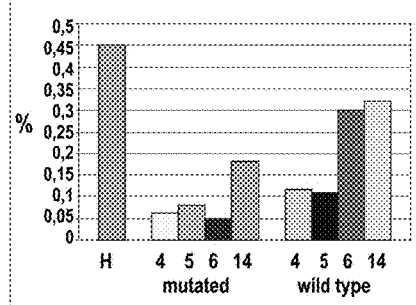
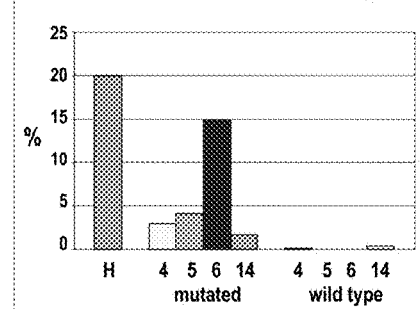
Figure 22D  Figure 22E
Figures 22A-22E Full Length = 278

```
171301 ATAAAGGATTGTGCATGCATGTATAGGAGAGCAGGATACCACAGCTGCTTTTGGTTTCT
                                Braf conv A1 (ID : 16)
171361 CGACAACTGAACATTACAAGAAAATCTATCAGAAGTCTTTACAATAGTAGGAGTTTTTGA
                                                        Braf conv A2 (ID : 258)
171421 TTGCTTGCTTACATTTTATCAGCACTATAAAACTGATAGTTTTGTAGCTATCTATTAGTC
171481 CCTTTCAGACCTCTGACCTTGCTCAGTGGTAGTTGAGATATAACTGAAGACTCTAAATTA
171541 TATAACAATGAGGTGAGAAAAACATAATATTTCTCTTCCCTAAGTGCAGACTAAGATACT
171601 ATCTGCAGCATCTTCATTCCAATGAAGAGCCTTTACTGCTCGCCCAGGAGTGCCAAGAGA
171661 ATATCTGGGCCTACATTGCTAAAATCTAATGGGAAAGTTTTAGGTTCTCCTATAAACTTA
171721 GGAAAGCATCTCACCTCATCCTAACACATTTCAAGCCCCAAAAATCTTAAAAGCAGGTTA
171781 TATAGGCTAAATAGAACTAATCATTGTTTTAGACATACTTATTGACTCTAAGACGAAAGA
                                              Braf conv A1v1 (ID : 23)
171841 TGAAGTACTATGTTTTAAAGAATATTATATTACAGAATTATAGAAATTAGATCTCTTACC
171901 TAAACTCTTCATAATGCTTGCTCTGATAGGAAAATGAGATCTACTGTTTTCCTTTACTTA
       Braf convA2v2 (ID : 259)
171961 CTACACCTCAGATATATTTCT                       TAGGTGATTTTGGTCT
172021 AGCTACAGTGAAATCTCGATGGAGTGGGTCCCATCAGTTTGAACAGTTGTCTGGATCCAT
       Braf inv B1 V600E blc (ID : 260)
   172046 - A
           AGCTACAGA
           Braf conv B1 V600E (ID : 26)
             GCTACAGTGAAATCTCGATGG
             Braf conv V600E Blocker (ID : 27)
172081 TTGTGGATGGTAAGAATTGAGGCTATTTTTCCACTGATTAAATTTTTGGCCCTGAGATG
       Braf conv B2 (ID : 261)
172141 CTGCTGAGTTA                          TATAGTATTTTCATA
172201                 GTGTTCTTATTTTTTATGTAAATAGATTTTTTAACTTTTTTCTTTA
172261 CCCTTAAAACGAATATTTTGAAACCAGTTTCAGTGTATTTCAAACAAAAATATATGTCTT
172321 ATAAACAGTGTTTCATATTTTATTCTTAAATAAATATGAACCCTTAAAACGAATATTTTG
172381 AAACCAGTTTCAGTGTATTTCAAACAAAAATATATGTCTTATAAACAGTGTTTCATATTT
172441 TATTCTAAATTGTTTAAAGTATTTTGTGTTCAAAATGTTCTGTGTACCCTGTTGAAAAAA
```

FIGURE 23

Design KRAS conv:
XXXXX : reverse primer for mutated amplicon: 6156 to 6236
▓▓▓▓▓ : primer pair for non mutated amplicon: 5721 to 6051
SEQ ID NO: 215

```
 5521   TTATTTCCCCATGACACAATCCAGCTTTATTTGACACTCATTCTCTCAACTCTCATCTGA   5580
 5581   TTCTTACTGTTAATATTTATCCAAGAGAACTACTGCCATGATGCTTTAAAAGTTTTTCTG   5640
 5641   TAGCTGTTGCATATTGACTTCTAACACTTAGAGGTGGGGGTCCACTAGGAAAACTGTAAC   5700
 5701   AATAAGAGTGGAGATAGCTG                                            ....
 ....                                                                  ....
                                                         AGTATTTGA   6060
 6061   TAGTGTATTAACCTTATGTGTGACATGTTCTAATATAGTCACATTTTCATTATTTTTATT   6120
 6121   ATAACGCCTGCTGAAAATGACTGAATATAA CTTGTGGTAGTTGGAGCTGGTGGCGTAGG   ....
 ....   CAAGAGTGCCTTGACGATACAGCTAATTCAGAATCATTTTGTGGACGAATATGATCCAAC   6240
 6241   AATAGAGGTAAATCTTGTTTTAATATGCATATTACTGGTGCAGGACCATTCTTTGATACA   6300
 6301   GATAAAGGTTTCTCTGACCATTTTCATGAGTACTTATTACAAGATAATTATGCTGAAAGT   6360
 6361   TAAGTTATCTGAAATGTACCTTGGGTTTCAAGTTATATGTAACCATTAATATGGAACTT    6420
 6421   TACTTTCCTTGGGAGTATGTCAGGGTCCATGATGTTCACTCTCTGTGCATTTGATTGGA    6480
 6481   AGTGTATTTCAGAGTTCGTGAGAGGGTAGAAATTTGTATCCTATCTGGACCTAAAAGAC   6540
 6541   AATCTTTTTATTGTAACTTTTATTTTTATGGGTTTCTTGGTATTGTGACATCATATGTAA   6600
 6601   AGGTTAGATTTAATTGTACTAGTGAAATATAATTGTTTGATGGTTGATTTTTTAAACTT   6660
 6661   CATCAGCAGTATTTCCTATCTTCTTCTCAACATTAGAGAACCTACAACTACCGGATAAA    6720
 6721   TTTTACAAAATGAATTATTTGCCTAAGGTGTGGTTTATATAAAGGTACTATTACCAACTT   6780
 6781   TACCTTTGCTTTGTTGTCATTTTTAAATTTACTCAAGGAAATACTAGGATTTAAAAAAAA   6840
```

Design KRAS rev:
XXXXX : reverse primer for mutated amplicon: 6066 to 6146
▓▓▓▓▓ : primer pair for non mutated amplicon: 6251 to 6581
SEQ ID NO: 215

```
 5521   TTATTTCCCCATGACACAATCCAGCTTTATTTGACACTCATTCTCTCAACTCTCATCTGA   5580
 5581   TTCTTACTGTTAATATTTATCCAAGAGAACTACTGCCATGATGCTTTAAAAGTTTTTCTG   5640
 5641   TAGCTGTTGCATATTGACTTCTAACACTTAGAGGTGGGGGTCCACTAGGAAAACTGTAAC   5700
 5701   AATAAGAGTGGAGATAGCTGTCAGCAACTTTTGTGAGGGTGTGCTACAGGGTGTAGAGCA   5760
 5761   CTGTGAAGTCTCTACATGAGTGAAGTCATGATATGATCCTTTGAGAGCCTTTAGCCGCCG   5820
 5821   CAGAACAGCAGTCTGGCTATTTAGATAGAACAACTTGATTTTAAGATAAAAGAACTGTCT   5880
 5881   ATGTAGCATTTATGCATTTTCTTAAGCGTCGATGGAGGAGTTTGTAAATGAAGTACAGT    5940
 5941   TCATTACGATACACGTCTGCAGTCAACTGGAATTTTCATGATTGAATTTTGTAAGGTATT   6000
 6001   TTGAAATAATTTTTCATATAAAGGTGAGTTTGTATTAAAAGGTACTGGTGGAGTATTTGA   6060
 6061   TAGT                                                          ....
                 GCCTGCTGAAAATGACTGAATATAA CTTGTGGTAGTTGGAGCTGGTGGCGTAGG   6180
 6181   CAAGAGTGCCTTGACGATACAGCTAATTCAGAATCATTTTGTGGACGAATATGATCCAAC   6240
 6241   AATAGAGG                                                       ....
 ....                                                                  ....
                                                  TGTGACATCATATGTAA   6600
 6601   AGGTTAGATTTAATTGTACTAGTGAAATATAATTGTTTGATGGTTGATTTTTTAAACTT   6660
 6661   CATCAGCAGTATTTCCTATCTTCTTCTCAACATTAGAGAACCTACAACTACCGGATAAA    6720
 6721   TTTTACAAAATGAATTATTTGCCTAAGGTGTGGTTTATATAAAGGTACTATTACCAACTT   6780
 6781   TACCTTTGCTTTGTTGTCATTTTTAAATTTACTCAAGGAAATACTAGGATTTAAAAAAAA   6840
```

FIGURE 24A

```
Full Length=263

5881  ATGTAGCATTTATGCATTTTTCTTAAGCGTCGATGGAGGAGTTTGTAAATGAAGTACAGT
                               KRAScony A1(ID : 13)

5941  TCATTACGATACACGTCTGCAGTCAACTGGAATTTTCATGATTGAATTTTGTAAGGTATT
                KRAScony A2(ID : 264)

6001  TTGAAATAATTTTTCATATAAAGGTGAGTTTGTATTAAAAGGTACTGGTGGAGTATTTGA

6061  TAGTGTATTAACCTTATGTGTGACATGTTCTAATATAGTCACATTTTCATTATTTTTATT

6121  ATAAG                      ATATAAACTTGTGGTAGTTGGAGCTGGTGGCGTAGG
                                 KRAS cony B1(ID : 11)
                                       Kras Inv mut Blocker (ID:265)
                          6151 - ACTTGTGGTAGTTGGAGCTGT
                                 Kras B1 cony G12V (ID : 9)
                          6186 -                     T
                          6186 -                     T
                          6186 -                     A
                          6186 -                     C
                          6185 -                     A
                          6185 -                     T
                          6189 -                         T 6181  CAAGAGTG            TTGACGATACAGCTAATTCAGAATCATTTTGTGGACGAATATGATCCAAC
                kras cony B2(ID : 273)

6241  AATAGAGGTAAATCTTGTTTTAATATGCATA                TTTGATACA

6301  GATAAAGGTTTCTCTGACCATTTTCATGAGTACTTATTACAAGATAATTATGCTGAAAGT

6361  TAAGTTATCTGAAATGTA                     TAACCATTAATATGGGAACTT

6421  TACTT               TCCATGATGTTCACTCTCTGTGCATTTTGATTGGA

6481  AGTGTATTTCAGAGTTTCGTGAGAGGGTAGAAATTTGTATCCTATCTGGACCTAAAAGAC
```

FIGURE 24B

Full length=198

```
6061 TAGTGTATTAACCTTATGTGTGACATGTTCTAATATAGTCACATTTTCATTATTTTTATT
              275
6121 ATAAGCCTGCTGAAAATGACTGAATATAAACTTGTGGTAGTTGGAGCTGGTGGCGTAGG
          >>>>>>>>>>>>>>>>>>>

6181 CAAGAGTGCCTTGACGATACAGCTAATTCAGAATCATTTTGTGGACGAATATGATCCAAC

6241 AATAGAGGTAAATCTTGTTTTAATATGCATATTACTGGTGCAGGACCATTCTTTGATACA

6301 GATAAAGGTTTCTCTGACCATTTTCATGAGTACTTATTACAAGATAATTATGCTGAAAGT
                199
6361 TAAGTTATCGAAATGTACCTTGGGTTTCAAGTTATATGTAACCATTAATATGGGAACTT
             Amo42
             TGAAATGTACCTTGGGTTTCA Amo43  265 bp
             TGAAATGTACCTTGGGTTTCAAG Amo44
              GAAATGTACCTTGGGTTTCAAGTT Amo45
              GAAATGTACCTTGGGTTTCAAG Amo46
         204
6421 TACTT█████████████TCCATGATGTTCACTCTCTGTGCATTTTGATTGGA
         Amo37
                205 ████████████ Amo38  332 bp
          206 ████████████ Amo39
              207 CAGTATGTCAGGTCCATGA Amo40
                                       208 TGTGCATTTGATTGGAAGTG Amo41
          209 ████████████ Amo47
          210 ████████████ Amo48
                 211 ████████████ Amo49
                                     212 TTCTGTGCATTTGATTGGA Amo51
         213
6481 AGTGTA█████████████TAGAAATTTGTATCCTATCTGGACCTAAAAGAC
         Amo50
           214 ████████████ Amo52  382 bp

6541 AATCTTTTTATTGTAACTTTTATTTTTATGGGTTTCTTGGTATTGTGACATCATATGTAA

6601 AGGTTAGATTTAATTGTACTAGTGAAATATAATTGTTTGATGGTTGATTTTTTTAAACTT

6661 CATCAGCAGTATTTTCCTATCTTCTTCTCAACATTAGAGAACCTACAACTACCGGATAAA

6721 TTTTACAAAATGAATTATTTGCCTAAGGTGTGGTTTATATAAAGGTACTATTACCAACTT

6781 TACCTTTGCTTTGTTGTCATTTTTAAATTTACTCAAGGAAATACTAGGATTTAAAAAAAA
```

FIGURE 24C

```
Full Length=161
 6001 TTGAAATAATTTTTCATATAAAGGTGAGTTTGTATTAAAAGGTACTGGTGGAGTATTTGA
 6061 TAGTGTATTAACCTTATGTGTGACATGTTCTAATATAGTCACATTTTCATTATTTTTATT
        162                                                      276
 6121 ATAAGGCCTGCTGAAAATGACTGAATATAAACTTGTGGTAGTTGGAGCTGGTGGCGTAGG
        Amo1
                       163 TGAATATAAACTTGTGGTAGTTGGA Amo10  51bp
                       164 GTGAATATAAACTTGTGGTAGTTGGA Amo11
                       165 TGAATATAAACTTGTGGTAGTTGGAG Amo12
                       166 CTGAATATAAACTTGTGGTAGTTGGAG Amo13
                       167 ACTGAATATAAACTTGTGGTAGTTGGA Amo14
                 168                           Amo15
                 169                           Amo16
                    170 TGACTGAATATAAACTTGTGG Amo17
                 171                           Amo18
                 172                           Amo19
                 173                           Amo20
              174                     Amo21
              175                     Amo22
                 176                  Amo23
              177                 Amo24
             178           Amo2
           179 AAGGCCTGCTGAAAATGACT Amo3
           180 GGCCTGCTGAAAATGACTGA Amo4
           181 GGCCTGCTGAAAATGACTG Amo5
          182 TAAGGCCTGCTGAAAATGACT Amo6
          183 TAAGGCCTGCTGAAAATGAC Amo7
         184 ATAAGGCCTGCTGAAAATGA Amo8
         185 ATAAGGCCTGCTGAAAATGAC Amo9
       186 ATTATAAGGCCTGCTGAAAATGA Amo25
      187 ATTATAAGGCCTGCTGAAAATGAC Amo26
      188 ATTATAAGGCCTGCTGAAAATG Amo27
      189 TATTATAAGGCCTGCTGAAAATGA Amo28
      190 ATTATAAGGCCTGCTGAAAA Amo29
           191 TTTTTATTATAAGGCCTGCTG Amo30
       192 CATTATTTTTATTATAAGGCCTGCTG Amo31
           193 ATTTTTATTATAAGGCCTGCTG Amo32
         194 TTATTTTATTATAAGGCCTGCTG Amo33
           195 TATTTTATTATAAGGCCTGCTG Amo34
     196 TCATTATTTTTATTATAAGGCCTGCTG Amo35  86 bp 6181 CAACAGTGCCTTGACGATACAGCTAATTCAGAATCATTTTGTGGACGAATATGATCCAAC
 6241 AATAGAGGTAAATCTTGTTTTAATATGCATATTACTGGTGCAGGACCATTCTTTGATACA
 6301 GATAAAGGTTTCTCTGACCATTTTCATGAGTACTTATTACAAGATAATTATGCTGAAAGT
```

FIGURE 24D

Full Length = 122
6061 TAGTGTATTAACCTTATGTGTGACATGTTCTAATATAGTCACATTTTCATTATTTTTATT
                                121                              123
6121 ATAAGGCCTGCTGAAAATGACTGAATATAAACTTGTGGTAGTTGCAGCTGGTGGCGTAG
                                  >>>>>>>>>>>>>>>>>>>>

6181 ████████████████████████AGCTAATTCAGAATCATTTGTGGACGAATATGATCCAAC
    Amo53 *50 bp*
124 ████████████████████████ Amo54
125 ████████████████████████ Amo55
126 ████████████████████████ Amo56
127 AGAGTGCCTTGACGATACAGCT Amo57
   128 CCTTGACGATACAGCTAATTCAGA Amo58 *62 bp*
   129 CCTTGACGATACAGCTAATTCAG Amo59
   130 CCTTGACGATACAGCTAATTCA Amo60
      131 TGACGATACAGCTAATTCAGAATCA Amo61
      132 CCTTGACGATACAGCTAATTCAGAA Amo62
         133 GCTAATTCAGAATCATTTGTGGA Amo63 *75 bp*
         134 GCTAATTCAGAATCATTTGTGG Amo64
         135 GCTAATTCAGAATCATTTGTGAC Amo65
         136 CAGCTAATTCAGAATCATTTGTG Amo66
         137 CAGCTAATTCAGAATCATTTGTGG Amo67
            138 GAATCATTTGTGGACGAATATGA Amo73
            139 GAATCATTTGTGGACGAATATG Amo74
               140 TTGTGGACGAATATGATCCAA Amo68
               141 TTTTGTGGACGAATATGATCCA Amo69
               142 TTGTGGACGAATATGATCCAAC Amo70
               143 TGTGGACGAATATGATCCAA Amo71
               144 TTGTGGACGAATATGATCCA Amo72
                  145 GTGGACGAATATGATCCAACAA Amo75
               146 TTGTGGACGAATATGATCCAAC Amo76
               147 TGTGGACGAATATGATCCAAC Amo77
               148 GTGGACGAATATGATCCAACA Amo78
               149 GTGGACGAATATGATCCAACAAT Amo79
                  150 ACGAATATGATCCAACAATAGAGG Amo80
                  151 CGAATATGATCCAACAATAGAGG Amo81
                  152 ACGAATATGATCCAACAATAGAGG Amo82
                  153 CGAATATGATCCAACAATAGAGGT Amo83
                  154 ACGAATATGATCCAACAATAGAGGT Amo84
                  155 Amo85 TGATCCAACAATAGAGGTAAATCTTG
                  156 ACGAATATGATCCAACAATAGAGGTAA Amo86
                  157 CGAATATGATCCAACAATAGAGGTA Amo87
                  158 ACGAATATGATCCAACAATAGAGGTA Amo88
                  277 Amo89 ATGATCCAACAATAGAGGTAAATCTT

6241 AATAGAGGTAAATCTTGTTTTAATATGCATATTACTGGTGCAGGACCATTCTTTGATACA

6301 GATAAAGGTTTCTCTGACCATTTTCATGAGTACTTATTACAAGATAATTATGCTGAAAGT

FIGURE 24E

ANALYTICAL METHODS FOR CELL FREE NUCLEIC ACIDS AND APPLICATIONS

SEQUENCE LISTING

The instant application contains a Sequence Listing which has been submitted electronically in ASCII format and is hereby incorporated by reference in its entirety. Said ASCII copy, created on Apr. 6, 2015, is named 065691-0597_SL.txt and is 85,454 bytes in size.

The present invention is directed to an in vitro method of detecting cell free nucleic acids, preferably cell free DNA (cfDNA) in a body fluid sample from an individual or a patient, wherein the method comprises the step of accurately and sensitively determining the concentration of cell free nucleic acid in the sample and/or determining the concentration or amount of said cell free nucleic acid of a size range and/or the index of integrity or size fraction ratio (SFR) of said cell free nucleic acid and/or the determination of the presence of genetic polymorphisms (such as known Single Nucleotide Polymorphisms (SNPs) or mutations). The invention encompasses also a method to discriminate body fluid individuals where cfDNA are highly released by comparing the size profile obtained for at least one of three size ranges of cfDNA. The invention also encompasses a method for analysing cell free nucleic acids in individuals for the diagnosis, prognosis or for assessing the evolution of a physiological state, such as the progression of a tumor or metastatic cancer, for monitoring the efficacy of a cancer treatment in a patient or for theragnostic purposes implementing the analysis of these biomarkers.

In the coming years, the detection of cell free (cf) nucleic acid, such as circulating DNA (cirDNA or "ct DNA"), could become a non-invasive breakthrough technology that will allow the diagnosis of a specific pathological or physiological state, the prognosis and the follow-up of cancer, the choice of therapeutic orientation for each individual patient and the mass screening as a complement to the existing tests. Cell free nucleic acids were proposed as biomarkers for various diseases (cancer, diabetis, Sickel Cell Disease, autoimmune diseases, myocardial infarction, Multiple Sclerosis, . . . ) and as well for particular physiological conditions such as (intense physical exercise, hemodialysis, pregnancy), or some clinical conditions (trauma, sun burn, sepsis, . . . ). They are previously two ways in the literature of using cf nucleic acids as biomarker: first by measuring their concentration and second by studying its nucleotidic sequence.

Cell free or extracellular nucleic acids (DNA or RNA) have been detected in many biological fluids, such as blood, urine, faeces, milk, bronchial lavage and ascite. It is believed that cfDNA found in other body fluids may mainly originate from circulating nucleic acids. Most of the study on cell free nucleic acids were performed by detecting and quantifying circulating DNA (DNA in blood).

Circulating DNA (DNA in blood, cirDNA) was initially found in plasma samples by Mandel and Metais (1) and a long time afterwards, was characterized in plasma samples of cancer patients by Stroun et al (2). The technical progress that has allowed the detection and quantification of specific RNAs or DNAs has made possible to diagnose and follow diseases. CirDNAs carry the genetic alterations associated with the development of some diseases (including cancer) and therefore for more than ten years they have been considered as a potential non-invasive diagnostic marker of different physiological (prenatal test, . . . ) or pathological (cancer, . . . ) states.

The detection of genetic alterations in cirDNA seems to be a particularly attractive diagnostic approach (3-5) but at that time limited to costly and time consuming invasive approaches such as DNA sequencing from tumor section. As mutant genes are not only markers of cancer but also the causes, at least partially, of tumour growth, they present advantages in comparison to conventional non invasive markers such as faecal blood or serum PSA. Particularly, conventional markers are not involved in a pathogenic way in the process of tumorigenesis and are less specific for the neoplasia than mutations. The genetic analysis of cirDNA in blood samples will be easy to put in place and might potentially detect different cancers in an early and very sensitive way. Colorectal cancer remains a major problem of public health that has not been solved yet. Only an early screening of the patients at risk (age, heredity, way of life and chronic inflammatory diseases of the colon are the main quoted risk factors) remains one of the safest ways to prevent this disease (6, 7). Therefore, in France, like in most of the industrialized countries, the search for the best mass screening strategy of colorectal cancer is a public health priority. Only one test is at the moment used for the mass screening of colorectal cancer in subjects older than 50 years: the Hemoccult II® test. However, Hemoccult II® appears to be of low sensitivity and shows an important rate of false positives and false negatives. A second-line test is colonoscopy which shows a very high sensitivity and specificity and a low, but significant, rate of false negatives. However, this test is invasive and can lead to severe complications (haemorrhage 1/300, perforation 1/800).

It is known that cell-free DNA levels in plasma of colorectal cancer (CRC) patients are significantly higher in patients with CRC compared to healthy patient, decrease progressively in the follow-up period in tumor-free patients, and increase in patients with recurrence or metastasis (22). Thus CRC patient represent a useful model of physiological or pathological conditions resulting or leading to a large cell-free DNA release.

The mechanisms of release of cfDNA are very poorly known, but it has been suggested that necrosis, apoptosis, phagocytosis or active release might be implicated. Tumour development is associated with necrosis of certain parts of the tumour but also of the adjacent, non-tumour tissues. On the other hand, the body defence mechanisms lead to the destruction of cancer cells by phagocytosis or apoptosis. Concerning cirDNA, it has been established that necrosis and phagocytosis lead to DNA degradation down to sizes rarely smaller than 1000 bp (5, 7, 9). In case of apoptosis the region between nucleosomes can be degraded and this leads to the release in the circulation of DNA of the size of 180-200 bp (the size of one nucleosome plus linker) or multiples of that (7).

Many studies have been started in order to identify abnormal forms of DNA in plasma or serum (4, 7). At the moment, there are contradictory results although very high rates of cancer detection have been reported in such a way. These studies, although promising, have led to many questions about the confidence (or: the reliability) of using abnormal cirDNA as a biomarker of cancer (4, 7). Particularly, it is imperative to develop technologies that can detect the number of mutant DNAs and the specific detection of mutation(s) in the same sample. In the case of colorectal cancer, many mutations have been identified and it is now possible to define the sequence of appearance of such mutations; indeed, it seems that the APC gene, then KRAS (and BRAF), then p53 are, among others, the targets of mutations that lead from normal epithelium to adenoma, then to dysplasia and finally to metastatic carcinoma (8-11). It is undeniable to think that this approach will be in the future an efficient diagnostic method. However, at the moment, the tests to detect gene mutation(s) are not sufficiently specific either for diagnostic, theragnostic or prognostic use. Currently, there is no specific test or developed analysis for the detection of free cell nucleic acid, such as cirDNAs. The technology of Quantitative Polymerase Chain Reaction (Q-PCR) is the method of choice for the detection and quantification of genetic variations or mutations. SNPs (Single Nucleotide Polymorphisms) are among the most frequent mutations; they might allow differentiating subjects and can be responsible of tumour progression in many cancers. They correspond to the modification of a single nucleotide thus making difficult the discrimination between the sequence carrying the point mutation and the non-mutated sequence. Consequently, their detection and even more their quantification by Q-PCR are of low specificity and sensitivity.

Current cancer therapies are focused on the patient's illness rather than targeted to individual patients. However, inter-individual differences in drug disposition or pharmokinetics have led to heterogeneity in patient responses to traditional cancer chemotherapy. There remains a need for theragnostic methods capable of rendering cancer therapies that are more accurate, efficacious, and safe for individual patients. In addition, detection of mutations or specific genetic tag (such as polymorphisms) can help in evaluating individual response to numerous therapies such as antibody therapy, cytostatic therapy or antibody dependant cell-mediated cytotoxicity.

Precise cirDNA size profiling was ascertained in only two publications:

The team of D. Lo is one of the two top leading teams in the field and has analyzed the size distributions of maternal and fetal DNA in maternal plasma by using Q-PCR assay and primer set design for amplifying sequence from 105 to 798 bp (16). They suggested that "most of the cirDNA molecules were in the range of 145-201 bp" (which is approximately 1e nucleosome size). In regards to this invention authors did not study or neither discuss on the possibility of existing cirDNA of size below 105 bp.

CirDNA size profile was very recently (January 2010) studied by using a highly performant method: the microfluidic single molecule spectroscopy (20). Although size profile shape of cirDNA extracted from stages I and IV lung cancer patient sera is somewhat similar to our results, they concluded that "the greatest distinguishing power occurred at a threshold of 800 bp". In regards to this invention authors never mention or discuss about ctDNA of size below 320 arguing that "below 320 bp the two curves appear similar".

Before this invention it was not obvious at all that amplicon size <100 bp is better as compared what it was conventionally established. Since it was previously established that shortest cirDNA molecules lengths should theoretically be >180 bp (size of a nucleosome) and since PCR efficiency is conventionally (with use of genomic DNA) optimal when amplifying sequence of 150-300 bp range, all the previously described reports showed the use of detection of amplicon of size circa 150 bp when analysing cfDNA. Q-PCR assay was often used as cell free nucleic acids study in the literature. Primer set design was mostly set upon their efficiency in amplifying a targeted nucleic acids region, and sometimes to match with the fact that some reports suggested the high proportion of mononucleosome in cell free nucleic acids (amplification of 100-180 bp nucleic acids region as compared to the 150-300 bp conventionally used range such as for genomic DNA analysis). Among the large literature only a couple of reports described the use of detecting amplified fragments <100 bp solely based on technical aspects linked to primer design and/or specific targeted gene region, but never on the assumption that higher proportion of cirDNA of size <100 bp were present in a particular physiological condition nor pathology.

For instance, Ellinger et al (BJU International, 2009, V. 104, 5, 48-52) use a PCR primer system amplifying a 79 bp and a 230 bp region of mitochondrial ctDNA in purpose of determining an integrity index by comparing quantification using PCR system amplifying DNA region of a size shorter and greater size than the size of a mono-nucleosome (180-200 bp). They indicate that the 79 bp primer pair amplified a 79 bp fragment that corresponds to total mtDNA and includes DNA truncated by apoptosis.

Similarly, the same group (Ellinger et al., 2009, V. 181, 1, 363-371) quantified a 106, a 193 and a 384 bp ATCB amplicon from ctDNA extracts and obtained similar DNA levels using the primer sets ACTB-106 and 193.

Board et al (Annals of the New York academy of Sciences, 2008, 98-107) quantified by Q-PCR a 77, a 272 and a 512 bp amplicon from ctDNA extracts in the same purpose than Ellinger et al. In.

Koide et al (Prenatal Diagnosis, 2005, V. 25, 604-607) quantified a 63, a 107, a 137, a 193, a 313, a 392 and a 524 bp amplicon of the SYR gene of cell free circulating fetal DNA in maternal plasma to study the degradation from storage and freezing by examining further fragmentation of said ctDNA.

DNA is a nucleotide chain and the modification or alteration of one or more nucleotides (genetic plymorphisms) in the sequence of a gene can change the message of that gene and lead to a modified or inactive protein. Genetic mutations are the cause or a risk factor in many pathologies and their detection seems to be more and more an efficient way to diagnose, follow and better orient the therapeutic choice for a patient. The technology of Quantitative Polymerase Chain Reaction (Q-PCR) is the method of choice for the detection and quantification of genetic mutations. Point mutations (Single Nucleotide Polymorphisms or SNPs) correspond to the modification of a single nucleotide on one of the two alleles and more rarely on both alleles. This, among other reasons (inherent non-specificity of the Q-PCR technology), leads to a low specificity of Q-PCR for discriminating between sequences with point mutations and the non-mutated sequences that are called <<wild type>> (WT). On the other hand, the detection of somatic point mutations (that do not interest the reproductive cells, the gametes, and thus are not heritable) should be very sensitive particularly in the case of circulating DNA because it has been established that only 0.1 to 10% of circulating DNA of an individual with cancer carries the mutation (7). It is for this reason that many modifications of the Q-PCR technology have been described, such as ARMS-PCR, TaqMAMA and FLAG-PCR. These technologies require the use of modified bases, specific enzymes or additional procedures in addition to the reagents.

At the moment, there is no specific test or developed analysis for the detection of cell free nucleic acids, and particularly for detecting mutations such as mutations associated with cancer pathology or with resistance to cancer treatment.

In particular, there is a need to provide a method for the detection of gene mutations such as the ones in the KRAS gene using a blood sample. Indeed, colorectal cancer is one of the major cause of cancer and common cause of death from cancer in Europe. In this cancer, targeted therapy has appeared the last past few years with antibodies to epidermal growth factor receptor (EGFR) but numerous studies have shown the benefit of these antibodies limited to patients with wild-type KRAS gene only. These findings represent an important step forward in the field of personalized medicine by theragnostic method which can determinate the optimal treatment for each patient in order to avoid overtreatment with drugs that have potentially toxic adverse effects but little benefit.

The detection of cell free nucleic acids has been a frequent topic in the literature now for more than 10 years. However, partially due to the clinical origin of the analysed samples, the origin and form of cell free nucleic acids have been rarely studied systematically.

The authors demonstrated that nucleic fragment size is of crucial importance when analysing cell free nucleic acid and in particular when determining their concentration. They proved that specific detection of mutation by measuring cfDNA concentration is possible in one step by comparing concentration determined by targeting a short (<100 bp) mutated fragment and non-mutated fragment of similar size when both fragment size are <100 bp and of a similar size (+/−10%).

This way of identifying the presence or not of a gene mutation is very convenient because it is very fast and not very expensive. Moreover, it allows dispensing with sophisticated techniques like sequencing. On the other hand, sequencing leads to an answer without possible doubts (but for contamination or handling mistakes).

Cell free DNA in a cancer patient is constituted of DNA of tumour and non-tumour origin. Very little is known about the respective contribution of these two types of cell free DNA during tumour progression. IntPlex should allow advancing on this issue and this information will bring valuable diagnostic and/or prognostic benefits. Indeed, the quantity of mutated, and thus of tumour DNA, can be linked by this method directly to the quantity of non-tumour DNA. The calculation of this percentage can be correlated both with the total quantity of released cirDNA and with the progression or regression of the tumour.

The cirDNA integrity index has been linked to the concentration of mononucleosomes (180-200 bp), i.e., to the estimate of the apoptosis rate. Very few works have described how to calculate the integrity index and usually in a not very rigorous way. This has led to contradictory results concerning the study of its changes during tumor progression (13-19). Moreover, the term integrity seems to be inappropriate if one takes into consideration the fact that very little or no genomic DNA circulates in the blood. If the data of the previously quoted works are contradictory and confusing on the clinical use of the integrity index it is because they did not take into account the possibility that a big proportion of cirDNA is <100 bp.

The inventors, for the first time, have demonstrated the presence of a higher proportion of cirDNA of a size <100 bp that is directly correlated with the increase of the concentration of cirDNA, particularly in samples from cancer patients. The inventors have measured the integrity index by measuring cfDNA concentration with detecting 2 amplified fragments: a short of <100 bp and a long ranging of 250-400 bp. They have demonstrated that it allowed a more specific and sensitive discrimination between cirDNAs of healthy individuals and cancer patients. Then identification of some pathologies (such as cancer) or a specific physiological state (such as intense effort) may be allowed by means here discovered. This was never observed or anticipated before.

By focusing particularly on the study of the size of cell free nucleic acids in order to optimize their measurement and especially the specificity and sensitivity of their detection by Q-PCR, the inventors have developed by means of examples new optimal way(s) or method(s) first for quantifying cell free nucleic acids in body fluid sample, secondly of analysis of genetic polymorphisms, such as mutation of the KRAS and BRAF genes, in cell free nucleic acids. Third, the inventors have developed an integrated test which combines as well the estimation of the cell free nucleic acids fragmentation rate (also named "index of integrity" or "apoptosis rate" in the present description) as a third bio-marker. Such a detection/quantification of cell free nucleic acids can be a breakthrough technology for the years to come as a non-invasive test that allows the diagnosis, theragnostic, prognosis, follow-up of a disease, and the mass screening as a complement to currently available tests.

The Examples below strongly support the interest of measuring such cell free nucleic acids by the methods of the present invention as an innovative tool in various preclinical and clinical investigations.

The inventors propose here to use the technique of quantitative PCR in a one "step" analytical procedure that is specific for the analysis of cell free nucleic acids and leads to a simple, robust, highly sensitive and selective detection/quantification which is compatible with a standardized procedure which could be exploited industrially. It was earlier known that cell free nucleic acids are strongly fragmented down to sizes to 180 bp which correspond generally to the length of the sequences amplified by the primers that are usually chosen when optimally using PCR (between 100 and 300 bp). Thus, differently from the analysis of genomic DNA in which the concentration of quantified DNA is directly proportional to the number of amplified copies (of genome), the quantity of circulating DNA determined by Q-PCR is not proportional to the number of copies. Our method takes into account the specificity of size and form of circulating DNA. This allows the precise and direct comparison of the concentration of two different sequences and also the calculation of the percentage of a sequence relative to another. By determining the size profile of cell free nucleic acids present in body fluid sample, the inventors have demonstrated that it is possible to discriminate healthy individuals to individuals exhibiting high level of cfDNA.

Surprisingly, the inventors have demonstrated by using a single-step Q-PCR method, it is possible to determine simultaneously three important bio-markers for the follow up and treatment of cancer: (1) the specific quantity of cell free nucleic acids; (2) the presence of a genetic polymorphism (such as a SNP or a mutation); and (3) the apoptosis rate (also named "integrity index" or "fragmentation rate").

The method of the present invention presents particularly the following advantages:

Decreases significantly the time needed for the analysis particularly in comparison to the analysis of a tumor biopsy (no need of the intervention of the anatomo-pathology service, . . . ).

Makes easier the sampling and handling of the biological sample.

Allows the non-invasive analysis of non-accessible tumors.

Adds two non-negligible clinical parameters, i.e., the quantity of cell free nucleic acids and the apoptosis rate (fragmentation index or index of integrity), the value of which seems to be directly linked to the tumor growth.

The application field of the present invention concerns all utilizations of the detection of cell free nucleic acids such as, but non limited to:
analysis of parental genes,
clinical gene analysis (pathologies such as cancer, . . . ),
theragnostics, a treatment strategy that allows to orient the therapy in function of a diagnostic marker (i.e. the mutational status of one or several genes),
analysis of ethnic origins,
determination of the sex in foetal cirDNA,
evolution of a particular physiological state.

As discussed above, there are numerous discrepancies about ctDNA size pattern in the literature as formerly mentioned Ellinger et al. The few recent reports studying ctDNA and describing that ctDNA is mainly of low size always indicate that lower size is around the mononucleosome size. This is based on the various and numerous gel electrophoresis analysis which clearly showed an intense band of around 180 bp and a lower of around 360 bp and sometimes a smear at higher size while below 180 bp absolutely no band appears.

Our data on ctDNA size pattern as presented in this invention description clearly disagree with that conclusion. Being confident with our conclusion we demonstrate in the example VIII that a significant amount of DNA is present in the gel at size below 180 bp.

As a consequence and as demonstrated by the examples below, ctDNA can mainly be of a size lower than 180 bp, and in particular lower than 100 bp.

According to the present invention, the inventors propose:
to determine the quantity or concentration of ctDNA of size lower than 100 bp as an essential parameter of ctDNA analysis
compare amount of ctDNA from the fraction comprising ctDNA of size lower than 100 bp to the fraction of size between 150 to 400 bp or to the fraction of size higher than 300 or 400 bp.

Thus, in a first aspect, the present invention is directed to a method of quantifying cell free nucleic acids in a body fluid sample, comprising:
a) identifying a subject of interest;
b) obtaining a body fluid from said subject;
c) determining the concentration or amount of said cell free nucleic acid in said body fluid sample, wherein said nucleic acid is in a short size range nucleic acid and has a length inferior to 100 bp, preferably comprised between 40 and 99 bp.

By "circa" it is intended here to mean±10% of the defined value.

In a preferred embodiment, the method of the invention is carried out to determine the concentration/amount of cf nucleic acid size inferior to 100 bp.

In a preferred embodiment, the step c) is carried out by a method implementing the PCR method and wherein the amount/concentration of cf nucleic acid of size <100 bp is determined by employing a primer set amplifying a DNA region <100 bp, preferably <80 bp.

In a preferred embodiment, in step c) the amount/concentration cf nucleic acid size fractions <100 bp is determined by calculating the difference of those determined by employing 2 sets of primer pairs detecting amplicons of different size, one of the two or both being <100 bp.

In another aspect, the present invention is directed to a method for calculating a cf nucleic acid index of fragmentation by comparing the concentration/amount of size fractions obtained by a method of quantifying cell free nucleic acids in a body fluid according to the invention.

In a preferred embodiment, the present invention is directed to a method for determining the specific size profile of cell free nucleic acids in a body fluid sample, comprising:
a) identifying a subject of interest;
b) obtaining a body fluid from said subject;
c) determining the specific size profile of said cell free nucleic acid in said body fluid sample by:
determining at least the concentration or amount of short nucleic acids having a length inferior to 100 bp, preferably comprised between 40 and 99 bp, and
determining at least the concentration or amount of long nucleic acids having a length superior to 100 bp, preferably comprised between 145 bp and 450 bp, or a fraction (ratio) of cfDNA of a specific size range.

By "determining a fraction (ratio) of cfDNA of a specific size range", it is intended to designate the determination of the ratio between the concentration or amount of cell free nucleic acids having for example a length inferior to 100 bp, preferably comprised between 40 and 99 bp, and the concentration or amount of cell free nucleic acids having a length superior to 100 bp, preferably comprised between 145 bp and 450 bp, or the inverse ratio.

More preferably, said cell free nucleic acids which are desired to be quantified by the method of the present invention is a cf nucleic from autosome (or derived from autosome).

By cell free nucleic acids from autosome, it is intended to designate cf nucleic acid not coming or derived from sexual chromosomes.

In a preferred embodiment, the present invention is directed to a method of quantifying cell free nucleic acids in a body fluid sample, comprising:
a) identifying a subject of interest;
b) obtaining a body fluid from said subject;
c) determining the concentration or amount of said cell free nucleic acid in said body fluid sample by:
determining the concentration or amount of short nucleic acid having a length inferior to 100 bp, preferably comprised between 40 and 99 bp, and/or, preferably and,
determining the concentration or amount of a long nucleic acid having a length comprised between 145 bp and 450 bp.

The inventors have demonstrated that the cell free nucleic acid ("cf NA") size profile is specific when cf NA, particularly circulating DNA ("ct DNA") is released at level higher than the normal level being in higher proportion at length inferior to 100 bp and in much lower proportion at length range of 250-400 bp, these characteristics forming part of the present invention.

In a preferred embodiment, said cell free nucleic acid is selected from the group consisting of cell free DNA (cfDNA), cell free RNA, cell free siRNA or cell free miRNA.

In the present invention, the wording "apoptosis rate", "DNA fragmentation index" and "index of integrity" have the same meaning; DNA fragmentation level being the inverse of the index of integrity level.

In a preferred embodiment of the method of the present invention, said cell free nucleic acids are circulating nucleic acids.

When the present invention is directed to a method of quantifying cell free nucleic acids in a body fluid sample according to the present invention and comprising the two steps of:
c)i) determining the concentration or amount of short nucleic acid having a length inferior to 100 bp, preferably comprised between 40 and 99 bp; and c)ii) determining the concentration or amount of long nucleic acid having a length comprised between 145 bp and 450 bp, it is preferred that said long cell free nucleic acid partially or fully comprises said short cell free nucleic acid.

In another aspect, the invention encompasses a method for determining the index of integrity of cell free nucleic acid a body fluid sample, said method comprising:
a) identifying a subject of interest;
b) obtaining a body fluid from said subject;
c) determining the index of integrity of cell free nucleic acid in said body fluid sample,
wherein said index of integrity is calculated as the ratio of the concentration or the amount of cell free nucleic acid of a "long" size range and of a "short" size range, said concentrations being determined by the method of quantifying cell free nucleic acid in a body fluid sample according to the present invention,
wherein said nucleic acid short size range has a length inferior to 100 bp, and wherein said long size range being comprised between 180 bp and 450 bp.

DNA Integrity Index (DII)/DNA Size Fraction Ratio (SFR)

According to the present invention, the inventors want to provide with a new DNA Integrity index calculation which takes account for the first time of the amount of ctDNA size lower than 100 bp. The inventors want also to provide for the first time with the calculation of a DNA Size Fraction Ratio (SFR) which further includes in its calculation the ratio of the amount of ctDNA having a specific size range, such as between 200 and 450 to the amount of ctDNA size between 60 bp and 100 bp or 43 and 100 bp. Integrity index (corresponding to the amount of cf nucleic acid higher than a long length to the amount of cf nucleic acid higher than a shorter length) and SFR (corresponding to the ratio of two size fractions) are both nucleic acid fragmentation indexes.

Thus calculation of integrity index can be done by determining a ratio of the amount of ctDNA size higher or lower than a specific size, or comprised in a specific range of sizes, to the amount of ctDNA size higher or lower than another specific size, or comprised in another specific range of sizes or to the total ctDNA. For instance by determining a ratio of the amount of ctDNA size higher than 180-200 bp to the amount of ctDNA size as much as possible lower than 100 bp.

By determining the ratio of quantities determined by using detection of an amplicon of 300 bp and of 60 bp may account of this notion as the value obtained corresponds to the % of the amount of ctDNA higher than 300 bp from the amount of ctDNA higher than 60 bp.

In the present invention, by DNA Integrity index (DII), it is intended to designate the new DNA Integrity index calculation which takes account of the amount of ctDNA size lower than 100 bp.

In examples XI to XV below, the inventors have determined this new DNA Integrity index calculation or DNA Size Fraction Ratio (SFR) by calculating the ratio of the amount of ctDNA size higher than 200 to the amount of ctDNA size between 60 bp and 100 bp or 43 and 100 bp. This new calculation determining the amount of ctDNA of size as much as possible lower than 100 bp allow to more precisely estimate ctDNA fragmentation level, which is more accurate in particular for distinguishing cancer patient plasma to healthy individuals.

Such new DNA Integrity index calculation or DNA Size Fraction Ratio (SFR) calculation can be carried out in the present invention by a method non-implementing the polymerase chain reaction (PCR) such as capillary zone electrophoresis, chip-based capillary electrophoresis or mass spectroscopy or by a method implementing the polymerase chain reaction (PCR) such as quantitative real-time polymerase chain reaction (Q-PCR) method.

When the PCR such as Q-PCR, is implemented, detecting an amplicon having X bp corresponds in fact to quantify all the ctDNA fragments having a size superior or egal to X bp.

In a similar way, when the PCR such as Q-PCR, is implemented, detecting an amplicon having X by corresponds in fact to quantify all the ctDNA fragments having a size superior or egal to X bp.

When the Q-PCR is implemented, detecting an amplicon having a size inferior to 100 bp corresponds in fact to quantify all the ctDNA fragments having a size superior or egal to this size. Consequently these amplicons having a size inferior to 100 bp have to be taken account in the total ctDNA quantification.

For instance, when the Q-PCR is implemented, detecting an amplicon having a size egal to 60 bp corresponds in fact to quantify all the ctDNA fragments having a size superior or egal to 60 bp, corresponding to the maximal concentration/quantification of ctDNA.

In another aspect the present invention is directed to a method for determining tsaid DNA Size Fraction Ratio (SFR) of cell free nucleic acid in a body fluid sample, said method comprising:
a) identifying a subject of interest;
b) obtaining a body fluid from said subject;
c) determining the Size Fraction Ratio (SFR) of cell free nucleic acid,
wherein said SFR is calculated as the ratio of the amount of ctDNA having a specific size or range of specific sizes to the amount of ctDNA having another specific size or rang or specific sizes.

In another aspect the present invention is directed to a method for determining the said DNA integrity index (DII) new calculation or DNA Size Fraction Ratio (SFR) of cell free nucleic acid in a body fluid sample, said method comprising:
a) identifying a subject of interest;
b) obtaining a body fluid from said subject;
c) determining the DII or Size Fraction Ratio (SFR) of cell free nucleic acid,
wherein said DII or SFR is calculated as the ratio of the amount of ctDNA size higher than 200 to the amount of ctDNA size between 60 bp and 100 bp or 43 and 100 bp or 60-145 bp.

In a preferred embodiment of the method for determining the index of integrity of cell free nucleic acid or SFR in a body fluid sample of the present invention, said long size range cell free nucleic acid partially or fully comprises said short size range cell free nucleic acid.

In a preferred embodiment of the method for determining the index of integrity or SFR of the present invention, said long size range being comprised between 250 bp and 350 bp and said short size range being comprised between 50 bp and 99 bp.

In a preferred embodiment of the method of the present invention, the concentration of cell free nucleic acid or the index of integrity or SFR of cell free nucleic acid is determined by a method non-implementing the polymerase chain reaction (PCR) such as capillary zone electrophoresis, chip-based capillary electrophoresis or mass spectroscopy.

Such methods are well known from the skilled person (see for example "Comparisons between capillary zone electrophoresis and real-time PCR for quantification of circulating DNA levels in human sera", Fuming Sang et al., Journal of Chromatography B Volume 838, Issue 2, 11 Jul. 2006, Pages 122-128; "Prenatal diagnosis of thalassemia by chip-based capillary electrophoresis", Hua Hu et al., Prenatal Diagnosis, Volume 28 Issue 3, Pages 222-229, 2008).

In a more preferred embodiment of the method of the present invention, the concentration of cell free nucleic acid or the index of integrity or SFR of cell free nucleic acid is determined by a method implementing the polymerase chain reaction (PCR).

In this more preferred embodiment, the PCR method is selected from the group consisting of the quantitative real-time polymerase chain reaction (Q-PCR) method.

PCR or Q-PCR methods are standard methods well known from the skilled person.

Among particular PCR or Q-PCR methods, the "allele specific PCR" method, the "allele specific Q-PCR" method or the "allele specific Q-PCR using blocker oligonucleotides" method can be particularly cited.

Thus, when the concentration of cell free nucleic acid is determined by a method implementing the polymerase chain reaction (PCR), the present invention is also directed to a method of quantifying cell free nucleic acids in a body fluid sample, comprising:
a) identifying a subject of interest;
b) obtaining a body fluid from said subject;
c)—determining the concentration of amplified short fragment from cell free nucleic acid in said body fluid sample, wherein said nucleic acid short fragment has a length inferior to 100 bp, preferably comprised between 40 and 99 bp, and/or
determining the concentration or amount of amplified long fragment from cell free nucleic acid in said body fluid sample, wherein said long fragment has a length superior or equal to 100 bp, preferably comprised between 145 bp and 450 bp.

In a preferred embodiment, said step c) is a step of:
c) determining the amount of cell free nucleic acid in said body fluid sample, by subtracting the value resulting from the amplification of a fragment >100 bp from that of a fragment <100 bp, preferably of a fragment of 100-145 bp range from that of a fragment of 60-99 bp range.

More preferably, said amplified short fragment from cell free nucleic acid has a length comprised between 55 and 65 bp, circa 60 bp (60 bp±6 bp) being the most preferred.

When the present invention is directed to a method of quantifying cell free nucleic acids in a body fluid sample according to the present invention by a method implementing the polymerase chain reaction (PCR), and comprising the two steps of:
c)i) determining the concentration or amount of amplified short fragment; and
c)ii) determining the concentration or amount of amplified long fragment, it is preferred that said amplified long fragment partially or fully comprises the short fragment.

In a same aspect, when the index of integrity or SFR of cell free nucleic acid is determined by a method implementing the polymerase chain reaction (PCR), the present invention is also directed to a method for determining the index of integrity of cell free nucleic acid a body fluid sample, said method comprising:
a) identifying a subject of interest;
b) obtaining a body fluid from said subject;
c) determining the index of integrity or SFR of cell free nucleic acid in said body fluid sample,
wherein said index of integrity or SFR is calculated as the ratio of the concentration of amplified long fragment and amplified short fragment from said cell free nucleic acid, wherein said short fragment has a length inferior to 100 bp, and wherein said amplified long fragment being comprised between 180 bp and 450 bp.

In a preferred embodiment of the method for determining the index of integrity or SFR of the present invention implementing the polymerase chain reaction PCR, said amplified long fragment being comprised between 250 bp and 350 bp and said amplified short fragment being comprised between 50 bp and 99 bp.

In a preferred embodiment of the method according to the present invention for determining the index of integrity or SFR of cell free nucleic acid in a body fluid sample, said amplified long fragment partially or fully comprises the short fragment.

In a more preferred embodiment of the method for determining the index of integrity or SFR of the present invention, said amplified long fragment fully or partially comprises said short fragment.

In another aspect, the present invention encompasses a method for the detection of a genetic polymorphism, such as mutation or SNP, wherein said method comprises the steps of:
a) identifying a subject of interest;
b) obtaining a body fluid from said subject;
c) determining the concentration of amplified short fragment from cell free nucleic acid in said body fluid sample, wherein said cell free nucleic acid short fragment which is amplified contains said genetic polymorphism to be detected, and wherein said amplified acid short fragment has a length inferior to 100 bp, preferably comprised between 40 and 99 bp. More preferably said amplified short fragment containing said genetic polymorphism to be detected has a length comprised between 55 and 65 bp, circa 60 bp being the most preferred.

In a preferred embodiment, the present invention is directed to a method for the qualitative detection of the presence of a genetic polymorphism on a free cell nucleic acid, said method comprising the steps of:
a) determining the concentration or amount of cell free nucleic acids in a body fluid sample; b) determining the qualitative detection of the presence of genetic polymorphism by integrating the following parameters and the following step:
A1A2 in one hand and B1B2 in another hand are the representation of two short sequences;
given the sequence length of A1A2 and B1B2 ranging between 50 to 100 bp, and being different in length from +/−20%;
either A1A2 or B1B2 comprising the genetic polymorphism;
given CB1B2 and CA1A2 respectively the measured initial concentration of corresponding extracted nucleic acid by detecting the short fragment B1B2, and the short fragment A1A2, respectively,
i) calculating the % CB1B2/CA1A2, where B1B2 is defined as the sequence containing the genetic polymorphism; or
ii) calculating the % CA1A2/CB1B2 where A1A2 is defined as the sequence containing the genetic polymorphism,
optionally, the determination that % CB1B2/CA1A2 or % CA1A2/CB1B2 is higher than a specific threshold being significant of the qualitative detection of the presence of genetic polymorphism.

Preferably, in step ii), and sames %'s being the quantitative detection of mutated cf nucleic acid fragments.

In a preferred embodiment, the present invention is directed to a method for the qualitative detection of the presence of a genetic polymorphism on a free cell nucleic acid, said method comprising the steps of:
a) determining the concentration or amount of cell free nucleic acids in a body fluid sample by a method of quantifying cell free nucleic acids according to the present invention and wherein the concentration or amount of cell free nucleic acids is determined by a method implementing PCR;
b) determining the qualitative detection of the presence of genetic polymorphism by integrating the following parameters and the following step:
A1A2 in one hand and B1B2 in another hand are the representation of two short amplified sequences;
given the sequence length of A1A2 and B1B2 ranging between 50 to 100 bp, and being different in length from +/−20%;
either A1A2 or B1B2 comprising the genetic polymorphism;
given CB1B2 and CA1A2 respectively the measured initial concentration of corresponding extracted nucleic acid by detecting the amplified short fragment B1B2, and the amplified short fragment A1A2, respectively,
i) calculating the % CB1B2/CA1A2, where B1B2 is defined as the amplicon sequence containing the genetic polymorphism; or
ii) calculating the % CA1A2/CB1B2 where A1A2 is defined as the amplicon sequence containing the genetic polymorphism,
optionally, the determination that % CB1B2/CA1A2 or % CA1A2/CB1B2 is higher than a specific threshold being significant of the qualitative detection of the presence of genetic polymorphism.

Preferably, in step ii), and sames %'s being the quantitative detection of mutated cf nucleic acid fragments.

In a preferred embodiment, the positivity threshold is determined for each mutation using a convenient number of known samples, more preferably the positivity threshold is at least 2%, 5%, 7%, 8%, 9%, 10%, 12.5%, 15%.

Also forms part of the present invention a method for the qualitative detection of the presence of a genetic polymorphism on a free cell nucleic acid according to the invention and wherein nucleic acid corresponding with the genetic polymorphism of interest on the coding strand is located and the 3'-end extremity of the primer starting at position B1 or A2, and wherein the method implementing PCR is an allele specific PCR.

In a preferred embodiment, said genetic polymorphism to be detected is an inherited genetic polymorphism or a somatic genetic polymorphism.

By genetic polymorphisms, it is intended to designate particularly, but not to limit to:
genetic polymorphisms able to discriminate individual or ethnic population,
genetic polymorphisms in non coding region having an impact in a biological function,
genetic polymorphisms due to post transcriptional modification such as RNA editing or
genetic polymorphisms in coding region such as a mutation implying modification of the protein sequence.

Among these genetic polymorphism, are preferred the genetic polymorphism of a nucleic acid selected from the group consisting of genetic polymorphism associated with a pathology or a physiological state, or specific genetic polymorphisms in the nucleic acid, particularly in exonic, intronic or in non-coding regions of the nucleic acid sequence.

Is also encompassed by the present invention a method preferably implementing the PCR, particularly the Q-PCR, for the detection genetic polymorphism in said cell free nucleic acid in a body fluid sample and for determining the index of integrity or SFR of cell free nucleic acid, said method comprising the step of:
implementing the method for the detection of a genetic polymorphism according to the present invention in said cell free nucleic; and
implementing the method according to the present invention for determining the index of integrity of said cell free nucleic acid.

In a preferred embodiment, said method comprises the step of implementing the method of the invention for determining the index of integrity or SFR of cell free nucleic acid in a body fluid sample,
wherein in said method:
said amplified long fragment comprises a short non-mutated fragment and the short mutated fragment containing said genetic polymorphism (such as a SNP or a mutation) to be detected; and
said amplified long fragment being comprised between 250 bp and 350 bp and said amplified short fragments being inferior to 100 bp and preferentially comprised between 50 bp and 99 bp.

More preferably, said amplified mutated and non-mutated fragment have a length comprised between 55 and 65 bp, circa 60 bp being the most preferred.

More preferably, in the method for determining the index of integrity or SFR of cell free nucleic acid in a body fluid sample, said amplified long fragment partially or fully comprises two short fragments, one of the short amplified fragment containing a genetic polymorphism.

By partially comprising a fragment, it is intended to designate herein that the long fragment contains at least 10 consecutive bp, more preferably 15, 20, 25, 30, 35 or 40 consecutive by of the referenced short fragment.

In an also preferred embodiment of the method of the present invention, the concentration of said cf nucleic acid fragment of said cell free nucleic is calculated for an mutated cf nucleic acid fragment and/or an non-mutated cf nucleic acid fragment.

By mutated fragment and non-mutated fragment, it is intended to designate herein a fragment exhibiting and not exhibiting respectively the genetic polymorphism which is desired to detect in the method of the present invention.

In a preferred embodiment of said above method of the invention, the ratio of the concentration of long fragments and short fragments is calculated for the mutated short fragments and/or an non-mutated short fragments.

In a particular embodiment, the method of the present invention further comprising a step of determining the concentration of cell free nucleic acid fragments presenting a specific genetic polymorphism, said fragments exhibiting the genetic polymorphism having a defined length and wherein said concentration is compared to the concentration of a non-mutated fragments, said non-mutated fragments having circa the same length of the mutated fragments, preferably the length mutated or non mutated amplified fragments can be similar in length + or −20%.

In an also preferred embodiment of the method for the detection of a specific genetic polymorphism of the present invention, said method further comprises:
a step of determining the concentration in the cell free nucleic acid extract of non-mutated fragment and mutated fragment; and
calculating the percentage of the amount of short mutated fragments relative to the short non-mutated fragments obtained or not, the subject being considered as having said genetic polymorphism (such as SNP or mutation) whether said calculated percentage is greater than a threshold value associated to said genetic polymorphism.

When the method implementing the PCR, particularly the Q-PCR, for the detection of genetic polymorphism in said cell free nucleic acid in a body fluid sample, in an also preferred embodiment of the method of the present invention, the concentration of said amplified fragment of said cell free nucleic is calculated for an amplified mutated fragment and/or an amplified non-mutated fragment.

By mutated fragment and non-mutated fragment, it is intended to designate herein a fragment exhibiting and not exhibiting respectively the genetic polymorphism which is desired to detect in the method of the present invention.

In a preferred embodiment of said above method of the invention, the ratio of the concentration of amplified long fragment and amplified short fragment is calculated for the amplified mutated short fragment and/or an amplified non-mutated short fragment.

In a particular embodiment, the method of the present invention further comprising a step of determining the concentration of amplified fragment of cell free nucleic acid presenting a specific genetic polymorphism, said amplified fragment exhibiting the genetic polymorphism having a defined length and wherein said concentration is compared to the concentration of a non-mutated amplified fragment of free cell nucleic acid, said non-mutated fragment having circa the same length of the mutated fragment, preferably the length mutated or non mutated amplified fragments can be similar in length+ or −20%.

In an also preferred embodiment of the method for the detection of a specific genetic polymorphism of the present invention implementing the said method further comprises:
a step of determining the concentration in the cell free nucleic acid extract of amplified non-mutated fragment and mutated fragment; and
calculating the percentage of the amount of short amplified mutated fragment relative to the short amplified non-mutated fragment obtained or not, the subject being considered as having said genetic polymorphism (such as SNP or mutation) whether said calculated percentage is greater than a threshold value associated to said genetic polymorphism.

In another aspect particularly preferred, the present invention is directed to a method for the analysis of cell free nucleic acid, particularly circulating DNA, in an individual, said method comprising the steps of:
a) the quantification of said free cell nucleic acid according to the invention by a method implementing the quantitative real-time polymerase chain reaction (Q-PCR); and
b) the determination of the integrity index of said free cell nucleic acid according to the invention by a method implementing the Q-PCR; and
c) the detection of the presence of a genetic polymorphism on said free cell nucleic acid according to the invention by a method implementing the Q-PCR.

In a preferred embodiment, said nucleic acid is nucleic acid carrying tumor-associated genetic alterations.

More preferred are nucleic acids selected from the group consisting of:
the RAS family gene, preferably KRAS or NRAS, carrying tumor-associated genetic alterations, preferably CRC-associated genetic alterations; and
the BRAF gene.

By body fluid sample, it is intended and preferred to designate the body fluids selected from the group consisting of whole blood, serum, plasma, urine, sputum, colonic effluent, bone marrow, lymph, cerebrospinal fluid, lacrymal fluid, sweat, milk, faeces, bronchial lavages and ascites.

In a preferred embodiment, the body fluid sample is blood sample selected from the group consisting of plasma and serum.

In an also preferred embodiment of the method of the present invention, said cell free nucleic acid is selecting from the group of endogenous or exogenous cell free nucleic acid, particularly exogenous cell free nucleic acid selected from the group consisting of cell free nucleic acids originating from viruses, bacteria, fungus, foetus and xenografts.

Among the endogenous cell free nucleic acid from a subject of interest, it is preferred that said subject of interest is a subject suffering from or at risk for developing a disease or exhibiting a physiological state or condition.

In a preferred embodiment, said disease is a cancer, more preferably but not limited to a cancer selected from the group of colorectal cancer, lungs cancer, breast cancer, prostate cancer, gynaecologic cancer, head and neck cancer, thyroid cancer, pancreatic cancer, liver cancer or hematopoietic cancers.

In an also preferred embodiment, said cancer is a metastatic cancer.

In another aspect, the present invention is directed to a method to identify or to analyse body fluid (preferably plasma) of cancer patient from body fluid (preferably plasma) from healthy individual wherein said method comprises the steps of:
a) quantifying the cell free DNA (cfDNA) in the two body fluid samples by a method of the present invention, cfDNA of size within the 50-100 bp range and of size superior to 101 bp;
b) comparing the ratio obtained between the level of these two fragment ranges for each of the two body fluid sample and wherein a ratio long/short size range <1, and preferably <0.75 being indicative of presence of a tumor.

The present invention is directed to a method to identify whether a body fluid (preferably plasma) sample of an individual is from a cancer patient or from healthy individual wherein said method comprises the steps of:
a) quantifying the cell free DNA (cfDNA) in the body fluid sample by a method of the present invention, cfDNA of size within the 50-100 bp range and of size superior to 101 bp;
b) calculating the ratio obtained between the level of these two fragment ranges for said body fluid sample and wherein a ratio long/short size range <1, and preferably <0.75 being indicative of presence of a tumor.

In a preferred embodiment, the present invention is directed to a method to identify or to analyse body fluid (preferably plasma or serum) of cancer patient from body fluid (preferably plasma of serum) from healthy individual wherein said method comprises the steps of:
a) quantifying the cell free DNA (cfDNA) in the two body fluid samples by a method of the present invention, cfDNA of size within the 50-100 bp range and of size within the range of 100 to 145 bp; preferably within the 73-99 bp range and of size within the range of 100-120 bp;
b) comparing the ratio obtained between these two fragments for each of the two body fluid sample and wherein a ratio long/short size range <1, and preferably <0.5 being indicative of presence of a tumor.

In another aspect, the present invention is directed to a method to identify or to analyse body fluid (preferably plasma or serum) of cancer patient from body fluid (preferably plasma or serum) from healthy individual wherein said method comprises the steps of:
a) quantification of the cell free DNA (cfDNA) in the two body fluid samples by a method of the present invention, cfDNA of size <249 bp and of size >249 bp, preferably cfDNA of size <100 bp and of size within the range of 249-409 bp, and more preferably within the 73-100 bp range and of size within the range of 300-357 bp;
b) comparing the ratio obtained between these two fragments for each of the two body fluid sample and wherein a ratio long/short size range <0.5, and preferably <0.1 being indicative of presence of a tumor.

In another aspect, the present invention is directed to a method to identify or to analyse body fluid (preferably plasma or serum) of cancer patient from body fluid (preferably plasma or serum) from healthy individual wherein said method comprises the steps of:
a) quantification of the cell free DNA in the two body fluid samples by a method of the present invention, wherein the cfDNA fragments whose concentration are determined for each body fluid sample are long fragments superior to 180 bp in length and short fragments inferior to 100 bp in length;
b) comparing the ratio obtained between these two fragments concentrations for each of the two body fluid sample and wherein a ratio long/short <0.4, and preferably <0.1 being indicative of presence of a tumor.

In another aspect, when PCR, particularly the Q-PCR, is implemented, the present invention is directed to a method to identify or to analyse body fluid (preferably plasma or serum) of cancer patient from body fluid (preferably plasma or serum) from healthy individual wherein said method comprises the steps of:
a) quantification of the cell free DNA in the two body fluid samples by a method of the present invention, wherein the amplified fragments whose concentration are determined for each body fluid sample are long fragments superior to 180 bp in length and short fragments inferior to 100 bp in length;
b) comparing the ratio obtained between these two fragments concentrations for each of the two body fluid sample and wherein a ratio long/short <0.4, and preferably <0.1 being indicative of presence of a tumor.

In another aspect, the present invention is directed to a method to identify or to analyse body fluid (preferably plasma) of cancer patient from body fluid (preferably plasma) from healthy individual wherein said method comprises the steps of:
a) quantification of the cell free DNA (cfDNA) in the two body fluid samples by a method of the present invention, cfDNA of size >145 bp;
b) calculating the percentage of cfDNA quantity obtained from the total cfDNA quantity wherein % is below 20%, preferably % being indicative of presence of a tumor.

In another aspect, the present invention is directed to a method to identify or to analyse body fluid (preferably plasma) from individuals where cfDNA are highly released, such as cancer patients from body fluid (preferably plasma) from healthy individual wherein said method comprises the steps of:
a) quantifying the cell free DNA (cfDNA) in the two body fluid samples by a method of the present invention, cfDNA of size range 60-80 bp, 100-145 bp and 180-400 bp;
b) directly comparing the three quantification levels obtained between healthy and non healthy individual.

The inventors discovered that there are three range of cfDNA size by which concentration/amount can be determined, which can identify, analyse or discriminate between cfDNA from healthy subject and cfDNA from individuals where cfDNA are highly released, such as cancer patients. The size range being 60-80 bp, 100-145 bp and 180-400 bp. Diagnostic, prognostic, theragnostic, or evolution of a specific physiological state might assessed by comparing cfDNA size profile; preferably by combining at least three concentration values obtained when targeting circa 70 bp, circa 100 bp and circa 300 bp fragments; and preferably by combining them in a logistic (logarithmic) function.

Thus, in another aspect, the present invention is directed to a method to discriminate body fluid (preferably plasma) from individuals where cfDNA are highly released, such as cancer patients from body fluid (preferably plasma) from healthy individual wherein said method comprises the steps of:
a) quantifying the cell free DNA (cfDNA) in the two body fluid samples by a method of the present invention, cfDNA of size range 60-80 bp, 100-145 bp and 180-400 bp;
b) determining a size profile by using these three values as parameters in a logistic function.

In a same aspect, the present invention is also directed to a method to discriminate body fluid (preferably plasma) from individuals where cfDNA are highly released, such as cancer patients from body fluid (preferably plasma) from healthy individual wherein said method comprises the steps of:
a) quantifying the cell free DNA (cfDNA) in the two body fluid samples by a method of the present invention, cfDNA at various size between 50-400 bp range;
b) comparing the size profile obtained for these three ranges of size between the two body fluid samples, preferably by combining at least three concentration values obtained when targeting circa 70 bp, circa 100 bp and circa 300 bp fragments; and preferably by combining them in a logistic function such as a logarithmic function.

In a same aspect, the present invention is also directed to a method to discriminate in a biological sample/fluid mutated cf nucleic acid fragment from non-mutated cf nucleic acid fragment, said method comprising the steps of: determining and comparing the ratio of the concentration of long fragments and short fragments calculated for the mutated fragment and for the non-mutated fragment, and wherein in said method:
said ratio being compared at various size between 50-450 bp range, preferably said long fragment being comprised between 200 bp and 450 bp, with preferably at least two concentrations values, such as circa 200 bp and circa 300 bp and said short fragments being inferior to 145 bp and preferentially comprised between 50 bp and 99 bp.

Preferably the ratio 80-145 bp/145-300 bp, or 100-145 bp/145-350 is compared between the mutated and the non mutated cf nucleic acid fragment present in the biological fluid.

Also preferred is a method to discriminate body fluid (preferably plasma or serum) from individuals where cfDNA are highly released, such as cancer patients, from body fluid (preferably plasma or serum) from healthy individual wherein said method comprises the steps of:
a) quantifying the cell free DNA (cfDNA) in the two body fluid samples by a method of the present invention, cfDNA of size range 60-80 bp, 100-145 bp and 180-400 bp;

b) comparing the size profile obtained for these three ranges of size between the two body fluid samples, preferably by combining at least three concentration values obtained when targeting circa 70 bp, circa 100 bp and circa 300 bp fragments; and preferably by combining them in a logistic function such as a logarithmic function.

In a preferred embodiment, the method to discriminate body fluid according to the present invention, is implemented for the diagnostic, prognostic, theragnostic or for monitoring the evolution of a specific physiological state of an individual, wherein the size profile comparison obtained in step b) is indicative of that specific physiological state.

In another aspect, the present invention is directed to a method for the diagnostic, prognostic, theragnostic or for assessing the evolution of a specific physiological state of an individual, preferably in an individual where cfDNA are highly released, said method comprising the step of:
a) repeatedly calculating during an interval of time the index of integrity of a cell free nucleic acid in a body fluid sample obtained from said individual, the presence of said nucleic acid being associated to said specific physiological state, by a method for determining the index of integrity or SFR of cell free nucleic acid in a body fluid sample according to the present invention; and
b) comparing the indexes of integrity or SFR obtained and determining whether said index of integrity of cell free nucleic acid has been varied over this interval of time.

In a preferred embodiment, said specific physiological state is a physiological state resulting to the release of cfDNA or to cells apoptosis, preferably selected from the group consisting of cancer, diabetes, sickle cell disease, tissue trauma, sunburn, hemodialysis or intense effort production.

In a particular aspect, the above method of the invention is directed to a method for diagnosis, prognosis or to a theragnostic method of tumor progression in a patient, wherein in step a) said nucleic acid associated to the specific physiological state is associated to said tumor and wherein in step b), a decreased of index of integrity over this interval of time is indicative of the progression of the cancer.

In a preferred embodiment, a decreased of index of integrity or SFR to a value inferior to 0.5, preferably inferior to 0.1 is indicative of the progression of the cancer.

In another aspect, the present invention is directed to a method for the diagnostic, prognostic, theragnostic or for assessing the evolution of a specific physiological state of an individual, preferably in an individual where cfDNA are highly released, said method comprising the step of:
a) repeatedly calculating during an interval of time the concentration of a short mutated or non-mutated cell free nucleic acid in a body fluid sample obtained from said individual, the presence of said nucleic acid, mutated or non-mutated, being associated to said specific physiological state, by a method of quantifying cell free nucleic acid in a body fluid sample according to the present invention, and
b) comparing the concentrations obtained and determining whether the concentration of said amplified mutated or non-mutated fragment of said cell free nucleic acid has been varied over this interval of time.

In a preferred embodiment, said specific physiological state is a physiological state resulting to the release of cfDNA, preferably selected from the group consisting of auto-immune lupus, sepsis, myocardial infarction, multiple sclerosis or intense effort production.

In an also preferred embodiment of the above method, said nucleic acid associated to the specific physiological state is associated to said tumor and wherein in step b), an increased of the concentration of said amplified mutated or non-mutated fragment of cell free nucleic acid over this interval of time is indicative of the progression of the cancer.

In another aspect, the present invention is directed to a method for monitoring the efficacy of a cancer treatment in a patient, comprising the step of:
a) calculating during an interval of time the index of integrity of free nucleic acid in a body fluid sample obtained from said patient for at least one cancer marker nucleic acid by a method of quantifying cell free nucleic acid according to the present invention, and
b) comparing the index of integrity obtained and determining whether said index of integrity of said cell free nucleic acid has been increased or decreased over this interval of time, wherein an increase in said index of integrity is indicative of efficacy and a decrease in said index of integrity is indicative of a lack of efficacy of this cancer treatment.

In another aspect, the present invention is directed to a method for the analysis of cell free nucleic acid, particularly circulating DNA, in a individual such as in patient exhibiting a tumor or susceptible to exhibit a tumor, said method comprising the steps of:
a) the qualitative detection of the presence of a genetic polymorphism, such as a SNP or a mutation, on said free cell nucleic acid according to the present invention;
b) the quantification of said free cell nucleic acid according to the present invention; and
c) the determination of the rate of apoptosis by implementing the determination of integrity index of said free cell nucleic acid according to the present invention, said method integrating the following parameters and calculation:

A1A2 in one hand and B1B2 in another hand are the representation of the short amplified sequences; and A1B2 the long amplified sequence, either A1A2 or B1B2 comprising the genetic polymorphism, given CB1B2, CA1A2 and CA1B2 respectively the measured initial concentration of corresponding extracted nucleic acid by detecting the amplified short fragment B1B2, the amplified short fragment A1A2 and the amplified long fragment, respectively;

the qualitative detection of the presence of a genetic polymorphism:
% CB1B2/CA1A2 higher than a specific threshold, where B1B2 is defined as the amplicon sequence containing the genetic polymorphism; or
% CA1A2/CB1B2 higher than a specific threshold, where A1A2 is defined as the amplicon sequence containing the genetic polymorphism, the evaluation of the integrity index by determining the ratio CB1B2/CA1B2, or CA1A2/CA1B2, wherein, considering that X and Y is the distance on the nucleic acid between the 5' ends of the primers, or being the length of the amplified fragments (or amplicons):

$$\begin{cases}(A1A2) = (B1B2) = X \\ (A1B2) = Y\end{cases}$$

with X<180 and Y>X,
preferably 50<X<100 and 200<Y<450.

In a preferred embodiment, said nucleic acid corresponding with the genetic polymorphism of interest on the coding strand is located and the 3'-end extremity of the primer starting at position B1 or A2, and wherein the method implementing PCR is an allele specific PCR.

In a preferred embodiment, said amplified long fragment A1B2 partially or fully comprises the short non-mutated fragment and the mutated fragment containing said genetic polymorphism (such as SNP or mutation) to be detected (A1A2 and B1B2, or B1B2 and A1A2, respectively).

In a preferred embodiment, said amplified long fragment A1B2 is 300 bp+/−20% in length, and the short non-mutated fragment (A1A2 or B1B2) and the mutated fragment (B1B2 or A1A2) are 60 bp+/−20% in length.

In another aspect, the present invention is directed to a method for diagnosis or prognosis of tumor progression in a patient, or a theragnostic method comprising determining tumor progression in a patient, said method comprising the step of:
a) determining the concentration of a cell free nucleic acid in a body fluid sample from said patient by a method of quantifying cell free nucleic acid according to the present invention, and
b) detecting a genetic polymorphism (such as SNP or mutation) in said amplified short fragment of said cell free nucleic acid by a method according to the present invention.

In another aspect, the present invention is directed to a method for diagnosis, prognosis a pathological or physiological state such as the presence of a tumor or tumor progression in a patient, or a theragnostic method comprising determining said pathological or physiological state in a patient, said pathological or physiological state being associated to a nucleic acid genetic polymorphism (such as SNP or mutation), said method comprising the steps of:
a) studying at least two biomarkers selected from the group of:
the determination of the concentration of cell free nucleic acid in a body fluid sample from said patient, by a method of quantifying cell free nucleic acid according to the present invention;
the detection a said genetic polymorphism in said cell free nucleic acid by a method according to the present invention, wherein the classification of the patient as having or not said genetic polymorphism, being obtained by determining whether the percentage of mutated versus non-mutated cell free nucleic acid found is higher than a threshold, preferably said threshold being specific of a given genetic polymorphism and determined from a cohort of non-mutated and mutated patients; and
the determination of the index of integrity of said cell free nucleic acid in the sample, by a method according to the present invention,
b) combining said at least two values through a logistic function including said at least two biomarkers, and
c) analyzing said end value of said logistic function in order to diagnosis or prognosis the pathological or physiological state, such as a tumor or tumor progression in said patient.

Such a threshold value associated to said SNP in the present method of the invention where it is necessary can be determined from a cohort of two groups of patients, patients exhibiting or not the specific genetic polymorphism (such as SNP or mutation) associated to said SNP. Said threshold represents the minimum value beyond which it is established without ambiguity that the gene is mutated.

The present invention is also directed to a kit comprising two set of nucleic acid primers, preferably for detecting or quantifying in a body fluid sample the presence of a cell free nucleic acid of a gene of interest, said gene of interest being susceptible to present a mutation, more preferably for its use in the Intplex system of the present invention, characterized in that said two set of primers comprising:
a) a first set of two primers, named A1 (forward primer) and A2 (reverse primer), said two primers A1 and A2:
have a minimal size of 15 nucleotides and a maximal size of 30 nucleotides, and
have a minimal spacing of at least 5 bp between the two primers, between the 3' extremities of both primer, and
allows to obtain an amplicon having a size range comprised between 35 to 100 bp, said amplicon being in a region of said gene which does not exhibit the mutation of interest; and
b) a second set of two primers, named B1 (forward primer) and B2 (reverse primer), said two primers B1 and B2:
have a minimal size of 15 nucleotides and a maximal size of 30 nucleotides, and
have a minimal spacing of at least 5 bp between the two primers, between the 3' extremities of both primer, and
allows to obtain an amplicon having a size range comprised between 35 to 100 bp, said amplicon being in a region of said gene which exhibit the mutation of interest; and
wherein A1B2 being in the 250-450 bp size range.

The present invention is also directed to the kit according to the present invention, wherein:
the targeted region of said gene of interest where the B2 primer is located from 5 to 85 nucleotides downstream from the position of said mutation of interest
the region of said gene of interest where the primer pair A1A2 is designed in the region which is located within the 430-100 nucleotides upstream from the position of said mutation of interest,
preferably for its use in the conventional IntPlex system of the present invention.

The present invention is also directed to the kit according to the present invention, wherein:
the region of said gene of interest where the A1 primer is located from 5 to 85 nucleotides upstream from the position of said mutation of interest.
the region of said gene of interest where the primer pair B1B2 is designed in the region located within the 100-430 nucleotides downstream from the position of said mutation of interest,
preferably for its use in the inverse IntPlex system of the present invention.

The present invention is also directed to the kit comprising two set of nucleic acid primers according to the present invention, wherein the gene and/or the associated gene mutation of interest is selected from the group of:
A) Mutations in Disorders in Particular Cancer:
(For each gene are presented the position number in the cDNA of the by bearing the mutation upon NCBI 36: Ensembl Contig view <http://may2009.archive.ensembl.org/Homo_sapiens/Location/)
TP53: 394, 395, 451, 453, 455, 469, 517, 524, 527, 530, 586, 590, 637, 641, 724, 733, 734, 743, 744, 817, 818, 819, 820, 839, 844, 916
APC: 2626, 3340, 3907, 3934, 3964, 4012, 4099, 4132, 4133, 4285, 4286, 4348, 4729
MSH6: 1168
NF1: 3827, 3826
PIK3CA: 1530, 1624, 1633, 1634, 1636, 1656, 3140, 3140, 3140
SMAD4: 502, 931, 932, 988, 989, 1051, 1082, 1156, 1332, 1333, 1519, 1596, 1597, 1598, 1606

EGFR: 2155, 2155, 2156, 2303, 2369, 2573; deletions/loss: 2230 to 2244, from 2308 à 2328
CDKN2A: 172, 205, 238, 239, 298, 250, 322, 369, 427, 394
IDH1: 394; 395
PTEN: 125, 126, 182, 302, 314, 387, 388, 389, 1911, 577, 518, 519, 697, 698, 1003, 1004
SMARCB1: 118, 153, 154, 379, 380, 425, 471, 472, 473, 601, 618, 619, 777, 776, 778
CTNNB1: 7, 94, 95, 98, 100, 101, 110, 121, 122, 133, 134, 170
HNF1A: 82, 81, 83, 196, 378, 379, 493, 494, 495, 526, 527, 617, 618, 685, 710, 749, 787, 817
VHL: 194, 203, 241, 266, 340, 343, 388, 452, 473, 480, 478
ATM: 1229, 1810, 2571, 2572, 2573, 3925, 8774, 9023
EZH2: 1936, 1937
RET: 2753
NRAS: 181, 182, 183
PTCH1: 135, 338, 416, 417, 1242, 1243, 1244, 1280 1281, 1284, 1301, 1302, 1315
KIT: 1668, 1669, 1670, 1679, 1680, 1681, 1682, 1727, 1728, 1924, 1925, 1961, 1962, 2467, Deletions from 1645 à 1727
NF2: 168, 169, 170, 459, 460, 586, 592, 634, 655, 656, 784, 1021, 1022, 1396
PDGFRA: 1680, 1681, 1682, 1975, 1976, 1977
MEN1: 124, 256, 291, 292, 293
PPP2R1A: 536, 767
STK11: 196, 910
MLL3: 1097, 4432, 6301, 6851, 8911, 10040, 10495, 12048, 12165
FOXL2: 402
GNAS: 601, 602, 680
HRAS: 34, 35, 36, 37, 39, 181, 182
FGFR3: 742, 743, 744, 746, 1108, 1111, 1112, 1113, 1114, 1115, 1116, 1117, 1118, 1949
PTCH1: 549, 550, 584, 1093, 1249, 1804, 2446, 3054, 3944, 3945, 3946
CDH1: 367, 368, 1000, 1057, 1108, 1204, 1436, 1437, 1742;
B) Mutation in Disorders Other than in Cancer:
a) Single Gene Disorders:
Autosomal dominant gene: Familial hypercholesterolemia, Huntington's disease, neurofibromatosis type 1, Marfan syndrome, hereditary nonpolyposis, colorectal cancer, hereditary multiple exostoses, Polycystic kidney disease, achondroplasia, Sickle-cell anemia, achondroplasia, Sickle-cell anemia
b) Autosomal recessive allele: cystic fibrosis, sickle-cell disease, Tay-Sachs disease, Niemann-Pick disease, spinal muscular atrophy, Roberts syndrome, Phenylketonuria, Mucopolysaccharidoses, Glycogen storage diseases
c) X-linked dominant: Rett syndrome, incontinentia pigmenti, Aicardi syndrome, Klinefelter syndrome, incontinentia pigmenti, Duchenne muscular dystrophy, Hemophilia
d) Y linkage: male infertility and hypertrichosis pinnae
e) Mitochondrial disease: Leber's hereditary optic neuropathy
f) Multifactorial and Polygenic (Complex) Disorders:
asthma, autoimmune diseases such as multiple sclerosis, cancers, ciliopathies, cleft palate, diabetes, heart disease, hypertension, inflammatory bowel disease, mental retardation, mood disorder, obesity, refractive error, infertility The present invention is also directed to the kit comprising two set of nucleic acid primers according to the present invention, wherein the mutation of the gene of interest is selected from the group consisting of the mutations of KRAS and BRAF gene, particularly the BRAF V600E mutation.

The present invention is directed to a kit comprising one or two set of nucleic acid primers, preferably for detecting or quantifying in a body fluid sample the presence of a cell free nucleic acid of the gene KRAS, said gene KRAS being susceptible to present a mutation selected from the group of KRAS G12 mutation, preferably G12V, G12D, G12A, G12S and G12C mutation, and G13D mutation, more preferably for its use in the Intplex system, characterized in that said set of primers or two sets of primers comprising:
a) a first set of two primers, named A1 (forward primer) and A2 (reverse primer), said two primers A1 and A2 being selected from the group consisting of:
for A1, SEQ ID NOs 163 to 196,
for A2, SEQ ID NOs 250 to 256; or/and
b) a second set of two primers, named B1 (forward primer) and B2 (reverse primer), said two primers B1 and B2 being selected from the group consisting of:
for B1, SEQ ID NOs 244 to 249,
for B2, SEQ ID NOs 83 to 120.

The present invention is also directed to a kit comprising one or two set of nucleic acid primers, preferably for detecting or quantifying in a body fluid sample the presence of a cell free nucleic acid of the gene BRAF, said gene BRAF being susceptible to present the mutation V600E, more preferably for its use in the Intplex system, characterized in that said one or two set of primers comprising:
a) a first set of two primers, named A1 (forward primer) and A2 (reverse primer), said two primers A1 and A2 being selected from the group consisting of:
for A1, SEQ ID NOs 65 to 81,
for A2, SEQ ID NO. 19; or/and
b) a second set of two primers, named B1 (forward primer) and B2 (reverse primer), said two primers B1 and B2 being selected from the group consisting of:
for B1, SEQ ID NO. 38,
for B2, SEQ ID NOs 40 to 63.

In another aspect, the present invention is directed to a nucleic acid primer, preferably for detecting or quantifying in a body fluid sample the presence of a cell free KRAS DNA containing a sequence of a same KRAS intronic region, preferably for determining the size profile of such cell free nucleic acid in a body fluid sample from a patient, said nucleic acid being selecting from the group of the primers having the sequence SEQ ID NOs: 1 to 8 (see table 1).

The present invention is also directed to a set of nucleic acid primers, preferably for detecting or quantifying in a body fluid sample the presence of a cell free KRAS nucleic acid, more preferably KRAS DNA, said set of primers being selecting from the group of following set of primers:
a) a set of primers comprising the primer having the sequence SEQ ID NO: 1 and at least two different primers, preferably three different primers selecting from the group of primers having the sequences SEQ ID NOs: 2 to 8;
b) a set of primers comprising the primer having the sequence SEQ ID NO: 1, the primer having the sequence SEQ ID NO: 8, and at least one or two primers selecting from the group of primers having the sequences SEQ ID NOs: 2 to 7;
c) a set of primers comprising the primer having the sequence SEQ ID NO: 1, the primer having the sequence SEQ ID NO: 7 and a primer selecting from the group of primers having the sequences SEQ ID NOs: 2 to 6; and
d) a set of primers comprising the primers having the sequences SEQ ID NO: 1 to 8.

The present invention is also directed to a set of nucleic acid primers, preferably for its use in the Intplex system towards demonstrating the presence of the KRAS G12V mutation in a body fluid sample, said set of nucleic acid primers comprising the primers having the sequences SEQ ID NOs: 9 to 14, preferably 9 to 15 (see table 2).

More preferably the present invention is directed to a set of nucleic acid primers, preferably for its use in the Intplex system towards demonstrating the presence of KRAS G12 mutation (G12V, G12D, G12A, G12S and G12C) and G13D mutation in a body fluid sample, said set of nucleic acid primers comprising the primers having the sequences SEQ ID NOs: 28 to 36, preferably 29 to 37 (see table 4).

The present invention is finally directed to a set of nucleic acid primers, preferably for its use in the Intplex system towards demonstrating the presence of the BRAF V600E mutation in a body fluid sample, said set of nucleic acid primers comprising the primers having the sequences SEQ ID NOs: 16 to 21, preferably 16 to 22 (see table 2).

More preferably the present invention is directed to a set of nucleic acid primers, preferably for its use in the Intplex system towards demonstrating the presence of the BRAF V600E mutation in a body fluid sample, said set of nucleic acid primers comprising the primers having the sequences SEQ ID NOs: 23 to 26, preferably 23 to 27 (see table 4).

Finally the present invention is directed to a kit for detecting or quantifying in a body fluid sample the presence of cell free KRAS or BRAF nucleic acid, more preferably cell free DNA, optionally cell free DNA exhibiting a genetic polymorphism, or to determine the size profile of said cell free KRAS nucleic acid in a biological sample, said kit comprising a set of primers as above indicated according to the present invention.

The following examples and also the figures and the legends hereinafter have been chosen to provide those skilled in the art with a complete description in order to be able to implement and use the present invention. These examples are not intended to limit the scope of what the inventor considers to be its invention, nor are they intended to show that only the experiments hereinafter were carried out.

LEGEND TO THE FIGURES

The patent or application file contains at least one color drawing executed in color. Copies of this patent or patent application publication with color drawing(s) will be provided by the Office upon request and payment of the necessary fee.

FIG. 1:

Quantification by Q-PCR of genomic DNA isolated from CRC (colorectal cancer) HCT-116-s cells using primer pairs that lead to the amplification of amplicons of different sizes of the gene KRAS. The values are obtained by quantifying a sample at a dilution that corresponds to 45 pg/µL. The concentration of the genomic DNA sample was measured by optical density before use in Q-PCR. The histograms represent the mean values of three different experiments. The experiments were carried out in duplicate and the results are expressed in pg/µL of extract.

Figure 2A:
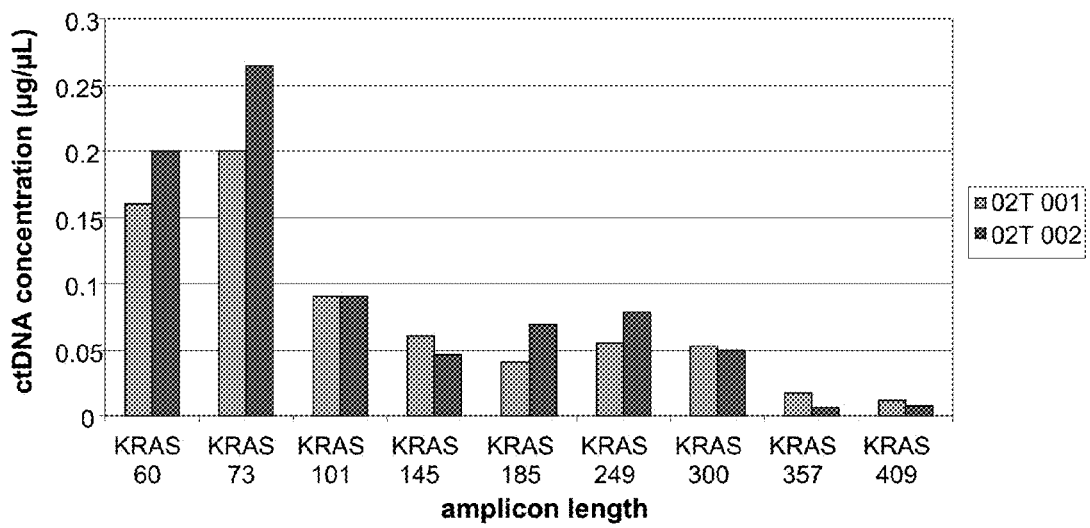
Figure 2B:
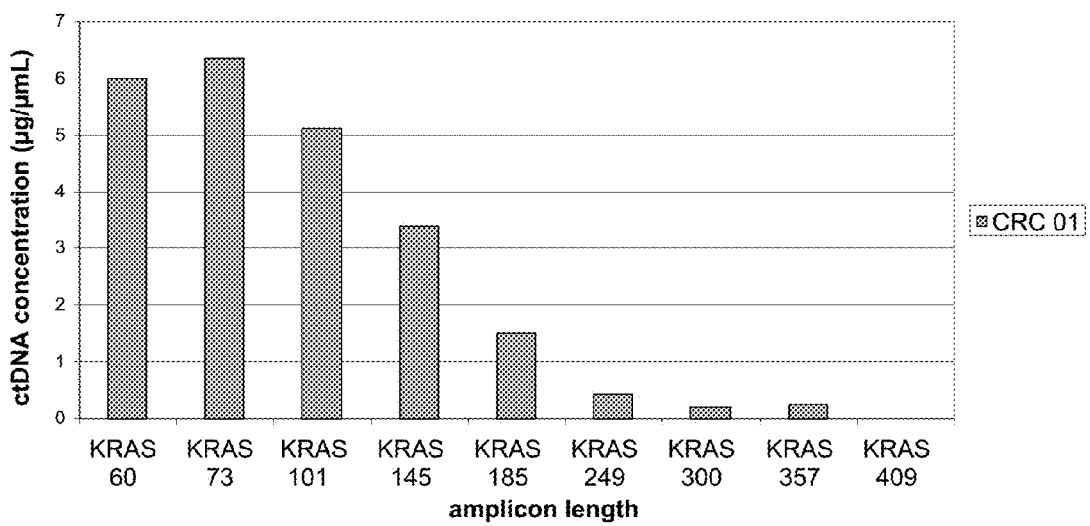

FIGS. 2A and 2B:

Quantification by Q-PCR of cirDNA isolated from 3 patients with metastatic CRC prior surgery and chimiotherapy relative to the amplicon size. FIG. 2A, serum samples (n=2 patients). FIG. 2B, plasma sample of one patient. The determination of the concentrations of cirDNA of each patient was done in duplicate. Histogram corresponds to the mean of the duplicate. Results are expressed in ng/µL of cirDNA.

FIG. 3:

Quantification by Q-PCR of cirDNA isolated from plasma samples of three healthy individuals aged between 20 and 25 years. The concentration of cirDNA was determined using a Q-PCR system that amplifies fragments of size ranging from 60 to 409 bp. The histograms show the mean values expressed in pg cirDNA/mL plasma. For instance, the maximum value obtained with the primer pair KRAS 101 corresponds to a concentration of 4.8 ng/ml plasma.

FIG. 4:

Illustration of the advantage in amplifying short DNA sequence in regards to detection of mutated ctDNA. Use of 3 primer sets (A, B and C) producing amplicon of different sizes are represented when analyzing genomic DNA, poorly and highly fragmented DNA.

FIG. 5:

Relative proportions of concentration values relative to the amplicon size.

FIG. 6:

Concentrations of cirDNA obtained by amplifying a long fragment of 249 bp or a short fragment of 60 bp in plasma samples from one healthy subject with low level of cirDNA (23 ng/ml plasma), one mCRC patient with intermediate level of cirDNA (450 ng/ml plasma) and one mCRC patient with high concentration of cirDNA (1860 ng/ml plasma). The cell line sample corresponds to the values obtained for genomic DNA isolated from HCT116-s cells (4.8 ng/ml, FIG. 1). Values are expressed as fractions of the maximum value obtained with primer pairs for the amplification of DNA fragments of increasing size (60, 73, 101, 145, 185, 249, 300, 357 and 409 bp).

Figure 7A:
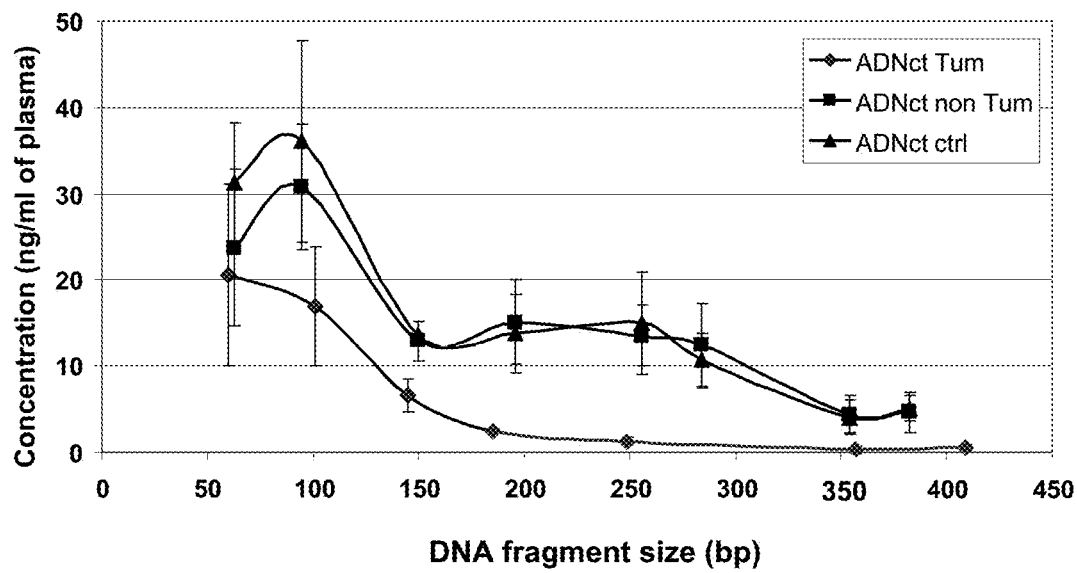
Figure 7B:
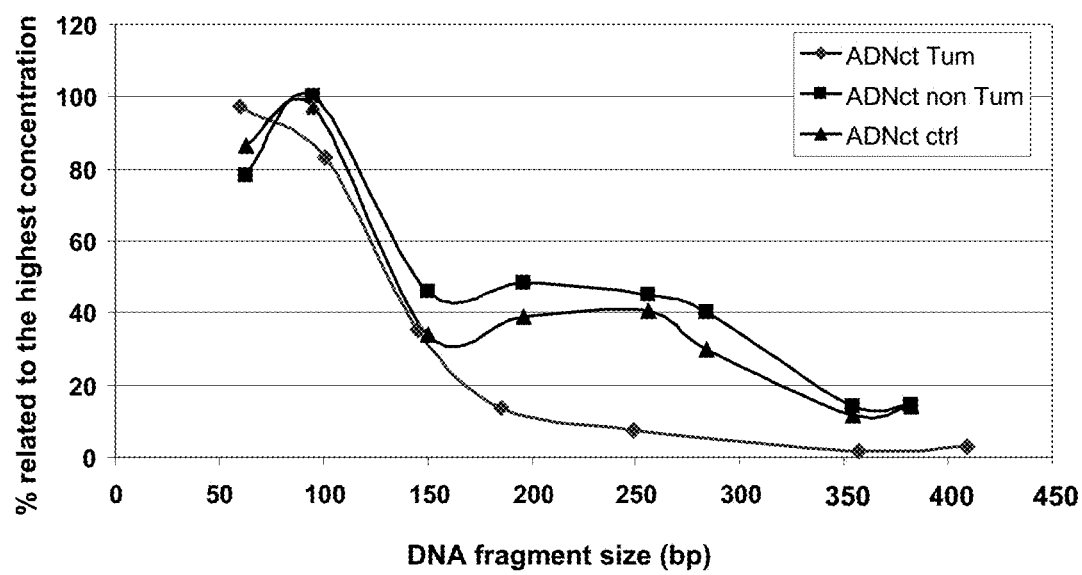

FIGS. 7A and 7B:

Specific tumoral ctDNA concentration size profile in xenografted mice. Two series of 7 primer sets generating amplicon of increasing length between 60 and 409 bp or 60 and 385 bp of human or mouse origin, respectively, were used. Each point corresponds to the mean of three pools of 4 different mouse plasmas.

Figure 8A:
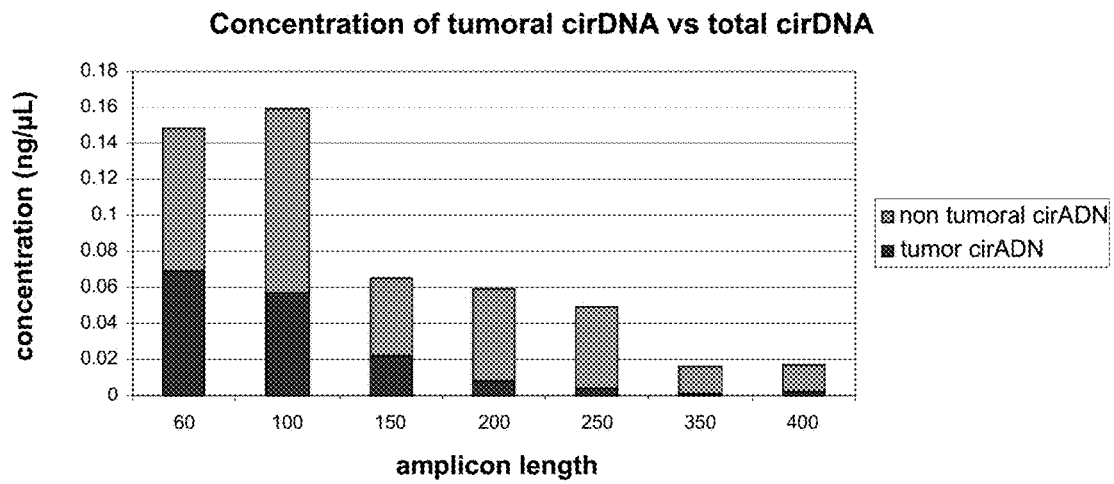
Figure 8B:
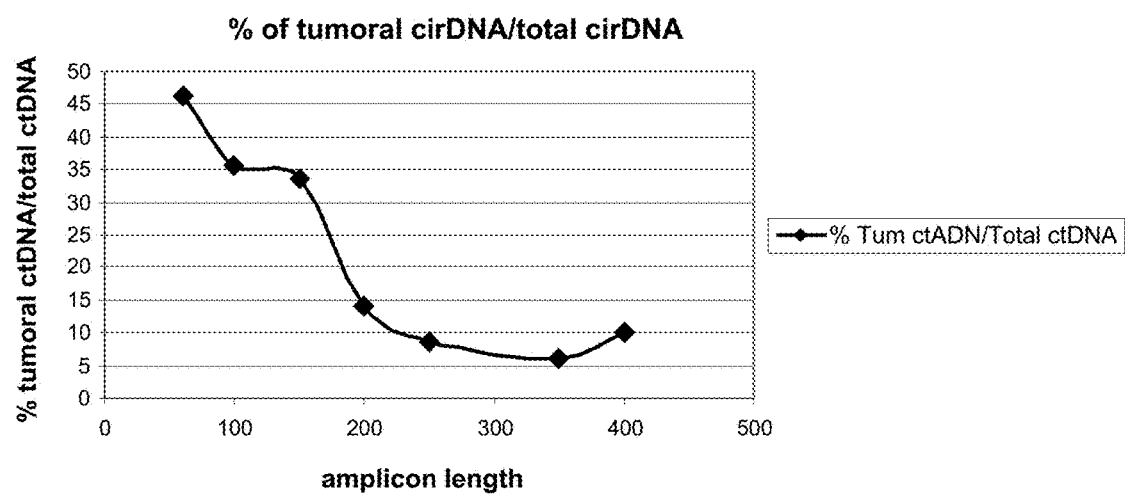

FIGS. 8A and 8B:

Contribution of tumoral cirDNA amount in total cirDNA amount in xenografted mice plasma.

FIG. 9:

Schematic representation of an example of the use of the IntPlex method for the analysis of SNPs.

FIG. 10:

Application of the Intplex system to cancer.

Figure 11A:
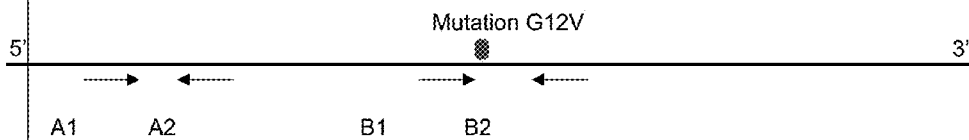
Figure 11B:
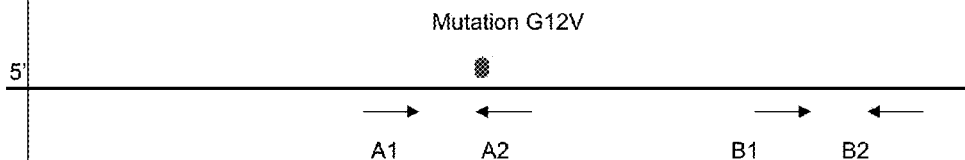

FIGS. 11A and 11B:

FIG. 11A) Schematic representation of the KRAS Conventional Intplex system in which the mutation is at the 3' end of the sense primer B1.

FIG. 11B) Schematic representation of the KRAS Reverse Intplex system in which the mutation is at the 3' end of the antisense primer A2.

FIG. 12:

Efficiency of the Kinv system for the quantification of cirDNA from mice xenografted with the human cancer cells SW620. Red numbers: size of the amplicons (in bp).

FIG. 13:

Efficiency of the Kconv system for the quantification of cirDNA from mice xenografted with the human cancer cells SW620. Red numbers: size of the amplicons (in bp).

FIG. 14:

Q-PCR quantification of the DNA from S4 HT29.

FIG. 15:

S4 HT29DNA diluted (1/10) in human genomic DNA.

FIG. 16:

Data presented as a percentage of the highest concentration in the series.

FIG. 17:

Mutated fragments concentrations (in %) versus non-mutated fragments concentrations observed using the Intplex process from human plasma DNA.

FIGS. 18A-18B:

Discrimination of plasma from healthy to CRC individuals. CirDNA concentration values are presented in the table and expressed in ng/mL plasma. Histograms represent the % of cirDNA amount contained in the size fraction.

FIGS. 19A-19B:

Agarose gel electrophoresis of 20 µg of ctDNA extracted from two CRC patients (CRC021, FIG. 19A and CRC019, FIG. 19B).

FIG. 20:

Comparison of the DII values (A) from genomic DNA, and ctDNA from human plasmas (healthy and CRC).

FIG. 21:

Comparison of the DII values calculated with the primer design of the present invention with the value obtained with using primer pairs targeting distant DNA sequences.

FIGS. 22A-22E:

Determination of various parameters indicative of ctDNA fragment size pattern (data are plotted in histograms.

FIG. 23: Localisation of Primers Sequences for BRAF Gene (Conventional and Reverse (or Inverse) System)

Example of DNA region to be targeted upon the IntPlex method when BRAF V600E point mutation is of interest. FIG. 23 shows the regions where molecular entities such as primers could target upon our multiplex method applied to this mutation.

Yellow: conventional system; Green: reverse system; Red: blocker; Pink: SNP.

FIGS. 24A-24E: Localisation of the Exon 2 regions and primers sequences for the KRAS gene (conventional and reverse (or inverse) system)

FIG. 24A: Example of DNA region to be targeted upon the IntPlex method when the hot spot point mutations of the 2nd and 3rd codon of the second exon of the KRAS gene is of interest.

Yellow: reverse primer for mutated amplicon: 6156 to 6236

Green: primer pair for non mutated amplicon: 5721 to 6051

FIG. 24A shows the regions where molecular entities such as primers could target upon the multiplex method applied to this mutation.

FIG. 24B: Localisation of primers sequences for KRAS conventional and reverse system.

Yellow: conventional system; Green: reverse system; Red: blocker; Pink: SNP.

FIG. 24C: Selected DNA region target for B1B2 primer pair design for detecting exon 2 KRAS hot spot mutations upon the reverse configuration of the system of the present invention. A1: GCCTGCTGAAAATGACTG (SEQ ID NO: 257); A2: in yellow and in green.

FIG. 24E: Selected DNA region target for A1 primer for detecting KRAS exon 2 hot spot mutations upon rev configuration:

A2: GTGGCGTAGGCAAGAGTGCCTT (SEQ ID NO: 160)

A1: selected DNA region target in yellow and green.

FIG. 24D: Selected DNA region target for B2 primer for detecting KRAS exon 2 hot spot mutations upon cony configuration:

B1: ACTTGTGGTAGTTGGAGCTGG (SEQ ID NO: 121)

B2: selected DNA region target in yellow and green.

EXAMPLES

Example I

Determination of the Size Range of cirDNAs

In order to determine the optimal size of the amplicons for a more specific and sensitive analysis of cirDNAs by Q-PCR, we have designed and used 9 pairs of primers that allow the amplification of amplicons of 60, 73, 101, 145, 185, 249, 300, 357 and 409 bp within the same region. They have been designed in such a way that a smaller amplicon is always comprised within the sequence of a bigger amplicon, the antisense primer being the same for each pair of primers. This amplified region of 409 bp is located in intron 2 of KRAS. The sequence of the oligonucleotide primers are presented in Table 1.

TABLE 1

| | |
|---|---|
| Kras rev | GGT CCT TTT CCG TGT GTA GG (20 bp) (SEQ ID NO: 1) |
| Kras 409 | GCC TCC CTT TCC AGC ACT (18 bp) (SEQ ID NO: 2) |
| Kras 357 | GGC ATC TCT AGG ACG AAG GT (20 bp) (SEQ ID NO: 3) |
| Kras 300 | GGT CCT TTT CCG TGT GTA GG (20 bp) (SEQ ID NO: 4) |
| Kras 249 | TGG AAG AGC ATA GGA AAG TGC (21 bp) (SEQ ID NO: 5) |
| Kras 185 | ATC TGC CTC CGA GTT CCT G (19 bp) (SEQ ID NO: 6) |
| Kras 101 | CCC TAC ACG TAG AGC CTG TGA (21 bp) (SEQ ID NO: 7) |
| Kras 73 | GCC TGT GAC CTA CAG TGA AAA (21 bp) (SEQ ID NO: 8) |

Concentration Obtained by Using Each Primer Pairs to Analyse Genomic DNA

FIG. 1 describes the variation in the yield of the tested primer pairs. All results are from 3 experiments carried out in duplicate. The amplification reaction efficiency by Q-PCR of a given DNA sequence is linked to the thermodynamics properties of the primers and differs, among other things, in function of the amplicon size. As shown in FIG. 1 the efficacy of detection of the primer pairs (with very similar hybridization properties) is relative to the size of the tested amplicons. As illustrated in FIG. 1 the detection seems to be optimal for amplicons between 101 and 185 bp. In the literature, it has been conventionally chosen to amplify regions going from 150 to 250 bp.

The presence of monomers or multiples of nucleosomes that have a size close to 180-200 bp has been already reported and is indicative of a mechanism of apoptosis for the release of cirDNA.

FIG. 2A summarizes the results obtained using two serum samples from two patients with metastatic colorectal cancer (mCRC). The cirDNA concentration curves of these two serum samples shows comparable profiles that present approximately three phases. A first one in which the concentration for amplicons of sizes between 60 and 73 bp (up to values ranging between 0.2 and 0.3 ng/µl) is similar, a second one for amplicon of sizes between 101 and 145 bp in which the concentration decreases sharply to values of about 0.05 ng/µl; and finally a third phase for amplicons of sizes between 145 and 409 bp in which the concentration of cirDNA is plateauing or very slowly decreasing up to 0.02 ng/µl.

FIG. 2B shows the cirDNA concentration as determined by using the same amplication systems of increasing length amplicons in a CRC patient plasma. Data show the same size profiling.

To note the two sera and the plasma used here originate from patients waiting for their first tumor resection surgery and not subjected to chemotherapy at the time of sampling.

Figure 3:
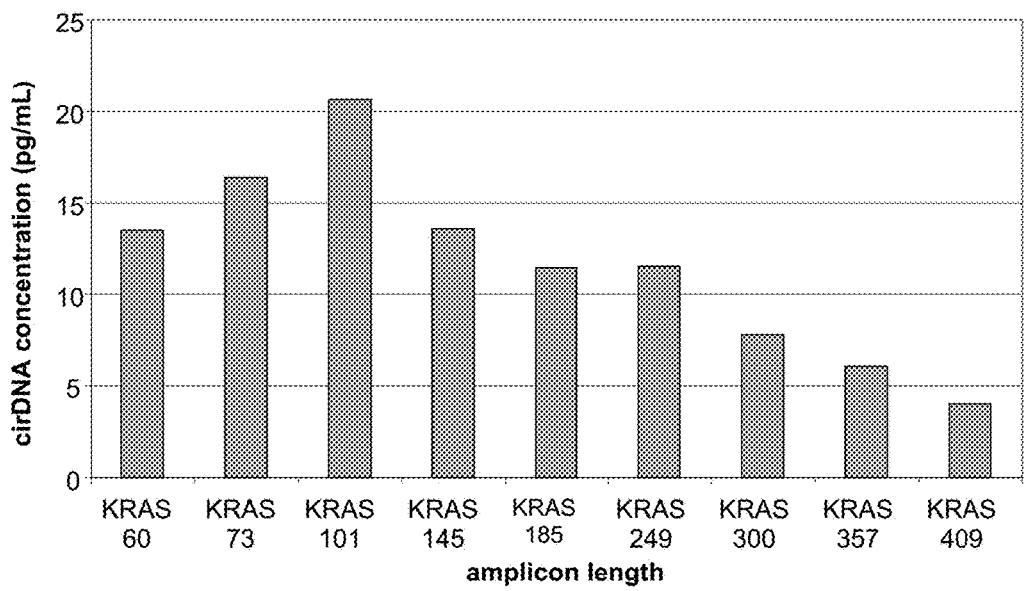

FIG. 3 summarizes the profiles of cirDNA concentrations in plasma samples of healthy subjects relative to the amplicon sizes. These results indicate that higher concentrations of cirDNA are detected with amplicons of sizes between 101 and 145 bp. Differently from the results for mCRC patients, in healthy subjects the results do not indicate the presence of a very significant variation in the detection of amplicons bigger or smaller than 101-145 bp.

We can discriminate plasma of cancer patient plasma from healthy individual by comparing quantification of cfDNA when detecting a amplified sequence (amplicon) of 145-409 and another of range of 50-73 bp. A ratio long/short <0.5, and preferably <0.1 being indicative of presence of a tumor.

The Reason why Amplicon Size is Crucial when Analysing cirDNA Vs Genomic DNA

Thus, the size profile of cirDNA as determined by amplifying amplicon of increasing sequence length reveals that optimal detection is made when amplifying amplicon <100 bp and that a much higher proportion of cirDNA of size ranging from 150 to 350 bp is present in non tumoral cirDNA as compared with tumoral cirDNA. The choice of the size of the amplified DNA region consequently appears crucial as illustrated by the scheme of the FIG. 4.

Thus, the choice of amplicon size is crucial for:
the sensitivity of the analysis by Q-PCR (increase of more than ten folds and up to 50 folds according to the quantity of cirDNA in the sample),
the specificity, because the analysis of the cirDNA concentration profile based on the amplicon size (or the determination of the optimal amplification) can distinguish the cirDNA of a patient with mCRC from the cirDNA of a healthy subject. The measure of the ratio between the quantification obtained for amplicons of sizes between 50 and 100 and the quantification obtained for amplicons bigger than 100 bp can be used to hypothesize the presence of cirDNA of tumour origin. In addition to the generally higher overall quantity of cirDNA in mCRC patients, the quality in terms of fragment size appears, for the first time, to be specific and informative about the presence of cancer cirDNA.

Figure 5:
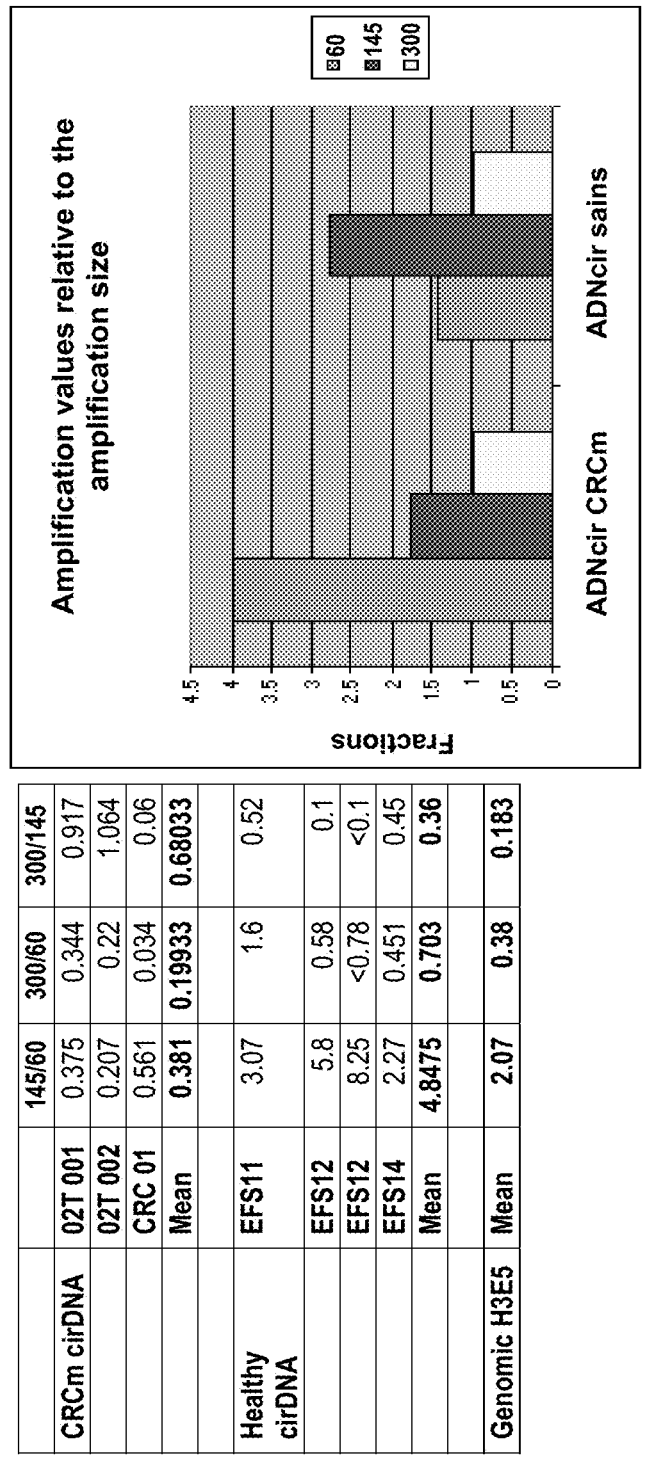

Moreover, it is possible to determine this specificity by measuring the integrity index that is calculated by comparing the concentrations of amplicons of specific sizes (FIG. 5).

The 145/60 or 300/60 ratio is always lower than 1 in the case of the analysis of cirDNA from mCRC patients. Conversely, the 145/60 ratio is 2.07 for genomic DNA.

The integrity index for 300/60 is lower than that for 145/60 in cirDNA from mCRC patients. Indeed, it is <0.344 in mCRC patients; whereas it is >0.45 in cirDNA from healthy subjects. The 300/60 ratio is 0.38 in genomic DNA.

The initial study of the analysis of the 145/60 and 300/60 ratio in healthy subjects and mCRC patients shows a sensitivity of 100% and a specificity of 100%. The 145/60 ratio seems thus to discriminate better between healthy subjects and mCRC patients than the 300/60 ratio especially when the standard deviation of the mean is taken into account, but to differentiate less well when the specificity is considered. The 300/145 ratio is not optimal to discriminate healthy/cancer patients and in general gives results which are the opposite of those obtained with the 300/60 ratio, i.e., the mean of the values obtained for 300/145 is higher for cirDNA from mCRC patients; yet it is this type of ratio (short fragment >100 bp and <180) that has conventionally been used in the few studies previously carried out on the integrity index (13-19).

It is important to indicate that the choice of primer pairs used (and thus in particular the size of the amplified sequence) for the detection of cirDNA is based only on their amplification yield for fragments between 100 and 300 bp according to the targeted sequence. The calculation of these integrity indexes could be used to discriminate between the cirDNAs of healthy subjects and mCRC patients. It has to be stressed that other ratios or integrity indexes could be calculated in function of the tumour development or of the total concentration of cirDNA.

The histograms of FIG. 5 shows that the relative proportions of the values obtained by amplifying the fragments of 60 and 145 bp are the opposite in healthy subjects in comparison to mCRC patients.

Figure 6:
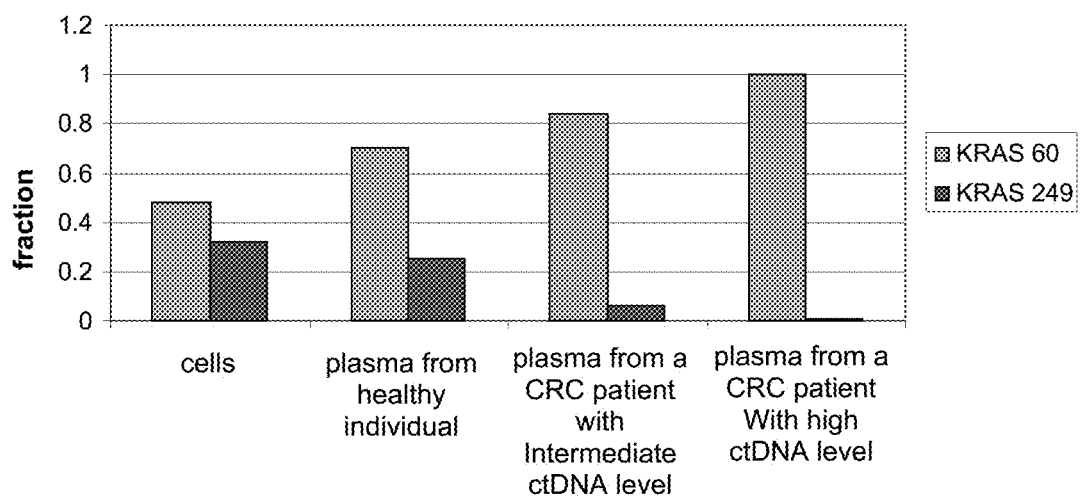

We have found that the bigger the quantity of cirDNA is, the lower the integrity index is. For instance (FIG. 6), the amplification value of the long fragment of 249 bp decreases while the amplification of the short fragment of 60 bp increases in function of the total quantity of cirDNA.

In summary, the results of that example allow, for the first time, the determination of innovative features concerning the detection of cfDNA by Q-PCR:

1. The size of the amplified fragment (amplicon) influences greatly the quantification of cfDNAs.
2. The detection of amplicons smaller than 100 bp is optimal.
3. The determination of an integrity index can be used to discriminate between the cirDNA of a subject with mCRC, the cirDNA of a healthy individual and also genomic DNA.
4. The comparison of the results of the PCR amplification of extracts of cirDNA can be done accurately only by comparing the amplification of primer pairs that produce amplicons of identical size.

Example II

Size Distribution Through Q-PCR Analysis of cirDNA Extracted from a CRC Xenograft Mouse Model Materials and Methods:
a) Cell Lines and Reagents SW620 CRC cells were maintained in RPMI+10% fetal bovine serum. SW620 cells have the homozygous KRAS G12V mutation (GGT to GTT)

b) Xenograft Model

Female athymic nude mice (6-8 wk/old) were xenografted subcutaneously with 1×106 cancer cells. Mice were euthanized with CO2 three weeks post-graft, the tumors weight being within the 300-650 mg. Peripheral blood was drawn into EDTA tubes and was immediately (within one hour) used for plasma preparation.

c) Plasma and Serum Preparation

Following collection in 5 ml BD vacutainer KE35 tubes (Belliver Industrial), mouse blood samples were centrifuged at 2000 rpm at 4° C. in a Heraeus Multifuge LR centrifuge with a CR 4j rotor for 10 minutes. Supernatants were collected in sterile 1.5 ml Eppendorf tubes and centrifuged at 14 000 rpm (16 000 g) at 4° C. for 10 min. Then supernatants were either immediately handled for DNA extraction or stored at −80° C. No significant difference was found in Q-PCR assays when comparing freshly isolated or stored plasma. Serum was prepared using the same 2-step centrifugation process, but blood was drawn in tubes without EDTA which were then left at room temperature for one hour. Mouse and human plasma and sera were isolated within 3 hours following sampling.

d) DNA Extraction ctDNA and genomic DNA from the different cell lines were extracted following the same procedure. DNA was purified from 200 µl plasma with the QIAmp DNA mini Blood kit (Qiagen, Calif.) according to the "Blood and body fluid protocol" with an elution volume of 60 µl. Samples were kept at 4° C. during plasma preparation. DNA samples were frozen at −20° C. until use. No significant difference was found in Q-PCR assay when comparing freshly extracted or stored DNA.

e) ctDNA Quantification by Q-PCR

DNA was quantified by Q-PCR assay. Real-time PCR amplifications were carried out in a reaction volume of 25 µl on a My iCycler IQ 5IQ or a Chromo4 instrument using the IQ5 Optical system software 2.0 and the MJ Opticon Monitor 3 software (Bio-Rad). Each PCR reaction mixture consisted of 12.5 µl mix PCR (Bio-Rad Super mix SYBR Green=Taq polymerase, MgCl2); 2.5 µl of each amplification primer (100 pmol/µl); 2.5 µl PCR-analyzed water and 5 µl DNA extract. Thermal cycling started by a first denaturation step of 3 min at 95° C., followed by 40 cycles of 95° C. for 10 sec and 60° C. for 30 sec. Melting curves were obtained from 55° C. to 90° C. with reading every 0.2° C. As calibrators for quantification, serial dilutions of genomic DNA from HCT116-s and MC38 cells were used. Sample concentrations were extrapolated from the standard curve by the IQ 5 Optical system software 2.0 or MJ Opticon Monitor 3 software. The limit of detection as the concentration that can be detected with reasonable certainty (95% probability) as recommended in the MIQE guidelines was 3 copies/assay (21).

Plasma extract were assayed by amplifying the same 60 to 409 bp DNA sequences of human KRAS intron 2 as previously used for the analysis of CRC clinical sample. In addition non tumor cirDNA was assayed by the same approach by with amplifying 60-385 bp DNA sequences of mouse KRAS intron 1. Plasma extracts from non xenografted control nude mice were as well assayed with using that method.

FIGS. 7A and 7B demonstrate first that a significant discrimination between tumor and non tumor derived cirDNA when amplifying sequences ranging from 200 and 300 bp. Second, concentration was found maximal when amplifying region <100 bp for tumoral cirDNA while maximum was reached when amplifying the 105 bp sequence for non tumor cirDNA and the 60 bp for tumor cirDNA.

Determination of the cirDNA integrity index (300/60) is therefore much lower for tumoral cirDNA than for non tumor cirDNA and for the non xenografted control mice cirDNA; being 0.05 as compared with 0.57 and 0.48, respectively.

FIGS. 8A and 8B present the contribution of tumor ctDNA amount in comparison with the total cirDNA amount (tumor+non tumor cirDNA amount) from data obtained in the same experiment. Data clearly show that the proportion of tumor cirDNA sharply decreased from 60-250 bp amplified region and then somewhat stabilized.

These observations confirm the results previously obtained with analysing human samples.

Moreover data highlight the difference between concentration profiles upon amplicon length between tumoral vs non-tumoral/control cirDNA.

Example III

Intplex Method

General Application of the IntPlex Analysis

CirDNAs carry the genetic marks of healthy and pathological cells, or of infectious agents. Thus, genetic alterations are targets of choice due to their clinical repercussions. One of the technical challenges concerning cirDNAs is their use as a tool to detect genetic polymorphisms especially SNPs (Single Nucleotide Polymorphisms).

SNPs are the most abundant of the genetic variations in the human genome. They represent more than 90% of all the differences among individuals. It is a type of DNA polymorphism in which two chromosomes differ on a given segment by one single base. In two human genomes at random, 99.9% of the DNA sequences are identical. The remaining 0.1% includes sequence variations of which the most common type is a single nucleotide polymorphism (SNP). SNPs are stable, very abundant and distributed uniformly in the entire genome. These variations are associated with the diversity within a population or among individuals, with the differences in susceptibility to diseases and with the individual response to drugs. Some are responsible for the perturbations of the cell cycle that can result in cell proliferation and ultimately in cancer development.

The majority of the methods for the analysis of SNPs are based on the possibility of denaturing DNA to single strands by heat and of renaturing it, by cooling down under precise conditions, with a strand of complementary sequence (PCR methods). Thus, PCR allows the identification and quantification of a DNA sequence through the analysis of its amplification thanks first to a particular polymerase and also to specific oligonucleotides that will « delimit» the sequence to be amplified.

PCR was previously adapted to detect SNP. One of the simplest PCR methods for the detection of known SNPs is the Allele-Specific Hybridization that is known also under the name of Allele-Specific Oligonucleotide hybridization (ASO). In this method, two short oligonucleotide probes, which differ only by one nucleotide, are used. The studied DNA is hybridized separately with these two labeled probes. The genomic DNA will hybridize only with the probe with the perfectly complementary sequence. The technique of allele-specific PCR can be carried out by using a marker of double-stranded DNA whose signal allows the quantification of the DNA amplification. The analysis by SYBR Green of a mutation has the considerable advantage of simplicity and rapidity.

Nevertheless, the simple analysis by SYBR Green generates, particularly for the identification of point mutations, a non-negligible specific detection thus rendering this approach not very reliable when the objective is a clinical or industrial kit. Various methods were developed to circumvent this non-specificity effect but they consist of 2 or more steps rendering them more time consuming.

Therefore, we have designed and developed an analytical method that leads to a qualitative conclusion about the presence or not of a genetic polymorphism. The determination of the positivity of the mutational status of a gene will be established by calculating the percentage of mutated cirDNA relative to the non-mutated cirDNA. For each given mutation, it will be possible to determine a percentage of non-specificity, called «threshold», beyond which it will established without ambiguity that the gene contains a polymorphism.

However, the use of a so-called «reference» amplification might be dangerous for the analysis of cirDNA because our results have demonstrated that the quantification of amplified DNA in this case varies very significantly in function of the length of the amplified fragment (the amplicon). Thus, keeping in mind our results, in the method IntPlex we will compare the amplification of an amplicon smaller than 100 bp, which contains the mutation to be detected, and the amplification of an amplicon of identical size.

In order to limit as much as possible the potential disparity in the sequences included in the cirDNA, the control amplicon will be localized close to the amplified sequence. The quantification of the reference amplicon will allow determining/confirming the specific total quantity of cirDNA as well.

Since mononucleosome has a size varying between 180 and 220 bp the ratio between the quantity of an amplicon bigger than 220 bp and the quantity of an amplicon smaller than 180 bp conventionally corresponds to a degree of integrity or of apoptosis. We designed Intplex as such the ends of the mutated and control amplicons will be separated by a minimum distance of 220 bp.

The integrity index (amplification of a long fragment/amplification of a short fragment) can be optimized to discriminate more in general healthy subjects and individuals with a pathology (cancer, for instance) by decreasing the size of the long fragment to a size>short fragment, and >180 bp.

Figure 9:
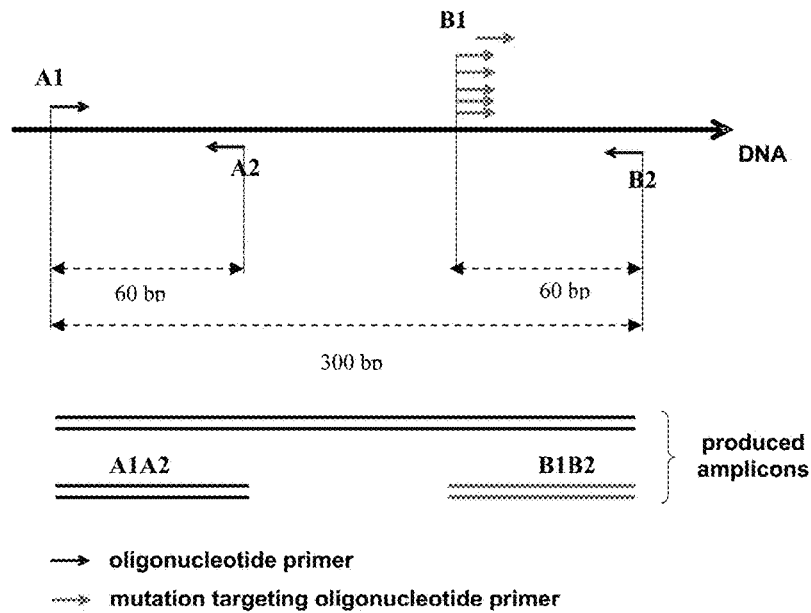

FIG. 9 shows an example of the use of the IntPlex method for the analysis of SNPs. In this example, the primer B1 includes in its 3' end the base change relative to the «wild type» status. The amplification with the primers A1 and A2 produces a fragment of 60 bp. The mutated fragment is amplified by the primers B1 and B2. The amplification with using A1 and B2 primers will produce a fragment of 300 bp.

Consequently, the invention consists in a method for the analysis of cfDNA that will integrate, based on the schematic shown as an example:

The qualitative detection of the presence of a genetic polymorphism (such as SNP or mutation);
The specific quantification of cirDNA;
The evaluation of the apoptosis rate;
By the following calculation upon the scheme in FIG. 9:
The qualitative detection of the presence of a genetic polymorphism (such as SNP or mutation):
% B1B2/A1A2 higher than a specific threshold;
with B1B2 defined as the sequence that contains the genetic polymorphism (such as SNP or mutation).
The specific quantification of the total cirDNA: A1A2 quantity.
The specific quantification of the tumoral cirDNA: B1B2 quantity.
The evaluation of the rate of apoptosis by determining cirDNA fragmentation in term of %: B1B2 or A1A2/A1B2.

If we model the integrated system by considering that X and Y is the distance on the DNA between the 5' ends of the primers, the integrated system Intplex can be modelled as such:

$$(A1A2)=(B1B2)=X$$

$$(A1B2)=Y$$

With X<180 and Y>X
Ideally: 50<X<100 and 200<Y<350.

This way of identifying the presence or not of a gene mutation is very convenient because it is very fast and not very expensive. Moreover, it allows dispensing with sophisticated techniques like sequencing. On the other hand, sequencing leads to an answer without possible doubts (but for contamination or handling mistakes).

CirDNA is constituted of DNA of tumour and non-tumour origin. Very little is known about the respective contribution of these two types of cirDNA during tumour progression. IntPlex should allow advancing on this issue and this information will bring valuable diagnostic and/or prognostic benefits. Indeed, the quantity of mutated, and thus of tumour DNA, can be linked by this method directly to the quantity of non-tumour DNA. The calculation of this percentage can be correlated both with the total quantity of released cirDNA and with the progression or regression of the tumour.

Example IV

Figure 10:
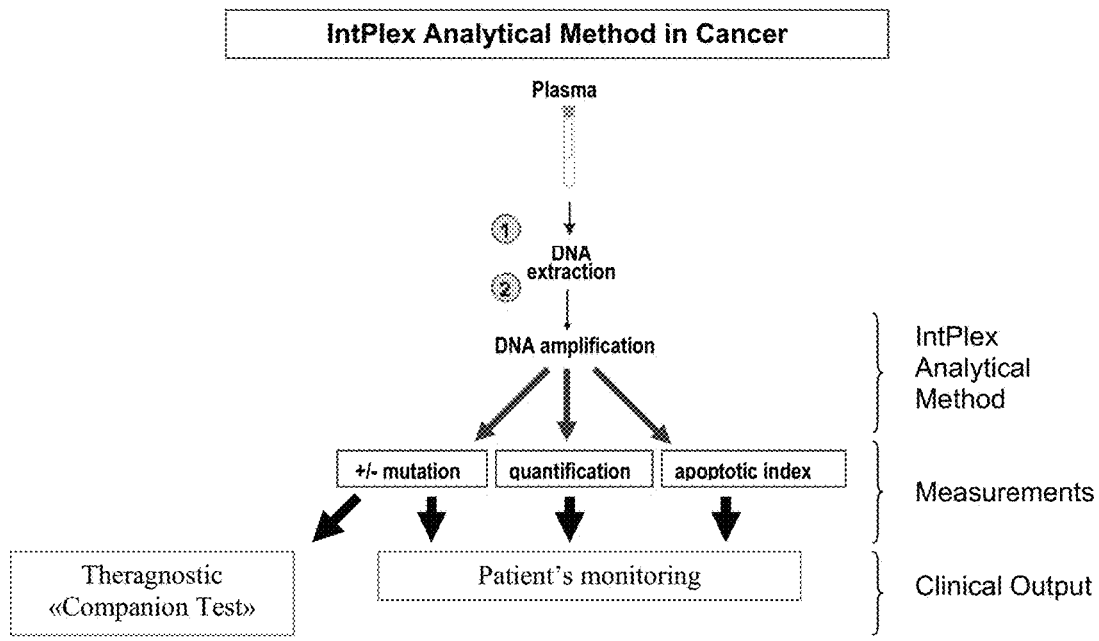

Contribution of the Combination "Mutation Identification/Quantification/Integrity Index" to the Diagnosis of Cancer These three diagnostic parameters can be studied separately, but more sensibly a multiplexed analysis (particularly with the aid of bioinformatics software) will enhance their diagnostic value for the follow-up of cancer patients and their theragnostic value for the individualized therapeutic choice (FIG. 10).

The contribution of these three factors could be modeled using an algorithm that will allow evaluating the risk incurred by each single cancer patient.

As a simple example we can calculate a diagnostic factor as $=([Mi+1] \times (Q+A)$.

Where M, Q and A are risk factor determined by detecting a mutation, quantifying tumoral cirDNA and evaluating a apoptotic index, respectively.

Example V

Examples of Application of the IntPlex Technology

1) Detection of KRAS Mutations in Human Blood Samples in the Context of Cancer Diagnostic The gene RAS (KRAS and NRAS) is subject to somatic mutations in more than 50% of colon tumours and in about 50% of adenomas bigger than 1 cm in diameter. Conversely, it is very rarely mutated in small adenomas (less than 10%). The mutations, generally SNPs, do not interest HRAS, but affect the codons 12 and 13 of KRAS and 12, 13 and 61 of NRAS. The exact role of these mutations is not known. They could transform a small adenoma into a big, dysplastic adenoma, or be present from the beginning in very proliferative cells. The mutations of KRAS are present in 30 to 40% of colorectal tumours.

Thus there is a strong need of a simple and fast test to detect the SNP mutations of KRAS in order to individually orient the patients with CRC towards a targeted anti-EGFR therapy (6). Indeed, the activity of the powerful specific inhibitors of EGFR is blocked when tumour cells carry a mutated KRAS gene. A general consensus has been reached during the annual ASCO meeting in 2008 in which it is advocated that all patients eligible for therapies that target EGFR should first be tested for KRAS mutations before starting a first line therapy (6).

Sequencing DNA obtained from tumour sections represents at the moment the <<gold standard>> for the identification of SNPs. This method is carried out after exeresis, requires the presence of an anatomopathology laboratory and of an analysis laboratory, and it is time-consuming and expensive. CirDNA could be a non-invasive and powerful diagnostic tool if a specific method of analysis could allow its quantification and the detection of mutations in a simple and rigorous way, particularly of the KRAS SNPs in the theragnostic context of the anti-EGFR treatments.

We have thus adapted the IntPlex methodology to the more specific detection of the KRAS SNPs in the theragnostic context of the targeted treatment of CRC. It could bring a response to the urgent clinical need concerning the use of powerful specific inhibitors of EGFR and the mutational status of KRAS.

Figure 4:
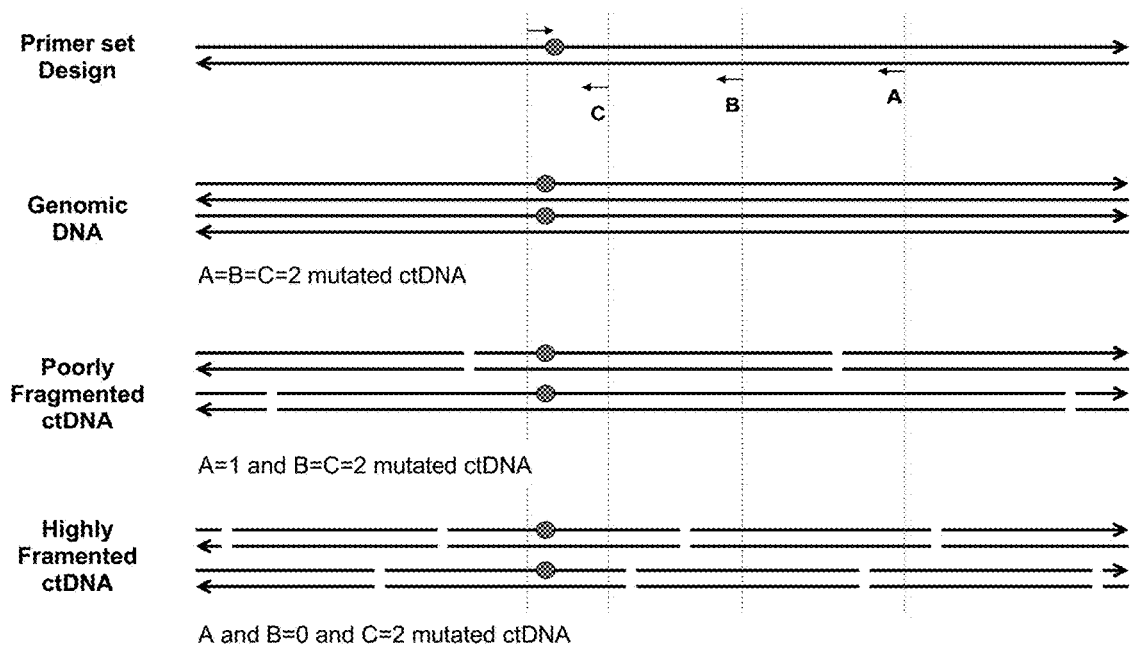

In this system the mutation is located at the 3' end, thus leading to two possible designs: Conventional Intplex and Reverse Intplex. As described before, the Intplex system includes two primer pairs (FIG. 9) that amplify DNA fragments of a size smaller than 100 bp. This amplification gives fragments that are distant 300 bp from one end to the other. This design includes a primer pair for the amplification of the « wild type» sequence that constitutes the reference amplification or standard (A1A2) and another primer pair to amplify the mutated sequence (B1B2) (FIG. 4). It will be possible to determine, by using the "reference" amplicon of exactly the same size and with a sequence in proximity of the other, the percentage of mutated DNA by calculating the ratios: (A1G12Vrev16/B1B2) and (G12Vconv19/A1A2; in the figures the name of the primers is different) (see FIGS. 11 and A), for instance, for the "Reverse" KRAS (Krev) and "Conventional" KRAS (Kconv) systems, respectively. Our previous results have shown the huge importance of the size of the amplicons generated by Q-PCR using a cirDNA sample. Moreover, the Q-PCR analysis of the fragments obtained with the primers A1B2 (size=300 pb) will allows us to determine the integrity index (DNA Integrity Index (DII)) (ratio between long and short fragments). DII indicates the fragmentation status of cirDNA. The integrity index corresponds to the inverse of the apoptosis rate (termed as well the ctDNA fragmentation index).

a) Design of the Q-PCR IntPlex Systems

Conventional Intplex (FIG. 11A) uses the primer G12V typically utilized in the literature for the detection of the KRAS G12V mutation and this primer is a sense oligonucleotide with the mutation localized at its 3' end. Reverse Intplex (FIG. 11B) uses the antisense primer with the mutation at its 3' end. All the primers of these two systems have been selected by software (Material and Methods). The systems Intplex Kconv and Krev have been applied to detect the KRAS mutation G12V. The primers that specifically detect this mutation have been designed to cover the mutated area of the KRAS gene (FIGS. 11A-11B).

The sense primer is conventionally defined as containing a sequence enclosed in the coding DNA strand. The conventional and the reverse Intplex systems differentiate by the sense or the antisense orientation of the mutation targeting primer.

b) Illustration of the Importance of the Size Parameter for the Quantification of cirDNA In this experiment we have tested the two Intplex systems Krev and Kconv using cirDNA isolated from plasma samples of xenografted mice. Sequences of oligonucleotide primers and of chemically modified blocker oligonucleotides specifically designed for the Intplex system towards demonstrating its efficacy and sensitivity or detecting presence of the KRAS G12V or BRAF V600E mutations are presented in Table 2. In this example AS or Q-PCR with using blocker (ASB Q-PCR) method was used. The BRAF and KRAS mutations were detected with using "conventional" and "Inverse" IntPlex systems.

TABLE 2

| Kras B1 conv G12V | 5'-ACTTGTGGTAGTTGGAGCTGT | SEQ ID NO: 9 |
|---|---|---|
| Kras B2 conv | 5'-GAATGGTCCTGCACCAGTAA | SEQ ID NO: 10 |
| Kras conv B1 | 5'-ACTTGTGGTAGTTGGAGCTGG | SEQ ID NO: 11 |
| Kras Conv B2 | 5'-GATTCTGAATTAGCTGTATCGTCAAGG | SEQ ID NO: 12 |
| Kras Conv A1 | 5'-TAAGCGTCGATGGAGGAGTT | SEQ ID NO: 13 |
| Kras Conv A2 | 5'-CCAGTTGACTGCAGACGTGTA | SEQ ID NO: 14 |
| Kras Inv MutG12V | 5'-AACTCTTGCCTACGCCAC | SEQ ID NO: 15 |
| Braf conv A1 | 5'-GGAGAGCAGGATACCACAGC | SEQ ID NO: 16 |
| Braf conv A2 | 5'-AGCAAGCAATCAAAAACTCC | SEQ ID NO: 17 |

TABLE 2-continued

| | | |
|---|---|---|
| Braf inv A1 | 5'-TCATGAAGACCTCACAGTAAAAA | SEQ ID NO: 18 |
| Braf inv A2 V600E | 5'-CACTCCATCGAGATTTCT | SEQ ID NO: 19 |
| Braf inv B1 | 5'-CTAGAAAGTCATTGAAGGTCTCAAC | SEQ ID NO: 20 |
| Braf inv B2 | 5'-TGATTTTTGTGAATACTGGGAAC | SEQ ID NO: 21 |
| Braf V600E blocker | 5'-CCATCGAGATTTCACTGTAGCT-PHO | SEQ ID NO: 22 |

Figure 12:
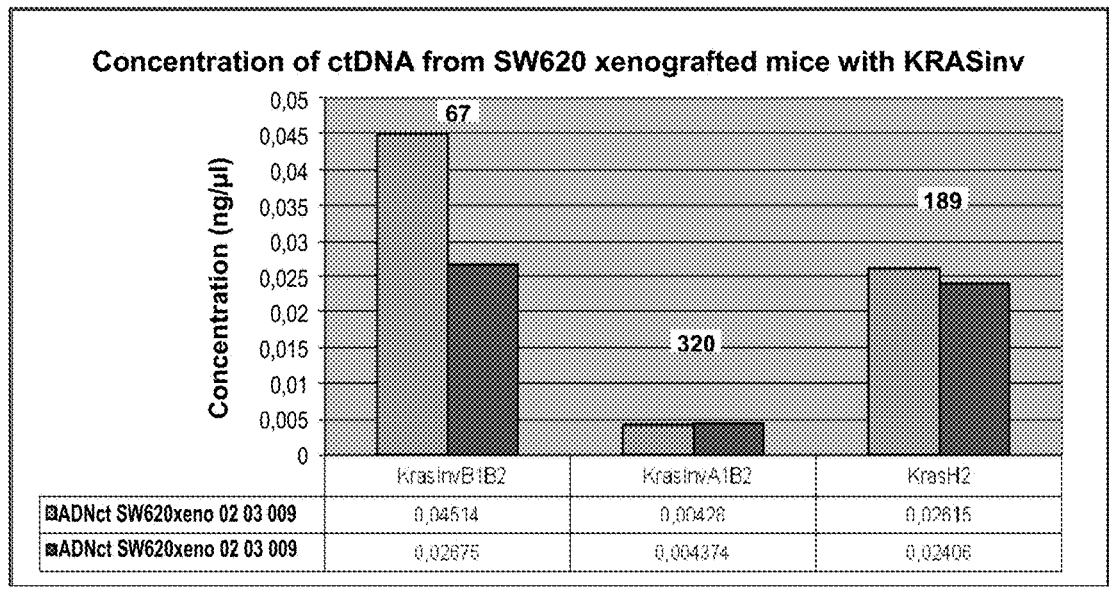
Figure 13:
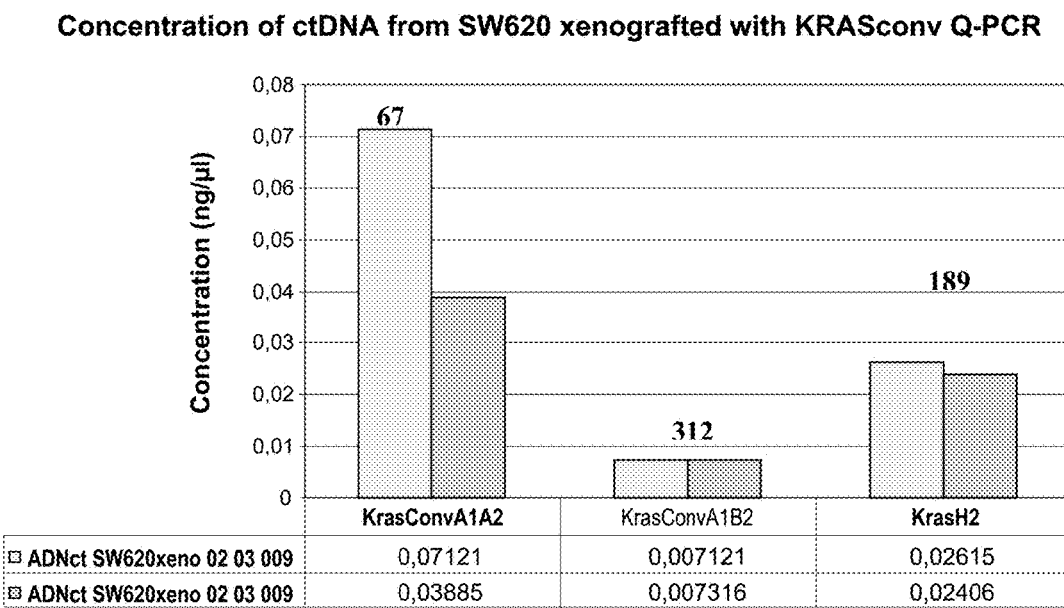

Our results gave identical profiles with both Krev and Kconv (FIGS. 12 and 13).

FIGS. 12 and 13 clearly show that the determination of the concentration of cirDNA is equivalent when the amplicon is of the same size independently from the targeted sequences. Moreover, the results indicate that the value obtained for the 67 bp amplicons (A1A2 and B1B2) is 2.2 times higher and 1.4 times higher than the value obtained for the 189 bp amplicon (KrasH2) and 7.9 times and 9.0 times higher when compared to the values for the 312 and 320 bp amplicons (A1B2) of Kconv and Krev, respectively. Thus, the cross-analysis of these results confirms the accuracy of the cirDNA quantification by Q-PCR with primer systems that generate amplicons of identical sizes and, as a consequence, validates the two systems of analysis Krev and Kconv.

TABLE 3

Apoptosis rate (inverse of index of integrity) of different types of DNA using Krev and Kconv

| DNA | Apoptosis rate Krev | Apoptosis rate Kconv |
|---|---|---|
| Placental genomic DNA | 0.78 | 1.28 |
| Genomic DNA from SW620 cells | 2.00 | 1.92 |
| CirDNA from xenografted mice | 8.33 | 8.34 |

The integrity ratio (inversely relative to the apoptosis rate) corresponds to the ratio between the concentration of short DNA fragments (smaller than 180 bp) and the concentration of long DNA fragments (bigger than 220 bp), i.e. A1B2/B1B2 for Krev and A1B2/A1A2 for Kconv. The apoptosis rate allows an estimate of the proportion of DNA of apoptotic origin and of necrotic origin and thus the determination the origin of cirDNA. With the system Krev we have obtained an apoptosis rate of 0.78 for placental genomic DNA (a DNA which is not released and not mutated) and of 2.00 for mutated DNA of cultured SW620 CRC cells. With the system Kconv we have obtained a rate of 1.28 for placental DNA and 1.92 for DNA from SW620 cells (Table 3).

We have also calculated the apoptosis rate (equivalent to the inverse of the integrity index) of cirDNA isolated from plasma samples of xenografted mice (with SW620 cells that produce tumours) using the two systems Krev and Kconv. With Krev the obtained apoptosis rate was 8.33 and with Kconv 8.34. The apoptosis rate of cirDNA is higher (about 8 and 4 times) than that of genomic DNA (placental DNA and DNA from SW620 cells, respectively). The apoptosis rate might be different when comparing the rates of placental and cell DNA due to their tissue (placenta) and cell origins and thus of the different sampling methods.

Remarkably, the apoptosis rates for the same sample are very similar with the two systems Krev and Kconv, highlighting the robustness of this measure. In addition to the direct comparison of the amplification of two sequences of identical size, this robustness comes from the extreme proximity of such sequences. Although of the same size, a «reference» sequence that is far away from the mutated sequence (localized on another chromosome, for instance) would not allow a similar level of accuracy.

2) Detection of BRAF Mutations in Blood Samples

The gene BRAF is subject to somatic mutations in more than 14% of CRC tumours. The mutation V600E represents more than 90% of the BRAF mutations. Like for the KRAS mutations, the BRAF mutations lead to unefficacy of the anti-EGFR treatment. The assessment of the presence (or not) of this mutation is thus required at the moment of (or more precisely before) the treatment of a patient with metastatic CRC. Therefore, we have designed and developed a Conventional IntPlex system (mutation at the 3' end of the primer B1) for the detection of BRAF mutations in cirDNA (FIG. 14).

Figure 15:
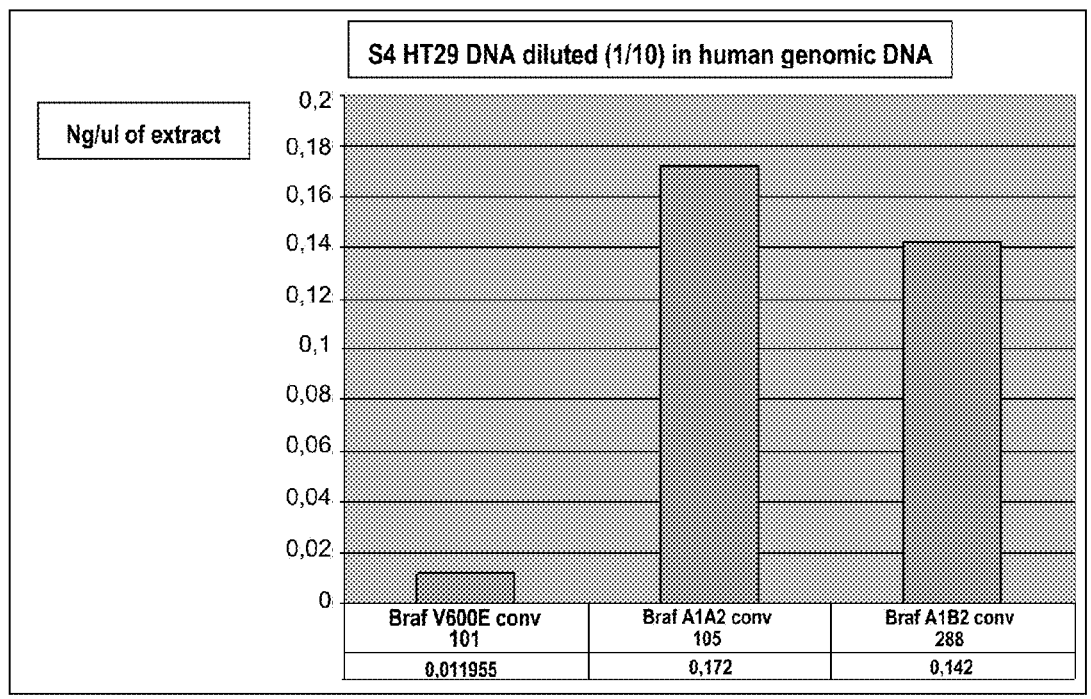

Plasma samples of a mouse xenografted with human CRC HT29 cells that contain in their genome the BRAF mutation V600E have been analysed with this Intplex system (FIG. 15).

Figure 14:
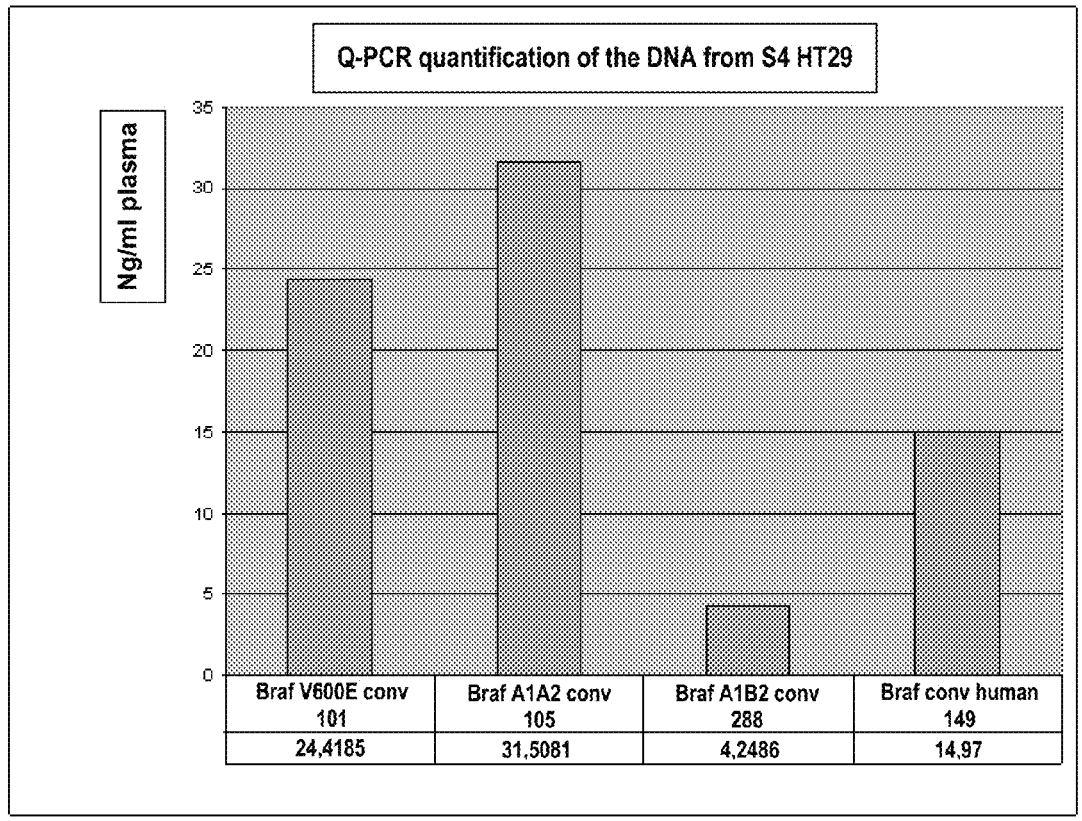

The mean concentration of the short reference amplicon (A1A2) was 31.5 ng/ml and was thus about 8 times higher than that of the long amplicon (4.2 ng/ml) in the cirDNA of the sample S4 HT29 (FIG. 14). Similarly, the concentration of the fragment obtained with the primer pair human WT BRAF was 15 ng/ml and was about 2 times lower than that of the short BRAF amplicon. These results clearly confirm that targeting a short DNA sequence (≤100 bp) produces a more important amplification of cirDNA extracts than targeting longer sequences (149 and 288 bp). The percentage of mutated human DNA relative to the WT reference sequence (A1A2) was 77.5%. It should theoretically have been 50% when taking into account the heterozygosity of the BRAF mutation in this HT29 cell line (only one of the two alleles of the chromosome pair has the mutation). In order to assess the sensitivity of the Intplex system the DNA sample S4 from the plasma of the xenografted mouse was diluted to 1/10 in a sample of placental genomic DNA (FIG. 15). The results summarized in FIG. 15 indicate that the mutated DNA corresponds to 6.95% of the non-mutated DNA and this is approximately 10 times lower than what obtained with the undiluted S4 sample. The amplification of the long sequence is slightly but significantly lower than that of the reference sequence (82.5%).

Figure 16:
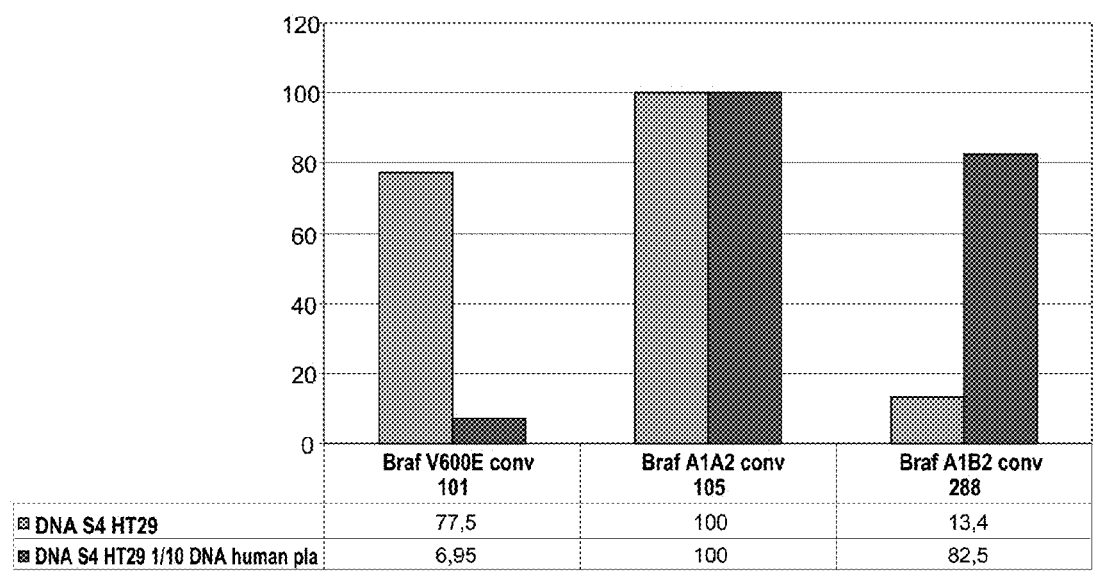

The results (presented as percentages of the concentrations obtained by amplification of the reference sequence A1A2) of these two experiments show the importance of taking into account accurately the size of the amplicons and the validity of the IntPlex system (FIGS. 15 and 16). Indeed, the calculation of the percentage of mutated cirDNA can be dramatically different in function of the system of amplification used as a reference: 77.5% when using a reference of the same size (101 bp) and 56.7% when using a reference of 288 bp. The finding that when cirDNA is diluted in genomic DNA (1/10) the percentage of cirDNA is 6.95% with the reference of the same size and 8.45% with the reference of 288 bp shows that the size parameter is less important when cirDNA is diluted in genomic DNA.

The apoptosis rate varies considerably in function of the quantity of cirDNA because it corresponds to 7.41 in the case of undiluted cirDNA and to 1.21 in the case of diluted cirDNA (i.e., more than 6 times higher). This difference is important in many respects and is characteristic of cirDNAs.

3) Description of the Use of the IntPlex Method for the Analysis of cirDNA in Human Plasma Samples The SNP mutations of KRAS (G12V, G12D, G12C, G13D and G12A) and the BRAF mutation V600E are the cause approximately of 82% of the cases of sporadic mutated CRCs (i.e., 75% of all CRCs). These mutations are present in 94% of patients in whom the KRAS and BRAF mutations are associated with CRC and who do not respond to anti-EGFR therapies (about 50% of all CRCs).

We have adapted the IntPlex technology to the detection of these mutations in cirDNA extracts. Sequences of oligonucleotide primers and of chemically modified blocker oligonucleotides specifically designed for the Intplex system towards detecting presence of the above mentioned mutations are presented in Table 4. In this example AS Q-PCR with using blocker (ASB Q-PCR) method was used. BRAF mutation and the 6 KRAS mutations were detected with using "conventional" and "Inverse" IntPlex ASB Q-PCR systems, respectively.

In CRC1, 68% of the fragments of cirDNA carry the mutation KRAS G12V, whereas the percentage for the other KRAS mutations does not go above 1.2% for this patient.

In CRC2, 0 to 6.6% of the cirDNA fragments appear to carry BRAF or KRAS mutations.

In HHP1, 0 to 3.2% of the cirDNA fragments appear to carry BRAF or KRAS mutations.

CRC2 data show significant % of apparently mutated cirDNA but the level appears the same for 4 mutations. Given the fact that, with the exception of very rare cases, these mutations are mutually exclusive the threshold of the % mutated cirDNA for specifically defining the mutational status is not reached in the case of CRC2. Thus values obtained for quantifying mutated cirDNA in CRC2 plasma correspond to non-specific effect. The positivity threshold could be fixed at least at 7% here, but a study using an important number of samples is needed in order to determine it for each mutation. Moreover, an algorithm could be used to integrate the threshold within a sample in order to estimate the discrimination of the percentage of a mutation relative to the percentage of the others. Nevertheless, this figure shows that only CRC1 carries a mutation (G12V).

Remarkably, these results and other on various clinical samples (not shown) show that the proportion of fragments of mutated cirDNA appears to be extremely high (between 17% and 70%) when compared to the results described in the literature (on average 1% and never higher than 10%) (5, 7). This illustrates the capacity of our method to produce a sensitive and specific analysis of tumour cirDNA and its innovative character.

As a consequence CRC1 patient in contrast to CRC2 patient can not unfortunately be treated with EGFR inhibitor.

TABLE 4

| Braf conv A1v1 | 5'-TTATTGACTCTAAGAGGAAAGATGAA | SEQ ID NO: 23 |
| --- | --- | --- |
| Braf conv A2v2 | 5'-GAGCAAGCATTATGAAGAGTTTAGG | SEQ ID NO: 24 |
| Braf conv B2 | 5'-TAGCCTCAATTCTTACCATCCACA | SEQ ID NO: 25 |
| Braf conv B1 V600E | 5'-GATTTTGGTCTAGCTACAGA | SEQ ID NO: 26 |
| Braf conv V600E Blocker | 5'-GCTACAGTGAAATCTCGATGG-PHO | SEQ ID NO: 27 |
| Kras Inv A1 6126 | 5'-GCCTGCTGAAAATGACTGA | SEQ ID NO: 28 |
| Kras Inv B1 6379 | 5'-CCTTGGGTTTCAAGTTATATG | SEQ ID NO: 29 |
| Kras Inv B2 6445 | 5'-CCCTGACATACTCCCAAGGA | SEQ ID NO: 30 |
| Kras Inv A2 MutG12V16 | 5'-CTCTTGCCTACGCCAA | SEQ ID NO: 31 |
| Kras Inv A2 MutG13D64 | 5'-GCACTCTTGCCTACGT | SEQ ID NO: 32 |
| Kras Inv A2 G12D low | 5'-CTCTTGCCTACGCCAT | SEQ ID NO: 33 |
| Kras Inv A2 G12A low | 5'-CTCTTGCCTACGCCAG | SEQ ID NO: 34 |
| Kras Inv A2 G12S low | 5'-TCTTGCCTACGCCACT | SEQ ID NO: 35 |
| Kras Inv A2 G12C low | 5'-TCTTGCCTACGCCACA | SEQ ID NO: 36 |
| Kras Inv mut Blocker | 5'-GCCTACGCCACCAGCTC-PHO | SEQ ID NO: 37 |

Figure 17:
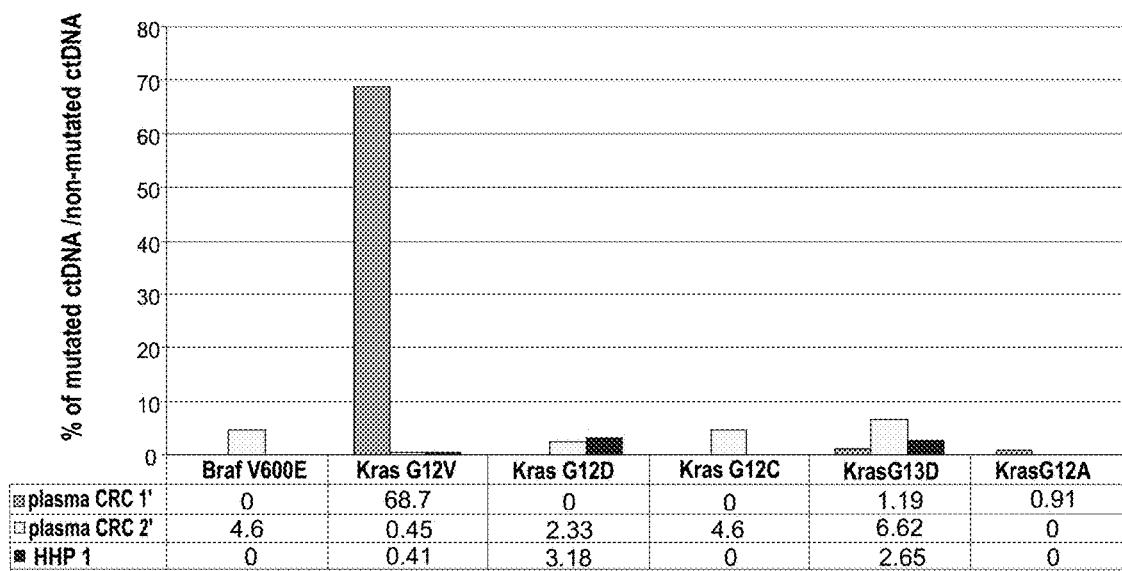

As an example, FIG. 17 shows the results obtained with plasma samples from a patient with CRC who apparently carried the KRAS mutation G12V (CRC1), a CRC patient who did not seem to have that mutation (CRC2) and a healthy individual (HHP1).

Thus this adapted Intplex method which is part of the present invention appears to be a simple method for the analysis of cirDNAs based on the accurate knowledge of their size population. It relies on a precise choice of oligonucleotide primers that allow their direct analysis in one single step of Q-PCR. Three independent sets of data from the analysis of circulating nucleic acids (NA) (1. detection of mutation(s), 2. exact quantification of the tumoral and total cirDNA concentration and 3. estimate of a ratio concerning the apoptotic origin of the cirDNA) can be integrated in the same test.

Example VI

CirDNA Concentration Profiles for HHP and CRC Subjects

CirDNA concentrations were determined from plasma samples from three CRC patients and three healthy individuals by q-PCR with using the primer sets amplifying fragment of 60, 73, 101, 145, 185, 249, 300, 357, 409 bp, as previously described. Concentration profiles obtained are specific to either CRC or healthy subjects for all of them. Mean maximal value was 6.19 and 943.59 ng/ml plasma for HHP and CRC subjects, respectively. The highest discrimination by calculating the ratio of HHP/CRC integrity index was obtained when using the 300/60 and 300/73 ratio (8.18 and 10.07, respectively), confirming the previous data. Ratio of 409/60 apparently is the highest but it was arbitrarily not considered since concentration obtained by amplifying the 409 fragment in CRC plasma is near the analysis sensitivity. By subtracting the concentration obtained by one fragment size amplification from the following, respective to increasing size, the % of the amount of the cirDNA within the 60-409 bp range between both successive amplicon sizes can be estimated (Given Cn the concentration of ctDNA when detecting an amplified fragment of a size n and Cn+1 the cirDNA concentration when detecting the amplified fragment of the proximate higher size in the increasing amplified fragment size serie, the concentration existing between both size is calculated as Cn-Cn+1).

Figure 18B:
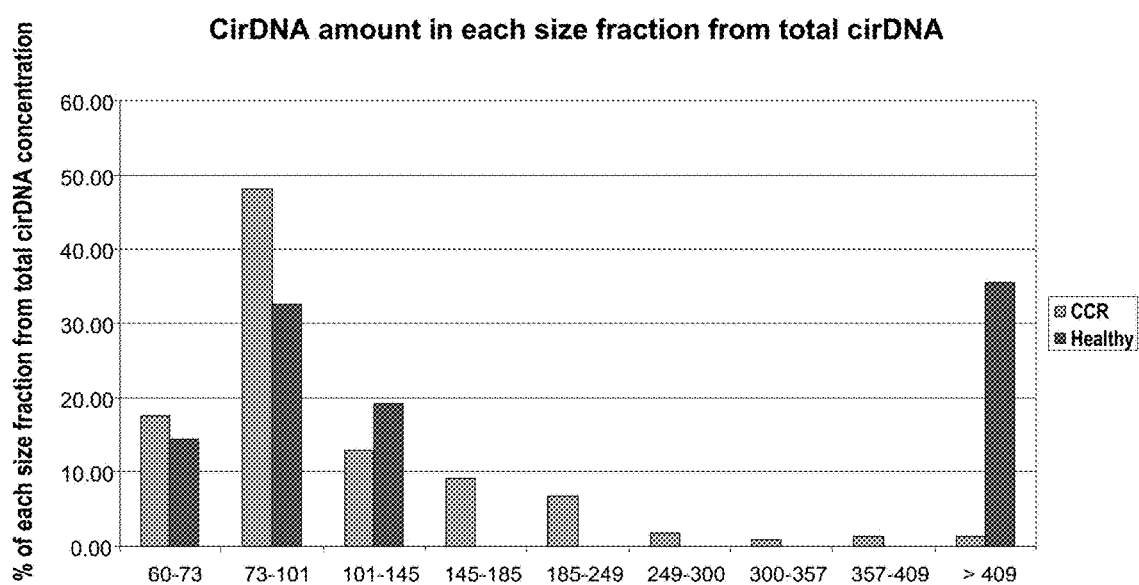

Values expressed in % of ctDNA vs ctDNA length fraction (range) are presented in histograms in FIG. 18. Data suggest that CRC and HHP plasmas present same profile of cirDNA amount in the 60-73, 73-101 and 101-145 bp ranges with noticeably higher level for CRC plasma in the 73-101 range. In contrast to the absence of HHP cirDNA from 145-185 to 357-409 bp ranges, cirDNA level is significantly detected, decreasing from 9 to 2%. High proportion (35%) was found for cirDNA from HHP of size higher than 409 bp, in contrast to the very low level determined for CRC cirDNA (2%).

Clearly, these data show high discrimination between HHP and CRC plasmas which is not expected from man of the art for the time being.

Example VII

Parameters for Logistic Function Proposed in a Method for Diagnosis or Prognosis a Pathological or Physiological State, Such as the Presence of a Tumor or Tumor Progression in a Patient, Said Pathological or Physiological State being Associated to a SNP Gene Marker (i.e Presence of a Mutation Associated to a Cancer)

Values which can been combined for through a logistic function including at least two biomarker in order to obtain a end value which is relevant of the nature of the diagnosis or the prognosis (See FIG. 9)

$$(A1A2)=(B1B2)=X$$

$$(A1B2)=Y$$

With X<180 and Y>X
Ideally: 50<X<100 and 200<Y<350
Where:
B1B2 is defined as the sequence that contains the genetic polymorphism (such as SNP or mutation)
A1A2 is defined as the sequence that does not contain a genetic polymorphism (such as SNP or mutation) and is localized on the same DNA strand
The numbers correspond to the number of nucleotides of the amplified sequence (amplicon)
X and Y are the distance on the genomic DNA between the 5' ends of the primers used for amplifying the short and the longer amplicon, respectively.
These biomarkers allow:
1. The qualitative detection of the presence of a genetic polymorphism (such as SNP or mutation) by determining the % B1B2/A1A2 at a higher level than a specific threshold for each genetic polymorphism primer sets.
With B1B2 defined as the sequence that contains the genetic polymorphism (such as SNP or mutation).
2. The specific quantification of total and tumoral cirDNA: A1A2 and B1B2 quantity, respectively.
3. The evaluation of the DNA fragmentation index (in the present invention, the wording "apoptosis rate", "DNA fragmentation index" and "integrity index" have the same meaning): % B1B2 or A1A2/A1B2.
The applicability to all circulating nucleic acids (DNA, RNA, siRNA, miRNA, . . . ).
The use of nucleic acid of specific length, for instance <180 bp and ideally <100 bp, as nucleic acid standard for the Q-PCR calibration.

Example VIII

Demonstration that ctDNA of Size Below 100 bp are of Significant Proportion and that the Previously Established Hypothesis Based on Electrophoresis Analysis is Wrong Agarose gel electrophoresis of 20 μg of ctDNA extracted from two CRC patients (CRC021 and CRC019). Ladder are made of multiple of 100 bp DNA fragments. Portions of the gel were removed just after the end of the run. For CRC021 one portion of the gel corresponding to 10 to 440 bp were removed and subjected to Q-PCR. For CRC019 two portions of the gel corresponding to 30 to 130 and 130 to 500 bp were removed and subjected to Q-PCR. Conditions of Q-PCR analysis was performed as described earlier when quantifying ctDNA and detecting the 73 bp, 145 bp and 300 bp amplicon of the KRAS intron as previously described.

In CRC021 plasma, 47% of total ctDNA were found between 73 and 145 bp while 36% and 17% were found in the 145-300 and >300 bp ranges, respectively.

In CRC019 plasma, 61% of total ctDNA were found between 73 and 145 bp while 35% and 5% were found in the 145-300 and >300 bp ranges, respectively. In the gel portion between 30 and 130 bp 57% of total ctDNA was observed (see FIGS. 19A and 19B).

These data prove that ctDNA of size lower than 180 bp and in particular lower than 100 bp exist in a significant amount. Thus electrophoresis is not an appropriate analytical method to appreciate ctDNA size. This is the first demonstration that the previously established hypothesis based on electrophoresis analysis which apparently showed that ctDNA are of size higher than 180 bp, is wrong.

We postulate that ctDNA fragments of size below 180 bp are not visible following electrophoresis and labelling with fluorescent dye because they are below the signal threshold owing to:
1. ctDNA fragments below 180 bp might vary from one nucleotide from another leading to low local concentration at on precise size;
2. the fluorescent dye such as the Sybre green, have a maximal level of intercalation (i.e. one Sybre green molecule every 23 nucleotides) drastically limiting signal intensity of low size ctDNA. For instance, a 69 bp DNA fragment has 3-fold less signal than that of 207 bp fragment.

Example IX

Figure 20:
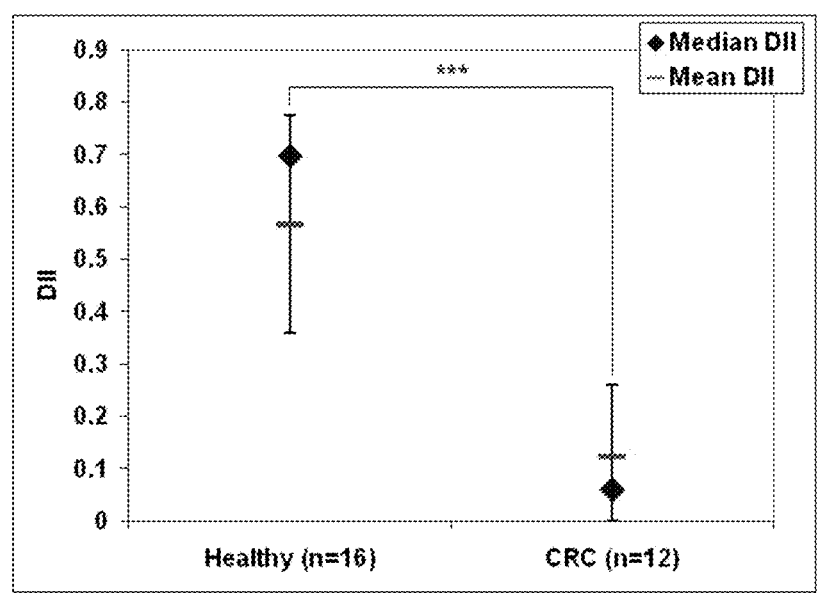

DII as Determined from the ctDNA Concentration of ctDNA of Size Below 100 bp, Such as 60 bp, Significantly Discriminate Healthy and CRC Individuals Comparison of the DII values (Table 5) from genomic DNA, and ctDNA from mice plasma (non-xenografted and xenografted) and (see FIG. 20) from human plasmas (healthy and CRC). The DII was estimated by the ratio of the concentration obtained by targeting a 300 bp sequence and a 60 bp sequence in a KRAS region. DII mean value of HHP (n=16) is significatively different from DII mean value of CRC (n=12) (mean, 0.565 and 0.122, respectively; p<0.001). A similar difference was observed in the animal model where mean DII is 0.447 for healthy plasma ctDNA (n=9), 0.645 for non tumour-derived ctDNA (n=9) and 0.027 for tumour derived ctDNA (n=9).

This buttress the discovery of detecting amplicon of size lower than 100 bp in particular 60 bp as used here for determining a DII.

TABLE 5

Comparison of the DII values from genomic DNA, and ctDNA from mice plasma (non-xenografted and xenografted)

|  |  | mean DII |
| --- | --- | --- |
| Genomic DNA |  |  |
|  | SW620 cells | 1.120 |
|  | Human placental DNA | 0.720 |
| Circulating DNA |  |  |
| Animal model | Healthy mice (n = 9) | 0.447 |
|  | Non tumor derived ctDNA from xenografted mice (n = 9) | 0.645 |
|  | Tumor derived ctDNA from xenografted mice (n = 9) | 0.027 |
| Human individuals | Healthy (n = 16) | 0.565 |
|  | CRC (n = 12) | 0.122 |

Example X

DII Calculated with the Primer Design of the Invention and in Various Gene Regions Show High Accuracy and Low Variability There are two configurations about the design of the primers used in the multiplex method according to the invention: conv and inv. Here we determined the DII from a CRC patient plasma with using the conv and the inv configuration in the KRAS and BRAF region (containing the 2th exon hot spot mutation and the V600E, respectively), the conv configuration in the 2th intron of the KRAS gene (BRAF conv). We have compared those DII with that calculated in distant region within the same gene (long KRASconv/short KRAS int, representing the ratio of the concentration obtained with using the primer pair leading to the amplification of the long sequence as used in KRAS conv to that obtained with using the primer pair leading to the amplification of the short sequence as used in KRAS int) and with that calculated in distant region of two different genes (long KRASconv/short BRAF inv, representing the ratio of the concentration obtained with using the primer pair leading to the amplification of the long sequence as used in KRAS conv to that obtained with using the primer pair leading to the amplification of the short sequence as used in BRAF inv).

Figure 21:
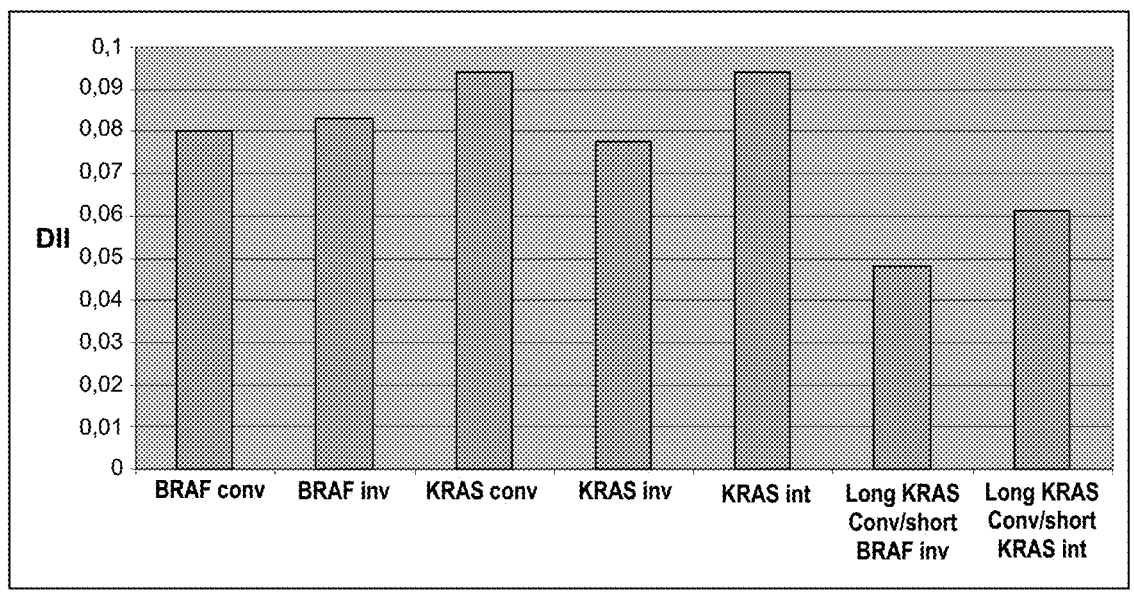

First, data clearly demonstrate first the high accuracy and low variability of the DII value calculated upon our invention whatever the gene region, owing DII value vary from 0.077 to 0.094 (coefficient of correlation=9.1%) (see FIG. 21).

Second, the value obtained with using primer pairs targeting distant DNA sequences either within the same gene or different genes are different and more precisely significantly lower (0.061 and 0.048, respectively) than those found according the primer designs of the invention.

Maximal coefficient of correlation of the value from the Q-PCR analysis and DNA extraction, under the previously described experimental conditions, is 23% (n=12).

Example XI

Determination of Various Indexes Involving the Amount of the ctDNA Size Fraction Below 100 bp Various indexes were determined from data presented in FIG. 18. Those indexes were calculated from different size fraction (see table 6).

TABLE 6

|  | CRC | HHP | Fold difference |
| --- | --- | --- | --- |
| % <100 bp | 65% | 46% | 1.4 |
| DII 300/60 | 0.025 | 0.355 | 14.2 |
| SFR 409/<100 | 0.038 | 0.770 | 20.3 |
| SFR <100/145-409 | 3.3 | 460 | 139.0 |

% <100 bp, percentage of ctDNA fragments of size below 100 bp (more precisely from the 60-100 bp fraction);
DII 300/60, ratio of the concentration of ctDNA fragments of size higher than 300bp to that of total ctDNA;
SFR 409/<100, ratio of the concentration of ctDNA fragments of size higher than 409 bp to that of the concentration of 60-100 bp fraction;
SFR <100/145-409, ratio of the concentration of ctDNA fragments of the 60-100 bp fraction to that of ctDNA fragments of the 145-409 bp fraction.

Data clearly show that determining the concentration of ctDNA fraction below 100 bp is of great interest and makes possible to largely discriminate between plasma of CRC patients and healthy subjects. Second, the use of ratio of ctDNA size fraction such as SFR greatly helps towards this goal.

Example XII

Determination of Various Parameters, Such as SFR, Indicative of ctDNA Fragment Size Pattern We studied the size pattern of mutated ctDNA in comparison with that of non-mutated ctDNA. Towards this goal we used a set of primers amplifying increased target size within the same region. This set generates the amplification of sequences on the hot spot region of the KRAS gene (12 and 13th codon of the 2nd exon) where the forward primer for every primer pair is designed to specifically target a point mutation of this region or the wild type sequence (See Table 7 below and FIGS. 22A-22E). These sets were cautiously selected to promote high sensibility and high specificity for quantifying either mutated or not mutated target sequences (see Table 8 below).

TABLE 7

| Samples | Q-PCR target | <138% | 138< >300% | >300% | DII | SFR |
|---|---|---|---|---|---|---|
| Healthy (n = 9) | KRAS intron | 66.20 | 0 | 37.90 | 0.45 | 20 |
| CRC4 | mut. KRAS 2th exon | 70.11 | 23.60 | 6.41 | 0.06 | 2.97 |
| CRC5 | mut. KRAS 2th exon | 74.10 | 17.90 | 8.00 | 0.08 | 4.14 |

TABLE 7-continued

| Samples | Q-PCR target | <138% | 138< >300% | >300% | DII | SFR |
|---|---|---|---|---|---|---|
| CRC6 | mut. KRAS 2th exon | 89.20 | 6.00 | 4.80 | 0.05 | 14.87 |
| CRC14 | mut. KRAS 2th exon | 52.11 | 30.21 | 17.60 | 0.18 | 1.73 |
| CRC4 | wt. KRAS 2th exon | 10.62 | 77.76 | 11.69 | 0.12 | 0.14 |
| CRC5 | wt. KRAS 2th exon | 0 | 89.00 | 11.10 | 0.11 | 0 |
| CRC6 | wt. KRAS 2th exon | 0 | 77.10 | 30.10 | 0.30 | 0 |
| CRC14 | wt. KRAS 2th exon | 18.36 | 49.77 | 32.04 | 0.32 | 0.37 |

Primers used to carry out this experiment are: (see Table 8):

TABLE 8

| | | | | Sequence (SEQ ID NO:) | |
|---|---|---|---|---|---|
| Human | KRAS | Kras 60 Hf | sense | GCCTGTGACCTACAGTGAAAA (220) | 60 |
| | | Kras 73 Hf | sense | CCCTACACGTAGAGCCTGTGA (221) | 73 |
| | | Kras 101 Hf | sense | GAGATGGTGGAAGAACAGGTG (222) | 101 |
| | | Kras 145 Hf | sense | TGGGCTGTGACATTGCTG (223) | 145 |
| | | Kras 185 Hf | sense | ATCTGCCTCCGAGTTCCTG (224) | 185 |
| | | Kras 249 Hf | sense | TGGAAGAGCATAGGAAAGTGC (225) | 249 |
| | | Kras 300 Hf | sense | GGTCCTTTTCCGTGTGTAGG (226) | 300 |
| | | Kras 357 Hf | sense | GGCATCTCTAGGACGAAGGT (227) | 357 |
| | | Kras 409 Hf | sense | GCCTCCCTTTCCAGCACT (228) | 409 |
| | | Kras 145-300 Hr | antisense | TGACCAAGCAAAACAGACCA (229) | — |
| Human | KRAS | Kras 46 Hr | antisense | GCTGTATCGTCAAGGCACTC (230) | 46 |
| | | Kras 82 Hr | antisense | TTGGATCATATTCGTCCACAA (231) | 82 |
| | | Kras 138 Hr | antisense | CAAAGAATGGTCCTGCACC (232) | 138 |
| | | Kras 200 Hr | antisense | TGAAAATGGTCAGAGAAACCTT (233) | 200 |
| | | Kras 250 Hr | antisense | TGAAACCCAAGGTACATTTCAG (234) | 250 |
| | | Kras 300 Hr | antisense | GAACATCATGGACCCTGACA (235) | 300 |
| | | Kras 350 Hr | antisense | TTCTACCCTCTCACGAAACTCTG (236) | 355 |
| | | Kras 400 Hr | antisense | AAAGATTGTCTTTTAGGTCCAGATAGG (237) | 390 |
| | | KrasNonMutated Hf | sense | GTAGTTGGAGCTGGTGGC (238) | — |
| | | Kras G13D Hf | sense | GTAGTTGGAGCTGGTGA (239) | — |
| | | Kras G12V Hf | sense | TTGTGGTAGTTGGAGCTGT (240) | — |
| | | Kras G12D Hf | sense | TGTGGTAGTTGGAGCTGA (241) | — |
| | | Kras G12S Hf | sense | ACTTGTGGTAGTTGGAGCTA (242) | — |
| | | Kras G12A Hf | sense | TGTGGTAGTTGGAGCTGC (243) | — |

We then determined the % of mutated ctDNA by determining the concentration with using the primer set amplifying the shorter target (82 bp) from the total ctDNA concentration (being the sum of the concentration of the mutated and the non mutated ctDNA).

Determination of various parameters indicative of ctDNA fragment size pattern. a, data are presented in a table (Table 7) or plotted in histograms (See FIG. 22A-22E). Size fraction is expressed as % to the highest value obtained in each set. The proportion of ctDNA fragments <138 bp or 145 bp was determined by subtracting the concentration determined by using the primer set amplifying the 82 bp target to that of using the primer set amplifying the 138 bp target. When the value is negative data is arbitrarily expressed as 0. The proportion of ctDNA fragments >300 bp was determined by using the primer set amplifying the 300 bp target. The ctDNA integrity index (DII) was determined by calculating the ratio of the concentration determined by using the primer set amplifying the 300 bp target to the concentration determined by using the primer set amplifying the 82 bp target. The size fraction ratio (SFR) was determined by calculating the ratio of the concentration of fragments <138 or 145 bp to the concentration of fragments between 138-145 bp and 300 bp. Number under the histograms: 4,5,6,14, plasmas from CRC patients with positive mutational status for KRAS (CRC4-6 and CRC14). H, healthy individuals (n=9).

The proportion of various ctDNA size fractions, the integrity index and a size fraction ratio (we termed SFR) of the human plasmas from healthy individuals, and from four CRC patients with a KRAS point mutation are summarized in figure. Mutant ctDNA are mostly composed of fragments <138 bp while non mutant ctDNA are mostly constituted of fragments in the 138-300 bp range and very poorly of fragments <138 bp. alternatively, ctDNA of healthy individuals seem clearly constituted of fragment <138 bp and >300 bp with no apparent fragment between 138 and 300 bp.

Data clearly show that ctDNA size fraction analysis especially by determining size fraction ratio, such as the SFR we calculated in this study, might help in distinguishing KRAS mutated vs. non mutated ctDNA. In addition, size fraction analysis could disclose indication about the nature of the ctDNA release mechanism. Nonetheless, data suggest that non tumour-derived ctDNA in CRC patient might mainly originate from apoptosis in contrast to ctDNA from healthy individuals and to a lesser extent tumour-derived ctDNA. Calculation of such indexes should facilitate size pattern analysis since amplification experiments with serial nested Q-PCR as performed here is time consuming.

Example XIII

Comparison of the Determination of the % Mutated Fragments from Total ctDNA Upon the Use of the Amplicon Length The quantification of ctDNA was determined by amplifying increasing size targets of 82, 138, 300 bp (see Table 9) from the plasma of patients with tumour cells bearing the KRAS G12D, KRAS G12D and KRAS G13D mutation in CRC40, CRC50 and CRC60, respectively. Mutated ctDNA quantification was performed with primer pairs constituted of the same reverse primer containing in 3' the mutation and of primers targeting region distant to 82,138 and 300 bp from both 5' extremities. Non mutated ctDNA was quantified with using the same forward primers and the same reverse primer with wild type sequence (data from previous example . . . ). Total ctDNA corresponds to the sum of the mutated fragments to the non mutated fragments.

Clearly data show that the determination of the % of mutant ctDNA fragments vary upon the size of the amplicon detected, and demonstrate that quantifying mutant ctDNA fragments is much higher when amplicon size is lower than 100 bp. This leads to a more accurate detection of the presence of a mutation from ctDNA by determining the percentage of mutants fragments; a positive detection being determined when this value is above the percentage of a threshold. There is for each CRC plasma about 2.5, 3.4 and 6.3-fold increase of the % mutated when detecting the 82 bp amplicon as compared with detecting 138 bp amplicon while the proportion in % of ctDNA on which the value is calculated was 3.3, 3.9 and 9.3 fold higher, in CRC4, CRC5 and CRC6, respectively (see Table 9).

TABLE 9

|  | % mutated from total ctDNA | proportion in % of ctDNA on which the value is calculated |
|---|---|---|
| CRC4, G12D | | |
| KRAS 82 bp | 26.0 | 100.0 |
| KRAS 138 bp | 10.5 | 29.9 |
| KRAS 300 bp | 15.9 | 6.4 |
| CRC5, G12D | | |
| Kras 82 pb | 17.4 | 100.0 |
| Kras 138 pb | 5.1 | 25.9 |
| CRC6, G13D | | |
| Kras 82 pb | 52.7 | 100.0 |
| Kras 138 pb | 8.3 | 10.8 |

Example XIV

Additional Data Showing the Full Agreement Between KRAS Mutational Status Determined by Biopsie Sequencing and by the Method Based on ctDNA According to the Invention (See Table 10)

TABLE 10

| Sample | Clinical status | KRAS Status Sequencing | KRAS Status Intplex |
|---|---|---|---|
| CRC 1 | metastatic ADK rectum; progression under chimio | WT | WT |
| CRC 2 | metastatic ADK rectum; 3 meta foie | KRAS mutated | KRAS mutated |
| CRC 3 | metastatic ADK rectum; progression under chimio | WT | WT |
| CRC 4 | metastatic ADK colon; progression under chimio | KRAS mutated | KRAS mutated |
| CRC 5 | metastatic ADK colon; progression meta | WT | WT |
| CRC 6 | metastatic ADK rectum; progression meta | WT | WT |
| CRC 7 | metastatic ADK colon; progression meta, Stage IV | WT | T |
| CRC 8 | metastatic ADK rectum; progression under chimio | WT | WT |
| CRC 9 | metastatic ADK rectum; progression under chimio | WT | WT |
| CRC 10 | metastatic ADK colon; progression meta, Stage IV | G12D | G12D |

Example XV

DII Calculated with ctDNA Quantification from the Detection of Amplicons of Various Size TABLE 11 and TABLE 12

| Xenografted mice | | | | | | | |
|---|---|---|---|---|---|---|---|
| DII | 300/150 | 300/100 | 250/101 | 250/150 | 249/60 | 300/60 | 357/60 |
| tumor-derived | 0.251 | 0.094 | 0.106 | 0.284 | 0.03 | 0.007 | 0.024 |
| non tumor-derived | 0.959 | 0.404 | 0.441 | 1.046 | 0.429 | 0.645 | 0.517 |
| control | 0.722 | 0.353 | 0.502 | 1.027 | 0.279 | 0.447 | 0.426 |
| DII ratio control/tumor-derived | 2.87 | 3.75 | 4.73 | 3.62 | 9.3 | 63.86 | 17.75 |
| | | | | | | | |
| Clinical samples | 300/101 | 300/145 | 300/185 | | 249/73 | 249/101 | 249/145 |
| | | | | | | | |
| DII ratio HHP/CCR | 5.84 | 5.44 | 3.84 | | 6.12 | 4.88 | 4.18 |
| DII ratio HHP/CCR | 73/60 | 101/60 | 145/60 | 185/60 | 249/60 | 300/60 | 357/60 | 409/60 |
| | 0.99 | 1.37 | 1.47 | 2.56 | 5.9 | 8.18 | 7.8 | 13.88 |
| DII ratio HHP/CCR | | 101/73 | 145/73 | 185/73 | 249/73 | 300/73 | 357/73 | 409/73 |
| | | 1.49 | 1.52 | 2.7 | 7.34 | 10.07 | 7.95 | 20.64 |

We determined DII with PCR amplification of various short and long sequences from the animal experiment (see Table 11 below and Examples above) and the size profiling of ctDNA of clinical samples (see Table 12 below and Examples above).

If we consider that the concentration determined by detecting the short amplicon such as 60 bp corresponds to the total ctDNA concentration, the DII corresponds to the % of the fraction of the ctDNA of size higher than the long amplicon.

Data show that the highest difference between healthy and CRC plasmas were observed when calculating the DII with detecting amplicon of size <100 bp such as 60 or 73 bp and amplicon of size >249 bp. The DII calculated from the mouse experiment confirm this observation.

When compared, more precisely, with DII which are calculated with using the Q-PCR detection of amplicon of size higher than 100 bp, such as 101 or 145 bp, DII calculated with 60 or 73 bp are about 1.5 fold lower in clinical samples and are about 17-fold lower in xenografted mice. Thus use of detection of amplicon size lower than 100 bp and in particular lower than 73 bp, allows a higher discrimination between healthy individuals and CRC patients.

To note the use of the fraction >409 bp showed higher discrimination between CRC and healthy individuals than the use of the fraction >300 bp.

Example XVI

Description of the DNA Regions Located Downstream or Upstream of a Mutation when Using the Method According to the Present Invention to Detect a Mutation (Particularly the Said IntPlex Method)

Numerous reports described targeting the region located downstream or upstream of a mutation when proposing to detect a mutation. For instance, various primers (18 to 30 nucleotides) were designed to hybridize with the DNA sequence corresponding to that region. Here we claim to protect the use of molecular entities targeting other regions according to the description of the design of the primers used for that method (FIG. 11) in either the conv or rev configuration (respectively conventional and inverse (inv) configuration, named also conv and rev (or inv) design for the molecular entities associated respectively with these conv and inv configurations). We can describe those regions from the mutation to be detected given the following parameters:

primer minimal size=15 nucleotides primer maximal size=30 nucleotides spacing between 2 primers (between the 3' extremities of both primer)=5 bp amplicon size range for A1A2 or B1B2=35 to 100 bp A1B2 being in the 250-450 bp size range In the case of the conv design, as presented in FIG. 11A, the molecular entities to be protected are those which target:

the region where the B2 primer should hybridize and which is located from 5 to 85 nucleotides downstream from the position of the mutation in the non sense DNA strand.

the region where the primer pair A1A2 can be designed within the 430-100 nucleotides upstream from the position of the mutation to be detected.

In the case of the inv design, as presented in FIG. 11B, the molecular entities to be protected are those which target:

the region where the A1 primer should hybridize and which is located from 5 to 85 nucleotides upstream from the position of the mutation in the non sense DNA strand.

the region where the primer pair B1B2 can be designed within the 100-430 nucleotides downstream from the position of the mutation to be detected.

A) Example of DNA Region to be Targeted Upon Our Method when BRAF V600E Point Mutation is of Interest a) See FIG. 23 which shows the regions where molecular entities such as primers could target upon our multiplex method applied to this mutation.

Selected oligonucleotides useful for that method applied to this mutation (see Tables 13 and 14).

b) Selected oligonucleotides for B2 primers for BRAF convention system (see Table 13)

TABLE 13

Primer B1
B1: GATTTTGGTCTAGCTACAG (SEQ ID NO. 38)
Or containing the mutation region:
Primer B2:

| Starting Region | Sequence | SEQ ID NO. |
|---|---|---|
| 172098 | ATTCTTACCATCCACAAAATGG | 40 |
| 172105 | AGCCTCAATTCTTACCATCCA | 41 |
| 172104 | GCCTCAATTCTTACCATCCA | 42 |
| 172104 | GCCTCAATTCTTACCATCCAC | 44 |
| 172105 | AGCCTCAATTCTTACCATCCAC | 45 |
| 172103 | CCTCAATTCTTACCATCCACAA | 46 |
| 172118 | TCAGTGGAAAAATAGCCTCAA | 47 |
| 172117 | CAGTGGAAAAATAGCCTCAATTC | 48 |
| 172117 | CAGTGGAAAAATAGCCTCAATTCT | 49 |
| 172119 | ATCAGTGGAAAAATAGCCTCAA | 50 |
| 172118 | TCAGTGGAAAAATAGCCTCAAT | 51 |
| 172497 | TTTCAACAGGGTACACAGAACA | 52 |
| 172491 | CAGGGTACACAGAACATTTTGAA | 53 |
| 172489 | GGGTACACAGAACATTTTGAACA | 54 |
| 172493 | AACAGGGTACACAGAACATTTTGA | 55 |
| 172010 | GATTTGGTCTAGCTACAG | 56 |
| 172496 | TTCAACAGGGTACACAGAACATTT | 57 |
| 172537 | TGTGGATCACACCTGCCTTA | 58 |
| 172535 | TGGATCACACCTGCCTTAAA | 59 |
| 172010 | GATTTGGTCTAGCTACAG | 60 |
| 172536 | GTGGATCACACCTGCCTTAAA | 61 |
| 172598 | GATTGCGAAACAGCTTCTCTG | 62 |
| 172531 | TCACACCTGCCTTAAATTGC | 63 | c) Selected oligonucleotide primers for A1 for BRAF reverse (inverse) system (see Table 14)

TABLE 14

Primer A2 containing the mutation region:
CACTCCATCGAGATTTC (SEQ ID NO. 64)

Primer A1 (SEQ ID NOs. 65 to 81)
TCATGAAGACCTCACAGTAAAATA

TGTTTTCCTTTACTTACTACACCTCA

CTGTTTTCCTTTACTTACTACACCTCA

TGTTTTCCTTTACTTACTACACCTCAG

TTTTCCTTTACTTACTACACCTCAGA

GTTTTCCTTTACTTACTACACCTCAGA

TABLE 14-continued

TTATTGACTCTAAGAGGAAAGATGAA

GCCCCAAAAATCTTAAAAGCA

AAGCCCCAAAAATCTTAAAAGC

TTCAAGCCCCAAAAATCTTAAA

GCCCCAAAAATCTTAAAAGC

AGCCCCAAAAATCTTAAAAGC

ACACATTTCAAGCCCCAAAA

AACACATTTCAAGCCCCAAA

CACATTTCAAGCCCCAAAAA

TAACACATTTCAAGCCCCAAA

CACATTTCAAGCCCCAAAA

B): Example of DNA Region to be Targeted Upon Our Method when the Hot Spot Point Mutations of the 2nd and 3rd Codon of the Second Exon of the KRAS Gene is of Interest a) See FIGS. 24A-24E which shows the regions and the primers where molecular entities such as primers could target upon our multiplex method applied to this mutation. KRAS region 2th exon
Upon: KRAS (ENSG00000133703) from the Ensembl data bank
v-Ki-ras2 Kirsten rat sarcoma viral oncogene homolog [Source: HGNC Symbol; Acc: 6407
Point mutation; 6151
Design KRAS conventional and inverse: see FIGS. 24A-24E.

b) Selected DNA oligonucleotides for A1A2 primer pair for detecting KRAS exon 2 hot spot mutations upon conv configuration (see Table 15)

TABLE 15

Primer B1:
Mutation KrasG12V: TTGTGGTAGTTGGAGCTGT (SEQ ID NO. 244)

Mutation KrasG13D: GTAGTTGGAGCTGGTGA (245)

Mutation KrasG12D: TGTGGTAGTTGGAGCTGA (246)

Mutation KrasG12S: ACTTGTGGTAGTTGGAGCTA (247)

Mutation KrasG12A: TGTGGTAGTTGGAGCTGC (248)

Mutation KrasG12C: ACTTGTGGTAGTTGGAGCTT (249)

Primer B2: (SEQ ID NOs 83 to 120)
CTTAAGCGTCGATGGAGGAG

TGATTGAATTTTGTAAGGTATTTTGAA

CATGATTGAATTTTGTAAGGTATTTTG

TCATGATTGAATTTTGTAAGGTATTT

GATTGAATTTTGTAAGGTATTTTGAA

ACGTCTGCAGTCAACTGGAAT

TGCAGTCAACTGGAATTTTCAT

TCTGCAGTCAACTGGAATTTT

TABLE 15-continued

```
GTATCGTCAAGGCACTCTTGC
CGATACACGTCTGCAGTCAAC
ACGATACACGTCTGCAGTCAAC
TACGATACACGTCTGCAGTCAA
CTTAAGCGTCGATGGAGGAG
TAAGCGTCGATGGAGGAGTT
CGTCGATGGAGGAGTTTGTAA
AAGCGTCGATGGAGGAGTTT
TCTTAAGCGTCGATGGAGGA
TTTCTTAAGCGTCGATGGAG
TTTTTCTTAAGCGTCGATGG
TTTTTCTTAAGCGTCGATGG
GCATTTTCTTAAGCGTCGAT
TGTCTATGTAGCATTTATGCATTTTTC
TGTCTATGTAGCATTTATGCATTTT
CTGTCTATGTAGCATTTATGCATTTTT
TGTCTATGTAGCATTTATGCATTTT
CTGTCTATGTAGCATTTATGCATTTT
TCTGGCTATTTAGATAGAACAACTTGA
CTGGCTATTTAGATAGAACAACTTGA
GCAGAACAGCAGTCTGGCTA
CTTTAGCCGCCGCAGAAC
CAGAACAGCAGTCTGGCTATTTA
GAACAGCAGTCTGGCTATTTAGA
AGAACAGCAGTCTGGCTATTTAGA
TCCTTTGAGAGCCTTTAGCC
ATCCTTTGAGAGCCTTTAGC
TGATCCTTTGAGAGCCTTTAGC
GTATCGTCAAGGCACTCTTGC
ATGATCCTTTGAGAGCCTTTAGC
```

C) Selected DNA Oligonucleotides for A1A2 Primer Pair for Detecting KRAS Exon 2 Hot Spot Mutations Upon Inverse Configuration (See Table 16)

TABLE 16

```
Primer A2:
Sequence for A1for KRASinv:
A2: AAGGCACTCTTGCCTACGCCAC (SEQ ID NO. 250)

Or containing the mutation region:
Mutation KrasG12V: AAGGCACTCTTGCCTACGCCAT (251)

Mutation KrasG13D: AAGGCACTCTTGCCTACGCCAA (252)

Mutation KrasG12D: AAGGCACTCTTGCCTACGCCAA (253)

Mutation KrasG12S: AAGGCACTCTTGCCTACGCCAA (254)
```

TABLE 16-continued

```
Mutation KrasG12A: AAGGCACTCTTGCCTACGCCAC (255)

Mutation KrasG12C: AAGGCACTCTTGCCTACGCCAT (256)

A1: SEQ ID NOs 163 to 196 (Amo 2 to Amo35,
see FIG. 24D
```

REFERENCES

1. Metais, P., and Mandel, P. (1955). Bull Soc Chim Biol (Paris) 37, 999-1007.
2. Stroun, M., Anker, P., Lyautey, J., Lederrey, C., and Maurice, P. A. (1987) Isolation and characterization of DNA from the plasma of cancer patients. Eur J Cancer Clin Oncol 23, 707-12.
3. Anker, P., Mulcahy, H., Chen, X. Q., and Stroun, M. (1999) Detection of circulating tumour DNA in the blood (plasma/serum) of cancer patients. Cancer Metastasis Rev 18, 65-73.
4. Holdenrieder, S., Stieber, P., Chan, L. Y., Geiger, S., Kremer, A., Nagel, D., and Lo, Y. M. (2005) Cell-free DNA in serum and plasma: comparison of ELISA and quantitative PCR. Clin Chem 51, 1544-6.
5. Gormally, E., Hainaut, P., Caboux, E., Airoldi, L., Autrup, H., Malaveille, C., Dunning, A., Garte, S., Matullo, G., Overvad, K., Tjonneland, A., Clavel-Chapelon, F., Boffetta, P., Boeing, H., Trichopoulou, A., Palli, D., Krogh, V., Tumino, R., Panico, S., Bueno-de-Mesquita, H. B., Peeters, P. H., Lund, E., Gonzalez, C. A., Martinez, C., Dorronsoro, M., Barricarte, A., Tormo, M. J., Quiros, J. R., Berglund, G., Hallmans, G., Day, N. E., Key, T. J., Veglia, F., Peluso, M., Norat, T., Saracci, R., Kaaks, R., Riboli, E., and Vineis, P. (2004) Amount of DNA in plasma and cancer risk: a prospective study. Int J Cancer 111, 746-9.
6. Lievre, A., Bachet, J. B., Boige, V., Cayre, A., Le Corre, D., Buc, E., Ychou, M., Bouche, O., Landi, B., Louvet, C., Andre, T., Bibeau, F., Diebold, M. D., Rougier, P., Ducreux, M., Tomasic, G., Emile, J. F., Penault-Llorca, F., and Laurent-Puig, P. (2008) KRAS mutations as an independent prognostic factor in patients with advanced colorectal cancer treated with cetuximab. J Clin Oncol 26, 374-9.
7. Diehl, F., Li, M., Dressman, D., He, Y., Shen, D., Szabo, S., Diaz, L. A., Jr., Goodman, S. N., David, K. A., Juhl, H., Kinzler, K. W., and Vogelstein, B. (2005) Detection and quantification of mutations in the plasma of patients with colorectal tumors. Proc Natl Acad Sci USA 102, 16368-73.
8. Struchkov, V. A., Strazhevskaya, N. B., and Zhdanov, R. I. (2002) DNA-bound lipids of normal and tumor cells: retrospective and outlooks for functional genomics. Bioelectrochemistry 58, 23-30.
9. Wang, B. G., Huang, H. Y., Chen, Y. C., Bristow, R. E., Kassauei, K., Cheng, C. C., Roden, R., Sokoll, L. J., Chan, D. W., and Shih Ie, M. (2003) Increased plasma DNA integrity in cancer patients. Cancer Res 63, 3966-8.
10. Smith, G., Carey, F. A., Beattie, J., Wilkie, M. J., Lightfoot, T. J., Coxhead, J., Garner, R. C., Steele, R. J., and Wolf, C. R. (2002) Mutations in APC, Kirsten-ras, and p53—alternative genetic pathways to colorectal cancer. Proc Natl Acad Sci USA 99, 9433-8.
11. Einspahr, J. G., Martinez, M. E., Jiang, R., Hsu, C. H., Rashid, A., Bhattacharrya, A. K., Ahnen, D. J., Jacobs, E.

T., Houlihan, P. S., Webb, C. R., Alberts, D. S., and Hamilton, S. R. (2006) Associations of Ki-ras proto-oncogene mutation and p53 gene overexpression in sporadic colorectal adenomas with demographic and clinicopathologic characteristics. Cancer Epidemiol Biomarkers Prev 15, 1443-50.
12. Ferron, M., Praz, F., and Pocard, M. (2005). The genetics of colorectal cancer. Ann Chir 130, 602-7.
13. Wang, B. G., Huang, H. Y., Chen, Y. C., Bristow, R. E., Kassauei, K., Cheng, C. C., Roden, R., Sokoll, L. J., Chan, D. W., and Shih Ie, M. (2003) Increased plasma DNA integrity in cancer patients. Cancer Res 63, 3966-8.
14. Deligezer, U., Eralp, Y., Akisik, E. E., Akisik, E. Z., Saip, P., Topuz, E., and Dalay, N. (2008) Size distribution of circulating cell-free DNA in sera of breast cancer patients in the course of adjuvant chemotherapy. Clin Chem Lab Med 46, 311-7.
15. Umetani, N., Giuliano, A. E., Hiramatsu, S. H., Amersi, F., Nakagawa, T., Martino, S., and Hoon, D. S. (2006) Prediction of breast tumor progression by integrity of free circulating DNA in serum. J Clin Oncol 24, 4270-6
16. Chan, K. C., Zhang, J., Hui, A. B., Wong, N., Lau, T. K., Leung, T. N., Lo, K. W., Huang, D. W., and Lo, Y. M. (2004) Size distributions of maternal and fetal DNA in maternal plasma. Clin Chem 50, 88-92.
17. Ellinger, J., Wittkamp, V., Albers, P., Perabo, F. G., Mueller, S. C., von Ruecker, A., and Bastian, P. J. (2009) Cell-free circulating DNA: diagnostic value in patients with testicular germ cell cancer. J Urol 181, 363-71.
18. Mamon, H., Hader, C., Li, J., Wang, L., Kulke, M., Amicarelli, G., Shehi, E., Adlerstein, D., Roper, K., Killion, L., Hooshmand, S., and Makrigiorgos, G. M. (2008) Preferential amplification of apoptotic DNA from plasma: potential for enhancing detection of minor DNA alterations in circulating DNA. Clin Chem 54, 1582-4.
19. Schmidt, B., Weickmann, S., Witt, C., and Fleischhacker, M. (2008) Integrity of cell-free plasma DNA in patients with lung cancer and nonmalignant lung disease. Ann NY Acad Sci 1137, 207-13.
20. Liu, K. J., Brock, M. V., Shih Ie, M., and Wang, T. H. (2010) Decoding circulating nucleic acids in human serum using microfluidic single molecule spectroscopy. J Am Chem Soc 132, 5793-8.
21. Thierry, A. R., Mouliere, F., Gongora, C., Ollier, J., Robert, B., Ychou, M., Del Rio, M., and Molina, F. Origin and quantification of circulating DNA in mice with human colorectal cancer xenografts. Nucleic Acids Res. 2010 May 21. in press, available online.
22. Frattini et al. (2006), Annals of the New York Academy of Sciences Volume 1075, Circulating Nucleic Acids in Plasma and Serum IV pages 185-190.

The invention claimed is:

1. A method for the detection of a genetic polymorphism from a body fluid sample containing cell free nucleic acids of a subject susceptible to exhibit said genetic polymorphism on a specific gene, said body fluid sample being a plasma or serum or blood sample, said method comprising the steps of:

i) performing an amplification reaction by reacting a body fluid sample with forward primer A1, reverse primer A2, forward primer B1, reverse primer B2, and SYBR Green under conditions allowing for the amplification of target nucleic acids in the body fluid sample to produce amplicons A1A2, B1B2, and A1B2, wherein: the genetic polymorphism complementary nucleotide(s) appears at the 3' end of B1 or at the 3' end of A2, A1A2 and B1B2 are between 50 to 100 bp in length and differ from each other in length by at most 20%, and A1B2 is between 200 bp and 450 bp in length;

ii) detecting the presence of and determining the concentration of amplicons A1A2 ($C_{A1A2}$) and B1B2 ($C_{B1B2}$) based on a signal generated from the SYBR Green;

iii) calculating the ratio $C_{B1B2}/C_{A1A2}$ if the genetic polymorphism complementary nucleotide(s) appears at the 3' end of B1, or calculating the ratio $C_{A1A2}/C_{B1B2}$ if the genetic polymorphism complementary nucleotide(s) appears at the 3' end of A2; and iv) detecting the presence of the genetic polymorphism based on a determination that the ratio $C_{B1B2}/C_{A1A2}$ or $C_{A1A2}/C_{B1B2}$ is higher than a predetermined threshold.

2. A method according to claim 1 wherein said method further comprises the following steps:

determining the concentration of A1B2 ($C_{A1B2}$); and calculating the ratio $C_{A1A2}/C_{A1B2}$ or $C_{A1B2}/C_{A1A2}$ if the genetic polymorphism complementary nucleotide(s) appears at the 3' end of B1, or calculating the ratio $C_{B1B2}/C_{A1B2}$ or $C_{A1B2}/C_{B1B2}$, if the genetic polymorphism complementary nucleotide(s) appears at the 3' end of A2, wherein said concentration and ratio are indicative of the integrity of circulating nucleic acids in said sample.

3. A method according to claim 1, wherein A1A2 and B1B2 are greater than 50 bp and less than 80 bp in length, and wherein A1B2 is greater than 250 bp and less than 350 bp in length.

* * * * *

SEQUENCE LISTING

```
<160> NUMBER OF SEQ ID NOS: 278

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras rev primer

<400> SEQUENCE: 1
ggtccttttc cgtgtgtagg                                                   20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 409 primer

<400> SEQUENCE: 2
gcctcccttt ccagcact                                                     18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 357 primer

<400> SEQUENCE: 3
ggcatctcta ggacgaaggt                                                   20
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 300 primer

<400> SEQUENCE: 4
ggtccttttc cgtgtgtagg                                            20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 249 primer

<400> SEQUENCE: 5
tggaagagca taggaaagtg c                                          21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 185 primer

<400> SEQUENCE: 6
atctgcctcc gagttcctg                                             19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 101 primer

<400> SEQUENCE: 7
ccctacacgt agagcctgtg a                                          21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 73 primer

<400> SEQUENCE: 8
gcctgtgacc tacagtgaaa a                                          21

<210> SEQ ID NO 9
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras B1 conv G12V primer

<400> SEQUENCE: 9
acttgtggta gttggagctg t                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras B2 conv primer

<400> SEQUENCE: 10
gaatggtcct gcaccagtaa                                                20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras conv B1 primer

<400> SEQUENCE: 11
acttgtggta gttggagctg g                                              21

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Conv B2 primer

<400> SEQUENCE: 12
gattctgaat tagctgtatc gtcaagg                                        27

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Conv A1 primer

<400> SEQUENCE: 13
taagcgtcga tggaggagtt                                                20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      primer
<220> FEATURE:
<223> OTHER INFORMATION: Kras Conv A2 primer

<400> SEQUENCE: 14
ccagttgact gcagacgtgt a                                              21

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv MutG12V primer

<400> SEQUENCE: 15
aactcttgcc tacgccac                                                  18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf conv A1 primer

<400> SEQUENCE: 16
ggagagcagg ataccacagc                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf conv A2 primer

<400> SEQUENCE: 17
agcaagcaat caaaaactcc                                                20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf inv A1 primer

<400> SEQUENCE: 18
tcatgaagac ctcacagtaa aaa                                            23

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf inv A2 V600E primer
```

<400> SEQUENCE: 19
cactccatcg agatttct                                                      18

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf inv B1 primer

<400> SEQUENCE: 20
ctagaaagtc attgaaggtc tcaac                                              25

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf inv B2 primer

<400> SEQUENCE: 21
tgatttttgt gaatactggg aac                                                23

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf inv B1 V600E primer

<400> SEQUENCE: 22
ccatcgagat ttcactgtag ct                                                 22

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf conv A1v1 primer

<400> SEQUENCE: 23
ttattgactc taagaggaaa gatgaa                                             26

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf conv A2v2 primer

<400> SEQUENCE: 24
gagcaagcat tatgaagagt ttagg                                              25

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Braf conv B2 primer

<400> SEQUENCE: 25
tagcctcaat tcttaccatc caca                                              24

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Braf conv B1 V600E primer

<400> SEQUENCE: 26
gattttggtc tagctacaga                                                   20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Braf conv V600E primer

<400> SEQUENCE: 27
gctacagtga aatctcgatg g                                                 21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Kras Inv A1 6126 primer

<400> SEQUENCE: 28
gcctgctgaa aatgactga                                                    19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Kras Inv B1 6379 primer

<400> SEQUENCE: 29
ccttgggttt caagttatat g                                                 21

<210> SEQ ID NO 30
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv B2 6445 primer

<400> SEQUENCE: 30
ccctgacata ctcccaagga                                                    20

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 MutG12V primer

<400> SEQUENCE: 31
ctcttgccta cgccaa                                                        16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 MutG13D64 primer

<400> SEQUENCE: 32
gcactcttgc ctacgt                                                        16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 G12D low primer

<400> SEQUENCE: 33
ctcttgccta cgccat                                                        16

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 G12A low primer

<400> SEQUENCE: 34
ctcttgccta cgccag                                                        16

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<223> OTHER INFORMATION: Kras Inv A2 G12S low primer

<400> SEQUENCE: 35
tcttgcctac gccact                                                  16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 G12C low primer

<400> SEQUENCE: 36
tcttgcctac gccaca                                                  16

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kras Inv mut Blocker

<400> SEQUENCE: 37
gcctacgcca ccagctc                                                 17

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonlucleotides for B2 primers for
      BRAF conv: B1 primer containing the mutation region

<400> SEQUENCE: 38
gattttggtc tagctacag                                               19

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Selected oligonucleotides for B2 primers for
      BRAF conv

<400> SEQUENCE: 39
atccacaaaa tggatccaga ca                                           22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
```

-continued

BRAF conv

<400> SEQUENCE: 40
attcttacca tccacaaaat gg								22

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 41
agcctcaatt cttaccatcc a								21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 42
gcctcaattc ttaccatcca								20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 43
gcctcaattc ttaccatcca								20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 44
gcctcaattc ttaccatcca c								21

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<223> OTHER INFORMATION: Selected oligonucleotides for B2 primers for
      BRAF conv

<400> SEQUENCE: 45
agcctcaatt cttaccatcc ac                                            22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 46
cctcaattct taccatccac aa                                            22

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 47
tcagtggaaa aatagcctca a                                             21

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 48
cagtggaaaa atagcctcaa ttc                                           23

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 49
cagtggaaaa atagcctcaa ttct                                          24

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<223> OTHER INFORMATION: Selected oligonucleotides for B2 primers for
      BRAF conv

<400> SEQUENCE: 50
atcagtggaa aaatagcctc aa                                              22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 51
tcagtggaaa aatagcctca at                                              22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 52
tttcaacagg gtacacagaa ca                                              22

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 53
cagggtacac agaacatttt gaa                                             23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 54
gggtacacag aacattttga aca                                             23

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
          primer
<220> FEATURE:
<223> OTHER INFORMATION: Selected oligonucleotides for B2 primers for
      BRAF conv

<400> SEQUENCE: 55
aacagggtac acagaacatt ttga                                          24

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 56
gattttggtc tagctacag                                                19

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 57
ttcaacaggg tacacagaac attt                                          24

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 58
tgtggatcac acctgcctta                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 59
tggatcacac ctgccttaaa                                               20

<210> SEQ ID NO 60
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 60
gattttggtc tagctacag                                              19

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 61
gtggatcaca cctgccttaa a                                           21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 62
gattgcgaaa cagcttctct g                                           21

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotides for B2 primers for
      BRAF conv

<400> SEQUENCE: 63
tcacacctgc cttaaattgc                                             20

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev: A2 primer containing the mutation region

<400> SEQUENCE: 64
cactccatcg agatttc                                                17

<210> SEQ ID NO 65
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 65
tcatgaagac ctcacagtaa aaata                                          25

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 66
tgttttcctt tacttactac acctca                                         26

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 67
ctgttttcct ttacttacta cacctca                                        27

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 68
tgttttcctt tacttactac acctcag                                        27

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 69
ttttccttta cttactacac ctcaga                                         26

<210> SEQ ID NO 70
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 70
gttttccttt acttactaca cctcaga                                           27

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 71
ttattgactc taagaggaaa gatgaa                                            26

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 72
gccccaaaaa tcttaaaagc a                                                 21

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 73
aagccccaaa aatcttaaaa gc                                                22

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 74
ttcaagcccc aaaaatctta aa                                                22

<210> SEQ ID NO 75
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 75
gccccaaaaa tcttaaaagc                                                    20

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 76
agccccaaaa atcttaaaag c                                                  21

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 77
acacatttca agccccaaaa                                                    20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 78
aacacatttc aagccccaaa                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 79
cacatttcaa gccccaaaaa                                                    20

<210> SEQ ID NO 80
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 80
taacacattt caagccccaa a                                              21

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected oligonucleotide primers for A1 for
      BRAF rev

<400> SEQUENCE: 81
cacatttcaa gccccaaaa                                                 19

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Selected DNA oligonucleotides for A1A2 primer
      pair for detecting KRAS exon 2 hot spot mutations upon conv
      configuration : B1 primer

<400> SEQUENCE: 82
gtatcgtcaa ggcactcttg c                                              21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 83
cttaagcgtc gatggaggag                                                20

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 84
```
tgattgaatt ttgtaaggta ttttgaa                                              27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 85
catgattgaa ttttgtaagg tattttg                                              27

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 86
tcatgattga attttgtaag gtattt                                               26

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 87
gattgaattt tgtaaggtat tttgaa                                               26

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 88
acgtctgcag tcaactggaa t                                                    21

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<223> OTHER INFORMATION: Selected DNA oligonucleotides for A1A2 primer
      pair for detecting KRAS exon 2 hot spot mutations upon conv
      configuration

<400> SEQUENCE: 89
tgcagtcaac tggaattttc at                                              22

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 90
tctgcagtca actggaattt t                                               21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 91
gtatcgtcaa ggcactcttg c                                               21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 92
cgatacacgt ctgcagtcaa c                                               21

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 93
acgatacacg tctgcagtca ac                                              22

<210> SEQ ID NO 94
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 94
tacgatacac gtctgcagtc aa                                              22

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 95
cttaagcgtc gatggaggag                                                 20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 96
taagcgtcga tggaggagtt                                                 20

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 97
cgtcgatgga ggagtttgta a                                               21

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 98
```
aagcgtcgat ggaggagttt                                           20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 99
tcttaagcgt cgatggagga                                           20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 100
tttcttaagc gtcgatggag                                           20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 101 ttttcttaa gcgtcgatgg                                            20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 102 ttttcttaa gcgtcgatgg                                            20

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 103
gcatttttct taagcgtcga t                                              21

<210> SEQ ID NO 104
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 104
tgtctatgta gcatttatgc attttc                                         27

<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 105
tgtctatgta gcatttatgc atttt                                          26

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 106
ctgtctatgt agcatttatg cattttt                                        27

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 107
tgtctatgta gcatttatgc atttt                                          25

<210> SEQ ID NO 108
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 108
ctgtctatgt agcatttatg cattt                                            26

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 109
tctggctatt tagatagaac aacttga                                          27

<210> SEQ ID NO 110
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 110
ctggctattt agatagaaca acttga                                           26

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 111
gcagaacagc agtctggcta                                                  20

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration
```

```
<400> SEQUENCE: 112
ctttagccgc cgcagaac                                                 18

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 113
cagaacagca gtctggctat tta                                           23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 114
gaacagcagt ctggctattt aga                                           23

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 115
agaacagcag tctggctatt taga                                          24

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 116
tcctttgaga gcctttagcc                                               20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 117
atcctttgag agcctttagc                                                  20

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 118
tgatcctttg agagccttta gc                                               22

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 119
gtatcgtcaa ggcactcttg c                                                21

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Selected DNA oligonucleotides for A1A2 primer
      pair for detecting KRAS exon 2 hot spot mutations upon conv
      configuration

<400> SEQUENCE: 120
atgatccttt gagagccttt agc                                              23

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Selected DNA region target for B2 primer for
      detecting KRAS exon 2 hot spot mutations upon conv configuration:
      B1 primer

<400> SEQUENCE: 121
acttgtggta gttggagctg g                                                21

```
<210> SEQ ID NO 122
<211> LENGTH: 300
<212> TYPE: DNA
<213> ORGANISM: Homo sapiens
<220> FEATURE:
<223> OTHER INFORMATION: Kras Exon 2

<400> SEQUENCE: 122
tagtgtatta accttatgtg tgacatgttc taatatagtc acattttcat tatttttatt      60
ataaggcctg ctgaaaatga ctgaatataa acttgtggta gttggagctg gtggcgtagg     120
caagagtgcc ttgacgatac agctaattca gaatcatttt gtggacgaat atgatccaac     180
aatagaggta atcttgtttt taatatgcat attactggtg caggaccatt ctttgataca     240
gataaaggtt tctctgacca ttttcatgag tacttattac aagataatta tgctgaaagt     300

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo53

<400> SEQUENCE: 123
gcaagagtgc cttgacgata c                                                21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo54

<400> SEQUENCE: 124
agagtgcctt gacgatacag c                                                21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo55

<400> SEQUENCE: 125
gagtgccttg acgatacagc t                                                21

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo56

<400> SEQUENCE: 126
gagtgccttg acgatacagc                                                  20
```

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Amo57

<400> SEQUENCE: 127
agagtgcctt gacgatacag ct                                                22

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Amo58

<400> SEQUENCE: 128
ccttgacgat acagctaatt caga                                              24

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Amo59

<400> SEQUENCE: 129
ccttgacgat acagctaatt cag                                               23

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Amo60

<400> SEQUENCE: 130
ccttgacgat acagctaatt ca                                                22

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Amo61

<400> SEQUENCE: 131
tgacgataca gctaattcag aatca                                             25

<210> SEQ ID NO 132
<211> LENGTH: 25
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo62

<400> SEQUENCE: 132
ccttgacgat acagctaatt cagaa                                               25

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo63

<400> SEQUENCE: 133
gctaattcag aatcattttg tgga                                                24

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo64

<400> SEQUENCE: 134
gctaattcag aatcattttg tgg                                                 23

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo65

<400> SEQUENCE: 135
gctaattcag aatcattttg tggac                                               25

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo66

<400> SEQUENCE: 136
cagctaattc agaatcattt tgtg                                                24

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Amo67

<400> SEQUENCE: 137
cagctaattc agaatcattt tgtgg                                          25

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo73

<400> SEQUENCE: 138
gaatcatttt gtggacgaat atga                                           24

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo74

<400> SEQUENCE: 139
gaatcatttt gtggacgaat atg                                            23

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo68

<400> SEQUENCE: 140
ttgtggacga atatgatcca a                                              21

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo69

<400> SEQUENCE: 141
ttttgtggac gaatatgatc ca                                             22

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo70

<400> SEQUENCE: 142
```
ttgtggacga atatgatcca ac                                          22

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo71

<400> SEQUENCE: 143
tgtggacgaa tatgatccaa                                             20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo72

<400> SEQUENCE: 144
ttgtggacga atatgatcca                                             20

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo75

<400> SEQUENCE: 145
gtggacgaat atgatccaac aa                                          22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo76

<400> SEQUENCE: 146
ttgtggacga atatgatcca ac                                          22

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo77

<400> SEQUENCE: 147
tgtggacgaa tatgatccaa c                                           21

```
<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo78

<400> SEQUENCE: 148
gtggacgaat atgatccaac a                                              21

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo79

<400> SEQUENCE: 149
gtggacgaat atgatccaac aat                                            23

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo80

<400> SEQUENCE: 150
gacgaatatg atccaacaat agagg                                          25

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo81

<400> SEQUENCE: 151
cgaatatgat ccaacaatag agg                                            23

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo82

<400> SEQUENCE: 152
acgaatatga tccaacaata gagg                                           24

<210> SEQ ID NO 153
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Amo83

<400> SEQUENCE: 153
cgaatatgat ccaacaatag aggt                                            24

<210> SEQ ID NO 154
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo84

<400> SEQUENCE: 154
acgaatatga tccaacaata gaggt                                           25

<210> SEQ ID NO 155
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo85

<400> SEQUENCE: 155
tgatccaaca atagaggtaa atcttg                                          26

<210> SEQ ID NO 156
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo86

<400> SEQUENCE: 156
cgaatatgat ccaacaatag aggtaa                                          26

<210> SEQ ID NO 157
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo87

<400> SEQUENCE: 157
cgaatatgat ccaacaatag aggta                                           25

<210> SEQ ID NO 158
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Amo88

<400> SEQUENCE: 158
acgaatatga tccaacaata gaggta                                              26

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo89

<400> SEQUENCE: 159
atgatccaac aatagaggta aatcttg                                             27

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Selected DNA region target for A1 primer for
      detecting KRAS exon 2 hot spot mutations upon rev configuration:
      A2 primer

<400> SEQUENCE: 160
gtggcgtagg caagagtgcc tt                                                  22

<210> SEQ ID NO 161
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: KRAS exon 2

<400> SEQUENCE: 161
ttgaaataat ttttcatata aaggtgagtt tgtattaaaa ggtactggtg gagtatttga         60
tagtgtatta accttatgtg tgacatgttc taatatagtc acattttcat tattttatt         120 ataaggcctg ctgaaaatga ctgaatataa acttgtggta gttggagctg gtggcgtagg        180
caagagtgcc ttgacgatac agctaattca gaatcatttt gtggacgaat atgatccaac        240
aatagaggta aatcttgttt taatatgcat attactggtg caggaccatt ctttgataca        300
gataaaggtt tctctgacca ttttcatgag tacttattac aagataatta tgctgaaagt       360

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo1

<400> SEQUENCE: 162
aggcctgctg aaaatgactg                                                     20

```
<210> SEQ ID NO 163
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo10

<400> SEQUENCE: 163
tgaatataaa cttgtggtag ttgga                                             25

<210> SEQ ID NO 164
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo11

<400> SEQUENCE: 164
ctgaatataa acttgtggta gttgga                                            26

<210> SEQ ID NO 165
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo12

<400> SEQUENCE: 165
tgaatataaa cttgtggtag ttggag                                            26

<210> SEQ ID NO 166
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo13

<400> SEQUENCE: 166
ctgaatataa acttgtggta gttggag                                           27

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo14

<400> SEQUENCE: 167
actgaatata aacttgtggt agttgga                                           27

<210> SEQ ID NO 168
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Amo15

<400> SEQUENCE: 168
gaaaatgact gaatataaac ttgtgg                                          26

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo16

<400> SEQUENCE: 169
gaaaatgact gaatataaac ttgtggt                                         27

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo17

<400> SEQUENCE: 170
tgactgaata taaacttgtg g                                               21

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo18

<400> SEQUENCE: 171
aaaatgactg aatataaact tgtgg                                           25

<210> SEQ ID NO 172
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo19

<400> SEQUENCE: 172
aaaatgactg aatataaact tgtggt                                          26

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Amo20

<400> SEQUENCE: 173
tgaaaatgac tgaatataaa cttgtgg                                              27

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo21

<400> SEQUENCE: 174
ctgctgaaaa tgactgaata taaa                                                 24

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo22

<400> SEQUENCE: 175
tgctgaaaat gactgaatat aaa                                                  23

<210> SEQ ID NO 176
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo23

<400> SEQUENCE: 176
gaaaatgact gaatataaac ttgtgg                                               26

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo24

<400> SEQUENCE: 177
ctgctgaaaa tgactgaata taaac                                                25

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo2

<400> SEQUENCE: 178
gcctgctgaa aatgactgaa                                                  20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo3

<400> SEQUENCE: 179
aaggcctgct gaaaatgact                                                  20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo4

<400> SEQUENCE: 180
ggcctgctga aaatgactga                                                  20

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo5

<400> SEQUENCE: 181
ggcctgctga aaatgactg                                                   19

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo6

<400> SEQUENCE: 182
taaggcctgc tgaaaatgac t                                                21

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo7

<400> SEQUENCE: 183
taaggcctgc tgaaaatgac                                                  20

<210> SEQ ID NO 184

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo8

<400> SEQUENCE: 184
ataaggcctg ctgaaaatga                                                     20

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo9

<400> SEQUENCE: 185
ataaggcctg ctgaaaatga c                                                   21

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo25

<400> SEQUENCE: 186
attataaggc ctgctgaaaa tga                                                 23

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo26

<400> SEQUENCE: 187
attataaggc ctgctgaaaa tgac                                                24

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo27

<400> SEQUENCE: 188
attataaggc ctgctgaaaa tg                                                  22

<210> SEQ ID NO 189
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Amo28

<400> SEQUENCE: 189
tattataagg cctgctgaaa atga                                           24

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo29

<400> SEQUENCE: 190
attataaggc ctgctgaaaa                                                20

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo30

<400> SEQUENCE: 191
tttttattat aaggcctgct g                                              21

<210> SEQ ID NO 192
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo31

<400> SEQUENCE: 192
cattattttt attataaggc ctgctg                                         26

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo32

<400> SEQUENCE: 193 attttttatta taaggcctgc tg                                            22

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo33
```

<400> SEQUENCE: 194
ttatttttat tataaggcct gctg                                          24

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo34

<400> SEQUENCE: 195
tatttttatt ataaggcctg ctg                                           23

<210> SEQ ID NO 196
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo35

<400> SEQUENCE: 196
tcattatttt tattataagg cctgctg                                       27

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Selected DNA region target for B1B2 primer pair
      design for detecting exon 2 KRAS hot spot mutations upon the rev
      configuration of our method : A1 primer

<400> SEQUENCE: 197
gcctgctgaa aatgactga                                                19

<210> SEQ ID NO 198
<211> LENGTH: 780
<212> TYPE: DNA
<213> ORGANISM: Homo sapiens
<220> FEATURE:
<223> OTHER INFORMATION: Kras exon 2

<400> SEQUENCE: 198
tagtgtatta accttatgtg tgacatgttc taatatagtc acattttcat tatttttatt      60
ataaggcctg ctgaaaatga ctgaatataa acttgtggta gttggagctg gtggcgtagg     120
caagagtgcc ttgacgatac agctaattca gaatcatttt gtggacgaat atgatccaac     180
aatagaggta atcttgtttt aatatgcat attactggtg caggaccatt ctttgataca      240
gataaaggtt tctctgacca ttttcatgag tacttattac aagataatta tgctgaaagt     300
taagttatct gaaatgtacc ttgggtttca agttatatgt aaccattaat atgggaactt     360
tactttcctt gggagtatgt cagggtccat gatgttcact ctctgtgcat tttgattgga     420
agtgtatttc agagtttcgt gagagggtag aaatttgtat cctatctgga cctaaaagac     480
aatcttttta ttgtaacttt tattttatg ggtttcttgg tattgtgaca tcatatgtaa     540

```
aggttagatt taattgtact agtgaaatat aattgtttga tggttgattt ttttaaactt    600
catcagcagt attttcctat cttcttctca acattagaga acctacaact accggataaa    660
ttttacaaaa tgaattattt gcctaaggtg tggtttatat aaaggtacta ttaccaactt    720
tacctttgct ttgttgtcat ttttaaattt actcaaggaa atactaggat ttaaaaaaaa    780
```

<210> SEQ ID NO 199  
<211> LENGTH: 22  
<212> TYPE: DNA  
<213> ORGANISM: Artificial Sequence  
<220> FEATURE:  
<223> OTHER INFORMATION: Description of Artificial Sequence: Synthetic oligonucleotide  
<220> FEATURE:  
<223> OTHER INFORMATION: Amo42

<400> SEQUENCE: 199

```
tgaaatgtac cttgggtttc aa                                              22
```

<210> SEQ ID NO 200  
<211> LENGTH: 21  
<212> TYPE: DNA  
<213> ORGANISM: Artificial Sequence  
<220> FEATURE:  
<223> OTHER INFORMATION: Description of Artificial Sequence: Synthetic oligonucleotide  
<220> FEATURE:  
<223> OTHER INFORMATION: Amo43

<400> SEQUENCE: 200

```
tgaaatgtac cttgggtttc a                                               21
```

<210> SEQ ID NO 201  
<211> LENGTH: 23  
<212> TYPE: DNA  
<213> ORGANISM: Artificial Sequence  
<220> FEATURE:  
<223> OTHER INFORMATION: Description of Artificial Sequence: Synthetic oligonucleotide  
<220> FEATURE:  
<223> OTHER INFORMATION: Amo44

<400> SEQUENCE: 201

```
tgaaatgtac cttgggtttc aag                                             23
```

<210> SEQ ID NO 202  
<211> LENGTH: 24  
<212> TYPE: DNA  
<213> ORGANISM: Artificial Sequence  
<220> FEATURE:  
<223> OTHER INFORMATION: Description of Artificial Sequence: Synthetic oligonucleotide  
<220> FEATURE:  
<223> OTHER INFORMATION: Amo45

<400> SEQUENCE: 202

```
gaaatgtacc ttgggtttca agtt                                            24
```

<210> SEQ ID NO 203  
<211> LENGTH: 22  
<212> TYPE: DNA  
<213> ORGANISM: Artificial Sequence  
<220> FEATURE:  
<223> OTHER INFORMATION: Description of Artificial Sequence: Synthetic oligonucleotide  
<220> FEATURE:  
<223> OTHER INFORMATION: Amo46

<400> SEQUENCE: 203
gaaatgtacc ttgggtttca ag                                              22

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo37

<400> SEQUENCE: 204
tccttgggag tatgtcaggg                                                 20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo38

<400> SEQUENCE: 205
tgtcagggtc catgatgttc                                                 20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo39

<400> SEQUENCE: 206
ccttgggagt atgtcagggt                                                 20

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo40

<400> SEQUENCE: 207
ggagtatgtc agggtccatg a                                               21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo41

<400> SEQUENCE: 208
tgtgcatttt gattggaagt g                                               21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo47

<400> SEQUENCE: 209
cttgggagta tgtcagggtc c                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo48

<400> SEQUENCE: 210
tccttgggag tatgtcaggg t                                              21

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo49

<400> SEQUENCE: 211
tgtcagggtc catgatgttc                                                20

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo51

<400> SEQUENCE: 212
tctctgtgca ttttgattgg a                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo50

<400> SEQUENCE: 213
tttcagagtt tcgtgagagg g                                              21

<210> SEQ ID NO 214
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo52

<400> SEQUENCE: 214
ttcagagttt cgtgagaggg                                                 20

<210> SEQ ID NO 215
<211> LENGTH: 1320
<212> TYPE: DNA
<213> ORGANISM: Homo sapiens

<400> SEQUENCE: 215
ttatttcccc atgacacaat ccagctttat ttgacactca ttctctcaac tctcatctga     60
ttcttactgt taatatttat ccaagagaac tactgccatg atgctttaaa agttttttctg   120 tagctgttgc atattgactt ctaacactta gaggtggggg tccactagga aaactgtaac    180
aataagagtg gagatagctg tcagcaactt ttgtgagggt gtgctacagg gtgtagagca    240
ctgtgaagtc tctacatgag tgaagtcatg atatgatcct ttgagagcct ttagccgccg    300
cagaacagca gtctggctat ttagatagaa caacttgatt ttaagataaa gaactgtct     360 atgtagcatt tatgcatttt tcttaagcgt cgatggagga gtttgtaaat gaagtacagt    420
tcattacgat acacgtctgc agtcaactgg aattttcatg attgaatttt gtaaggtatt    480
ttgaaataat ttttcatata aaggtgagtt tgtattaaaa ggtactggtg gagtatttga    540
tagtgtatta accttatgtg tgacatgttc taatatagtc acattttcat tatttttatt    600
ataaggcctg ctgaaaatga ctgaatataa acttgtggta gttggagctg gtggcgtagg    660
caagagtgcc ttgacgatac agctaattca gaatcatttt gtggacgaat atgatccaac    720
aatagaggta aatcttgttt taatatgcat attactggtg caggaccatt ctttgataca    780
gataaaggtt tctctgacca ttttcatgag tacttattac aagataatta tgctgaaagt    840
taagttatct gaaatgtacc ttgggtttca agttatatgt aaccattaat atgggaactt    900
tactttcctt gggagtatgt cagggtccat gatgttcact ctctgtgcat tttgattgga    960
agtgtatttc agagtttcgt gagagggtag aaatttgtat cctatctgga cctaaaagac   1020 aatctttta ttgtaacttt tattttatg ggtttcttgg tattgtgaca tcatatgtaa     1080
aggttagatt taattgtact agtgaaatat aattgtttga tggttgattt ttttaaactt   1140
catcagcagt attttcctat cttcttctca acattagaga acctacaact accggataaa   1200
ttttacaaaa tgaattattt gcctaaggtg tggtttatat aaaggtacta ttaccaactt   1260
tacctttgct ttgttgtcat ttttaaattt actcaaggaa atactaggat taaaaaaaa   1320

<210> SEQ ID NO 216
<211> LENGTH: 81
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Reverse primer for mutated amplicon

<400> SEQUENCE: 216
tggtagttgg agctggtggc gtaggcaaga gtgccttgac gatacagcta attcagaatc    60
```
attttgtgga cgaatatgat c 81

<210> SEQ ID NO 217
<211> LENGTH: 331
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Primer pair for non mutated amplicon

<400> SEQUENCE: 217
tcagcaactt ttgtgagggt gtgctacagg gtgtagagca ctgtgaagtc tctacatgag    60
tgaagtcatg atatgatcct ttgagagcct ttagccgccg cagaacagca gtctggctat   120
ttagatagaa caacttgatt ttaagataaa agaactgtct atgtagcatt tatgcatttt   180
tcttaagcgt cgatggagga gtttgtaaat gaagtacagt tcattacgat acacgtctgc   240
agtcaactgg aattttcatg attgaatttt gtaaggtatt tgaaataat ttttcatata    300 aaggtgagtt tgtattaaaa ggtactggtg g                                  331

<210> SEQ ID NO 218
<211> LENGTH: 75
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Reverse primer for mutated amplicon

<400> SEQUENCE: 218
tattaacctt atgtgtgaca tgttctaata tagtcacatt ttcattattt ttattataag    60
gcctgctgaa aatga                                                    75

<210> SEQ ID NO 219
<211> LENGTH: 332
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Primer pair for non mutated amplicon

<400> SEQUENCE: 219
aatcttgttt taatatgcat attactggtg caggaccatt ctttgataca gataaaggtt    60
tctctgacca ttttcatgag tacttattac aagataatta tgctgaaagt taagttatct   120
gaaatgtacc ttgggtttca agttatatgt aaccattaat atgggaactt tactttcctt   180
gggagtatgt cagggtccat gatgttcact ctctgtgcat tttgattgga agtgtatttc   240
agagtttcgt gagagggtag aaatttgtat cctatctgga cctaaaagac aatcttttta   300
ttgtaacttt tatttttatg ggtttcttgg ta                                 332

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
     primer
<220> FEATURE:
<223> OTHER INFORMATION: Kras 60 Hf primer

```
<400> SEQUENCE: 220
gcctgtgacc tacagtgaaa a                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 73 Hf primer

<400> SEQUENCE: 221
ccctacacgt agagcctgtg a                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 101 Hf primer

<400> SEQUENCE: 222
gagatggtgg aagaacaggt g                                              21

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 145 Hf primer

<400> SEQUENCE: 223
tgggctgtga cattgctg                                                  18

<210> SEQ ID NO 224
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 185 Hf primer

<400> SEQUENCE: 224
atctgcctcc gagttcctg                                                 19

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 249 Hf primer

<400> SEQUENCE: 225
tggaagagca taggaaagtg c                                              21
```

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 300 Hf primer

<400> SEQUENCE: 226
ggtccttttc cgtgtgtagg                                          20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 357 Hf

<400> SEQUENCE: 227
ggcatctcta ggacgaaggt                                          20

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 409 Hf

<400> SEQUENCE: 228
gcctcccttt ccagcact                                            18

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 145-300r primer

<400> SEQUENCE: 229
tgaccaagca aaacagacca                                          20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 46 Hr primer

<400> SEQUENCE: 230
gctgtatcgt caaggcactc                                          20

<210> SEQ ID NO 231
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 82 Hr primer

<400> SEQUENCE: 231
ttggatcata ttcgtccaca a                                              21

<210> SEQ ID NO 232
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 138 Hr primer

<400> SEQUENCE: 232
caaagaatgg tcctgcacc                                                 19

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 200 Hr primer

<400> SEQUENCE: 233
tgaaaatggt cagagaaacc tt                                             22

<210> SEQ ID NO 234
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 250 Hr primer

<400> SEQUENCE: 234
tgaaacccaa ggtacatttc ag                                             22

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 300 Hr primer

<400> SEQUENCE: 235
gaacatcatg gaccctgaca                                                20

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                                   primer
<220> FEATURE:
<223> OTHER INFORMATION: Kras 350 Hr primer

<400> SEQUENCE: 236
ttctaccctc tcacgaaact ctg                                            23

<210> SEQ ID NO 237
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras 400 Hr primer

<400> SEQUENCE: 237
aaagattgtc ttttaggtcc agatagg                                        27

<210> SEQ ID NO 238
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Non-Mutated Hf primer

<400> SEQUENCE: 238
gtagttggag ctggtggc                                                  18

<210> SEQ ID NO 239
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras G13D Hf primer

<400> SEQUENCE: 239
gtagttggag ctggtga                                                   17

<210> SEQ ID NO 240
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras G12V Hf primer

<400> SEQUENCE: 240
ttgtggtagt tggagctgt                                                 19

<210> SEQ ID NO 241
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras G12D Hf primer
```

```
<400> SEQUENCE: 241
tgtggtagtt ggagctga                                                 18

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras G12S Hf primer

<400> SEQUENCE: 242
acttgtggta gttggagcta                                               20

<210> SEQ ID NO 243
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras G12A Hf primer

<400> SEQUENCE: 243
tgtggtagtt ggagctgc                                                 18

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer for mutation KrasG12V

<400> SEQUENCE: 244
ttgtggtagt tggagctgt                                                19

<210> SEQ ID NO 245
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer for mutation KrasG13D

<400> SEQUENCE: 245
gtagttggag ctggtga                                                  17

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer for mutation KrasG12D

<400> SEQUENCE: 246
tgtggtagtt ggagctga                                                 18
```

```
<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer for mutation KrasG12S

<400> SEQUENCE: 247
acttgtggta gttggagcta                                                   20

<210> SEQ ID NO 248
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer for mutation KrasG12A

<400> SEQUENCE: 248
tgtggtagtt ggagctgc                                                     18

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer for mutation KrasG12C

<400> SEQUENCE: 249
acttgtggta gttggagctt                                                   20

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer A2

<400> SEQUENCE: 250
aaggcactct tgcctacgcc ac                                                22

<210> SEQ ID NO 251
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Primer for mutation KrasG12V

<400> SEQUENCE: 251
aaggcactct tgcctacgcc at                                                22

<210> SEQ ID NO 252
<211> LENGTH: 22
<212> TYPE: DNA
```

<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Primer for mutation KrasG13D

<400> SEQUENCE: 252
aaggcactct tgcctacgcc aa                                                22

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Primer for mutation KrasG12D

<400> SEQUENCE: 253
aaggcactct tgcctacgcc aa                                                22

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Primer for mutation KrasG12S

<400> SEQUENCE: 254
aaggcactct tgcctacgcc aa                                                22

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Primer for mutation KrasG12A

<400> SEQUENCE: 255
aaggcactct tgcctacgcc ac                                                22

<210> SEQ ID NO 256
<211> LENGTH: 22
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Primer for mutation KrasG12C

<400> SEQUENCE: 256
aaggcactct tgcctacgcc at                                                22

<210> SEQ ID NO 257
<211> LENGTH: 18
<212> TYPE: DNA
<213> ORGANISM: Artificial Sequence
<220> FEATURE:
<223> OTHER INFORMATION: Description of Artificial Sequence: Synthetic
    primer

```
<400> SEQUENCE: 257
gcctgctgaa aatgactg                                                    18

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf conv A2 primer

<400> SEQUENCE: 258 ggagttttg attgcttgct                                                   20

<210> SEQ ID NO 259
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf conv A2v2 primer

<400> SEQUENCE: 259
cctaaactct tcataatgct tgctc                                            25

<210> SEQ ID NO 260
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf inv B1 V600E primer

<400> SEQUENCE: 260
agctacagtg aaatctcgat gg                                               22

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf conv B2 primer

<400> SEQUENCE: 261
tgtggatggt aagaattgag gcta                                             24

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Braf inv B2 primer

<400> SEQUENCE: 262
gttcccagta ttcacaaaaa tca                                              23
```

<210> SEQ ID NO 263
<211> LENGTH: 660
<212> TYPE: DNA
<213> ORGANISM: Homo sapiens

<400> SEQUENCE: 263

```
atgtagcatt tatgcatttt tcttaagcgt cgatggagga gtttgtaaat gaagtacagt      60
tcattacgat acacgtctgc agtcaactgg aattttcatg attgaatttt gtaaggtatt     120
ttgaaataat ttttcatata aaggtgagtt tgtattaaaa ggtactggtg gagtatttga     180
tagtgtatta accttatgtg tgacatgttc taatatagtc acattttcat tattttttatt    240
ataaggcctg ctgaaaatga ctgaatataa acttgtggta gttggagctg gtggcgtagg     300
caagagtgcc ttgacgatac agctaattca gaatcatttt gtggacgaat atgatccaac     360
aatagaggta atcttgtttt taatatgcat attactggtg caggaccatt ctttgataca     420
gataaaggtt tctctgacca ttttcatgag tacttattac aagataatta tgctgaaagt     480
taagttatct gaaatgtacc tgggtttca agttatatgt aaccattaat atgggaactt     540
tactttcctt gggagtatgt cagggtccat gatgttcact ctctgtgcat tttgattgga     600
agtgtatttc agagtttcgt gagagggtag aaatttgtat cctatctgga cctaaaagac     660
```

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Conv A2 primer

<400> SEQUENCE: 264

```
tacacgtctg cagtcaactg g                                                21
```

<210> SEQ ID NO 265
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kras Inv mut Blocker

<400> SEQUENCE: 265

```
gagctggtgg cgtaggc                                                     17
```

<210> SEQ ID NO 266
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv MutG12V primer

<400> SEQUENCE: 266

```
ttggcgtagg caagagtg                                                    18
```

<210> SEQ ID NO 267
<211> LENGTH: 16

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 MutG12V primer

<400> SEQUENCE: 267
ttggcgtagg caagag                                                    16

<210> SEQ ID NO 268
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 G12D low primer

<400> SEQUENCE: 268
atggcgtagg caagag                                                    16

<210> SEQ ID NO 269
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 G12A low primer

<400> SEQUENCE: 269
ctggcgtagg caagag                                                    16

<210> SEQ ID NO 270
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 G12S low primer

<400> SEQUENCE: 270
agtggcgtag gcaagag                                                   17

<210> SEQ ID NO 271
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Inv A2 G12C low primer

<400> SEQUENCE: 271
tgtggcgtag gcaagag                                                   17

<210> SEQ ID NO 272
<211> LENGTH: 16
<212> TYPE: DNA
<213> ORGANISM: Artificial Sequence
<220> FEATURE:
<223> OTHER INFORMATION: Description of Artificial Sequence: Synthetic
```

```
    primer
<220> FEATURE:
<223> OTHER INFORMATION: Kras Inv A2 MutG13D64 primer

<400> SEQUENCE: 272
tcgtaggcaa gagtgc                                                        16

<210> SEQ ID NO 273
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras Conv B2 primer

<400> SEQUENCE: 273
ccttgacgat acagctaatt cagaatc                                            27

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Kras B2 conv primer

<400> SEQUENCE: 274
ttactggtgc aggaccattc                                                    20

<210> SEQ ID NO 275
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gcctgctgaa aatgactga                                                     19

<210> SEQ ID NO 276
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gtggcgtagg caagagtgcc tt                                                 22

<210> SEQ ID NO 277
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Amo89

<400> SEQUENCE: 277
atgatccaac aatagaggta aatctt                                             26
```

-continued

```
<210> SEQ ID NO 278
<211> LENGTH: 1200
<212> TYPE: DNA
<213> ORGANISM: Homo sapiens

<400> SEQUENCE: 278
ataaaggatt gtgcatgcat gtataggaga gcaggatacc acagcctgct tttggtttct    60
cgacaactga acattacaag aaaatctatc agaagtcttt acaatagtag gagtttttga   120
ttgcttgctt acattttatc agcactataa aactgatagt tttgtagcta tctattagtc   180
cctttcagac ctctgacctt gctcagtggt agttgagata taactgaaga ctctaaatta   240
tataacaatg aggtgagaaa aacataatat ttctcttccc taagtgcaga ctaagatact   300
atctgcagca tcttcattcc aatgaagagc ctttactgct cgcccaggag tgccaagaga   360
atatctgggc ctacattgct aaaatctaat gggaaagttt taggttctcc tataaactta   420
ggaaagcatc tcacctcatc ctaacacatt tcaagcccca aaaatcttaa aagcaggtta   480
tataggctaa atagaactaa tcattgtttt agacatactt attgactcta agaggaaaga   540
tgaagtacta tgttttaaag aatattatat tacagaatta tagaaattag atctcttacc   600
taaactcttc ataatgcttg ctctgatagg aaaatgagat ctactgtttt cctttactta   660
ctacacctca gatatatttc ttcatgaaga cctcacagta aaaataggtg attttggtct   720
agctacagtg aaatctcgat ggagtgggtc ccatcagttt gaacagttgt ctggatccat   780
tttgtggatg gtaagaattg aggctatttt tccactgatt aaattttttgg ccctgagatg   840 ctgctgagtt actagaaagt cattgaaggt ctcaactata gtattttcat agttcccagt   900
attcacaaaa atcagtgttc ttatttttta tgtaaataga ttttttaact tttttcttta   960
cccttaaaac gaatattttg aaaccagttt cagtgtattt caaacaaaaa tatatgtctt  1020
ataaacagtg tttcatattt tattcttaaa taaatatgaa cccttaaaac gaatattttg  1080
aaaccagttt cagtgtattt caaacaaaaa tatatgtctt ataaacagtg tttcatattt  1140
tattctaaat tgtttaaagt attttgtgtt caaaatgttc tgtgtaccct gttgaaaaaa  1200
```